(12) United States Patent
Daniels et al.

(10) Patent No.: US 7,866,506 B2
(45) Date of Patent: Jan. 11, 2011

(54) DEVICES USEFUL IN SYSTEM AND METHOD FOR DISPENSING PRESCRIPTIONS

(75) Inventors: Matthew P. Daniels, Pittsboro, NC (US); Jeffrey P. Williams, Hillsborough, NC (US); Richard D. Michelli, Raleigh, NC (US); Jasper Pollard, Durham, NC (US); Demetris P. Young, Durham, NC (US); Joseph C. Moran, Jr., Durham, NC (US); George Raymond Abrams, Jr., Cary, NC (US); David Alan Calderwood, Chapel Hill, NC (US); Pete Klein, Durham, NC (US)

(73) Assignee: Parata Systems, LLC, Durham, NC (US)

( * ) Notice: Subject to any disclaimer, the term of this patent is extended or adjusted under 35 U.S.C. 154(b) by 531 days.

(21) Appl. No.: 11/935,437

(22) Filed: Nov. 6, 2007

(65) Prior Publication Data

US 2008/0067190 A1 Mar. 20, 2008

Related U.S. Application Data

(62) Division of application No. 11/111,270, filed on Apr. 21, 2005, now Pat. No. 7,344,049.

(51) Int. Cl.
*B65H 1/00* (2006.01)
(52) U.S. Cl. .................. 221/122; 221/119; 221/120; 221/121

(58) Field of Classification Search ............... 221/119, 221/120, 121, 122
See application file for complete search history.

(56) References Cited

U.S. PATENT DOCUMENTS

| 688,874 | A | * | 12/1901 | McCullough ............... 221/122 |
|---|---|---|---|---|
| 2,665,775 | A | | 1/1954 | Smith |
| 2,708,996 | A | | 5/1955 | Skillman |
| 2,865,532 | A | | 12/1958 | Smith |
| 3,023,851 | A | | 3/1962 | Stiller |
| 3,144,958 | A | | 8/1964 | Gumpertz |
| 3,160,793 | A | | 12/1964 | Colburn |
| 3,179,288 | A | | 4/1965 | Davy |
| 3,185,851 | A | | 5/1965 | D'Emilio |
| 3,196,276 | A | | 7/1965 | Naab |
| 3,206,062 | A | | 9/1965 | Rappaport |
| 3,310,199 | A | | 3/1967 | Roberts |

(Continued)

FOREIGN PATENT DOCUMENTS

CA 936 501 11/1973

(Continued)

*Primary Examiner*—Timothy R Waggoner
(74) *Attorney, Agent, or Firm*—Myers Bigel Sibley & Sajovec

(57) ABSTRACT

An automated method for dispensing pharmaceuticals, particularly tablets and capsules, and other small discrete objects, includes: receiving prescription information, selecting a container, labeling the container, dispensing the tablets or capsules into the labeled container, applying a closure to the filled, labeled container, and offloading the container to a designated location. Preferably, the tablets are dispensed with high speed dispensing bins that employ forced air to agitate and singulate the tablets. The other functions within the system are typically carried out at stations designed to offer speed, flexibility and precision to the dispensing operation.

9 Claims, 45 Drawing Sheets

U.S. PATENT DOCUMENTS

| | | | |
|---|---|---|---|
| 3,312,372 A | | 4/1967 | Cooper, Jr. |
| 3,410,385 A | * | 11/1968 | Freet et al. .................. 221/121 |
| 3,410,450 A | | 11/1968 | Fortenberry |
| 3,417,542 A | | 12/1968 | Merrill |
| 3,436,736 A | | 4/1969 | Platt |
| 3,556,342 A | | 1/1971 | Guarr |
| 3,599,152 A | | 8/1971 | Williams |
| 3,653,176 A | | 4/1972 | Gess |
| 3,730,388 A | | 5/1973 | Bender |
| 3,732,544 A | | 5/1973 | Obland |
| 3,780,907 A | | 12/1973 | Colburn |
| 3,815,780 A | | 6/1974 | Bauer |
| 3,837,139 A | | 9/1974 | Roseberg |
| 3,885,702 A | | 5/1975 | Joslin |
| 3,917,045 A | | 11/1975 | Williams |
| 4,061,164 A | | 12/1977 | Sato et al. |
| 4,267,942 A | | 5/1981 | Wick |
| 4,340,249 A | | 7/1982 | Bucklew |
| 4,434,602 A | | 3/1984 | Culpepper |
| 4,546,901 A | | 10/1985 | Buttarazzi |
| 4,573,606 A | | 3/1986 | Lewis |
| 4,649,969 A | | 3/1987 | McMath |
| 4,655,026 A | | 4/1987 | Wigoda |
| 4,664,289 A | | 5/1987 | Shimizu |
| 4,674,259 A | | 6/1987 | Hills |
| 4,674,651 A | | 6/1987 | Scidmore |
| 4,693,057 A | | 9/1987 | Rittinger |
| 4,695,954 A | | 9/1987 | Rose |
| 4,741,428 A | | 5/1988 | Taniguchi et al. |
| 4,766,542 A | | 8/1988 | Pilarczyk |
| 4,767,023 A | | 8/1988 | Hackmann |
| 4,801,044 A | | 1/1989 | Kubota et al. |
| 4,805,377 A | | 2/1989 | Carter |
| 4,825,914 A | | 5/1989 | Leininger |
| 4,869,392 A | | 9/1989 | Moulding, Jr. |
| 4,899,790 A | | 2/1990 | Odenthal |
| 4,918,604 A | | 4/1990 | Baum |
| 4,971,513 A | | 11/1990 | Bergerioux |
| 4,980,292 A | | 12/1990 | Elbert |
| 4,984,709 A | | 1/1991 | Weinstein |
| 5,018,644 A | | 5/1991 | Hackmann |
| 5,047,948 A | | 9/1991 | Turner |
| 5,333,720 A | | 8/1994 | Zwigart et al. |
| 5,958,494 A | | 9/1999 | Tidland et al. |
| 6,116,821 A | | 9/2000 | Teoh et al. |
| 6,240,832 B1 | * | 6/2001 | Schmed et al. ............... 221/121 |
| 6,435,582 B1 | | 8/2002 | DaSilva et al. |
| RE37,829 E | | 9/2002 | Charhut |
| 6,631,826 B2 | | 10/2003 | Pollard et al. |
| 6,974,049 B2 | * | 12/2005 | Williams et al. ............ 221/120 |
| 2004/0004085 A1 | | 1/2004 | Williams et al. |

FOREIGN PATENT DOCUMENTS

| | | |
|---|---|---|
| GB | 1 168 758 | 10/1969 |
| GB | 1 411 951 | 10/1975 |
| JP | 51-000792 B | 1/1976 |
| JP | 52-047400 | 4/1977 |
| JP | 61-104904 | 5/1986 |
| JP | 63-208410 | 8/1988 |
| JP | 64-028102 | 1/1989 |
| JP | 1-288265 | 11/1989 |
| JP | 2-028417 | 1/1990 |

* cited by examiner

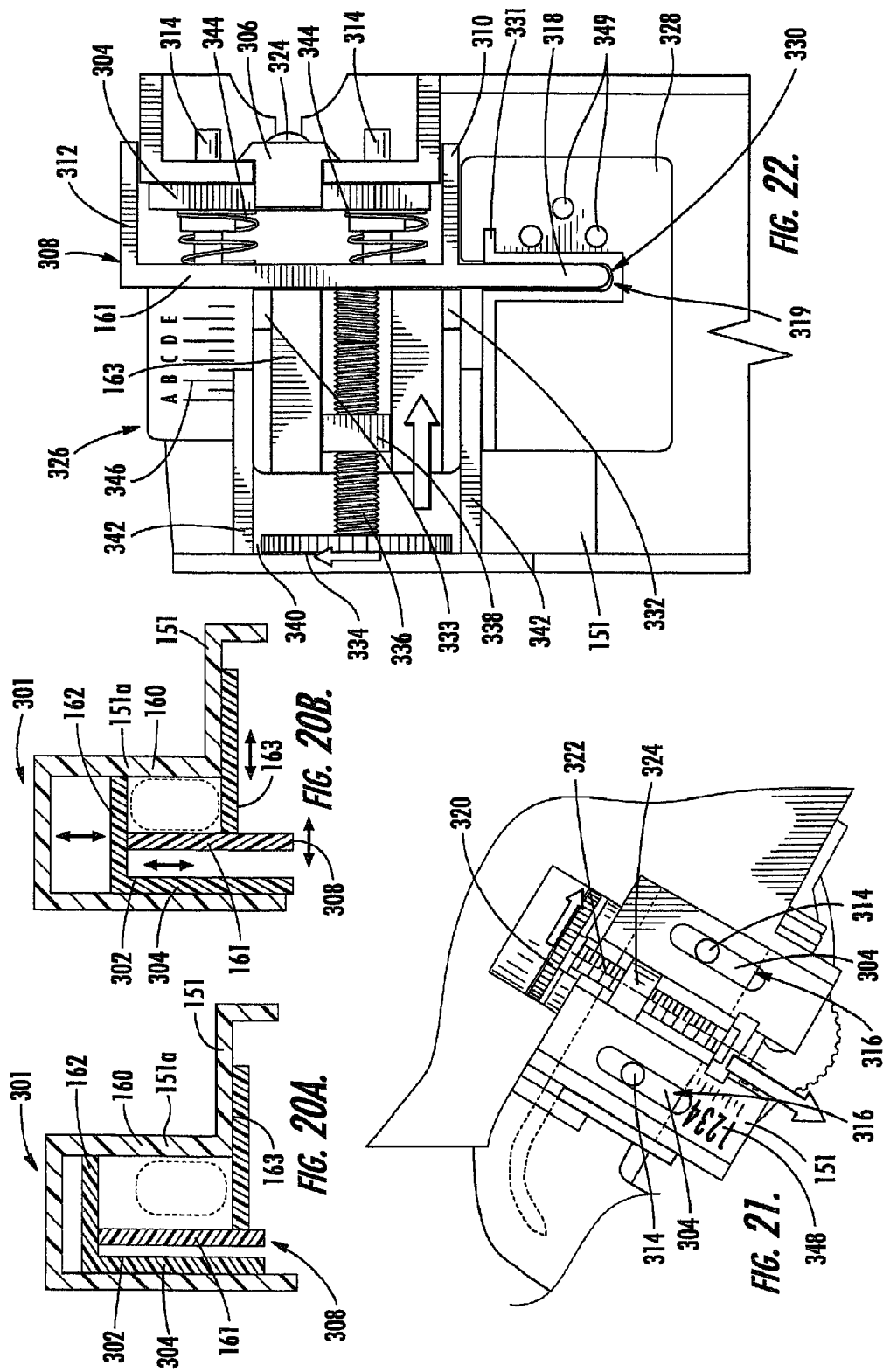

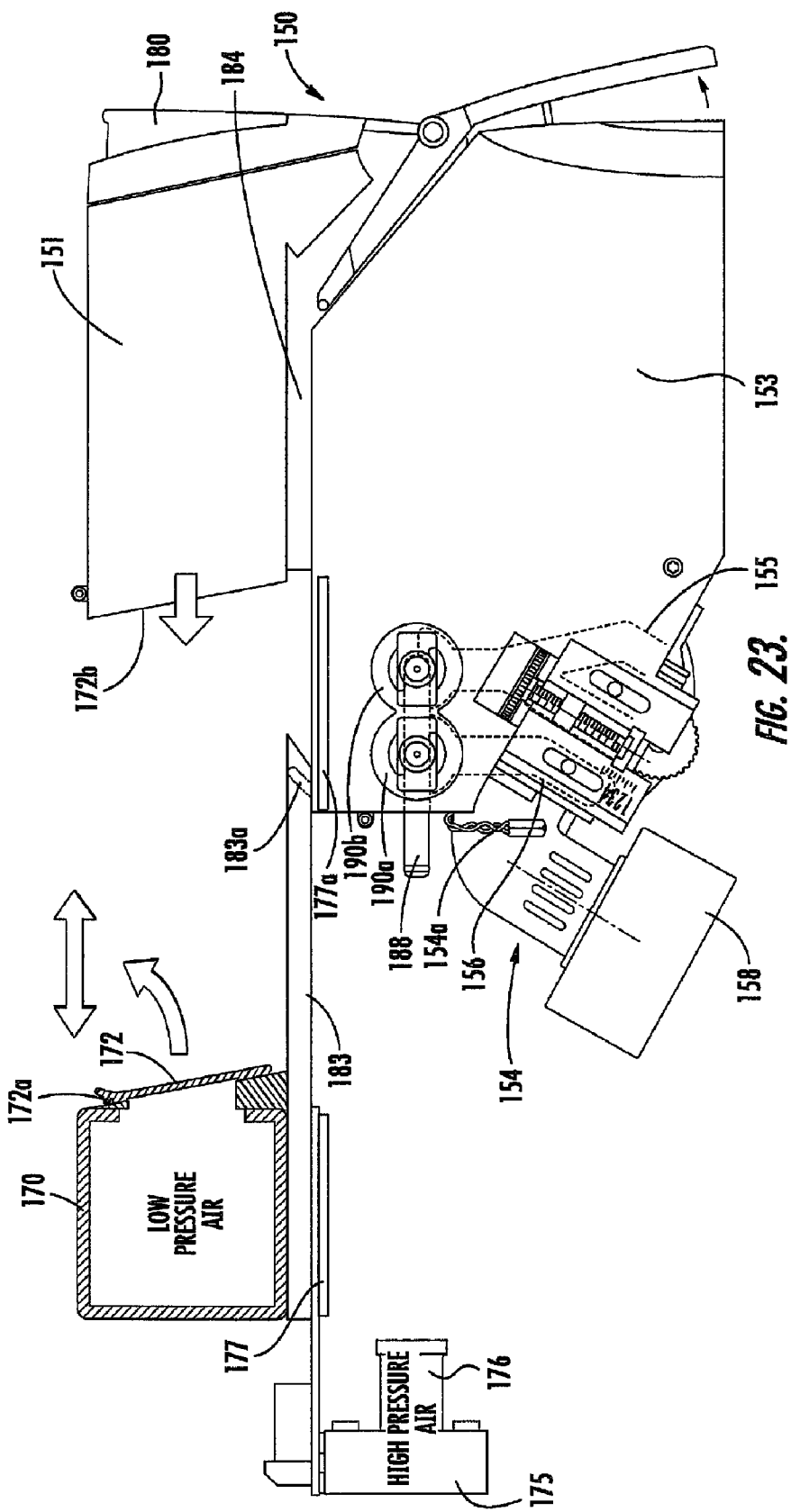

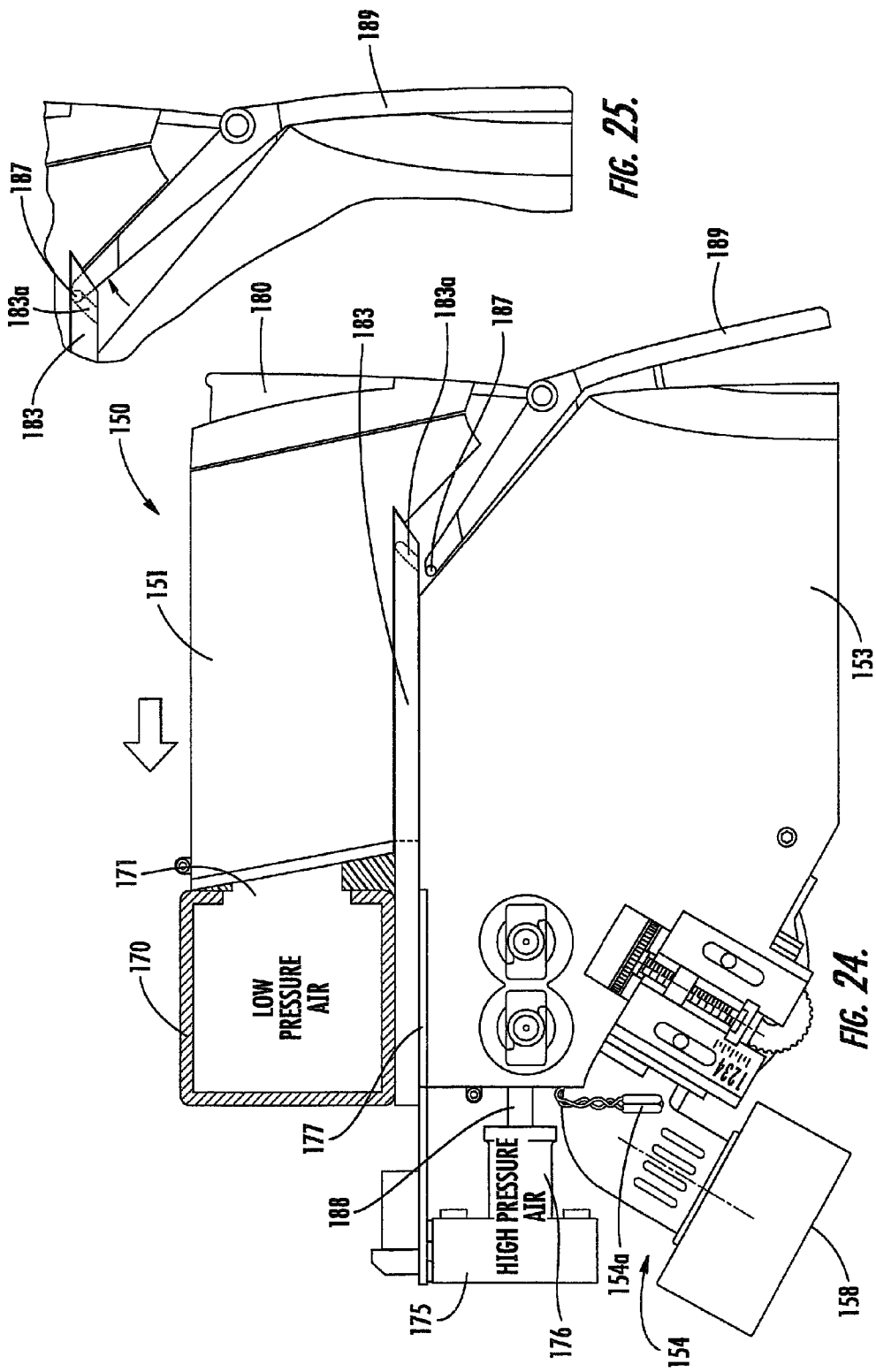

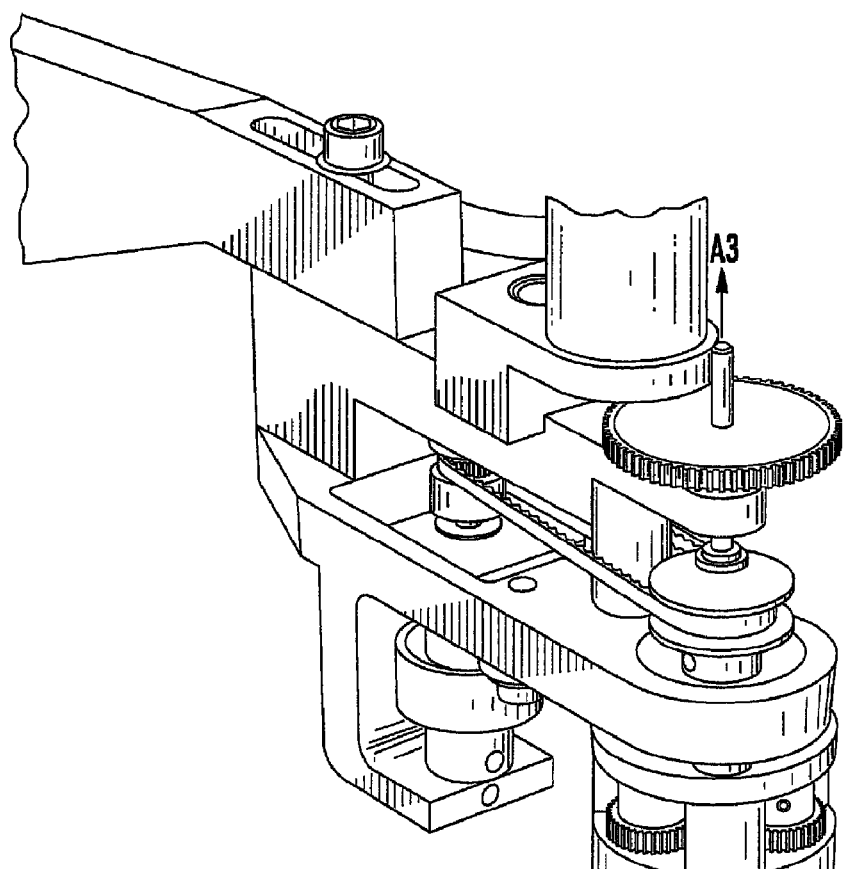
FIG. 38a.
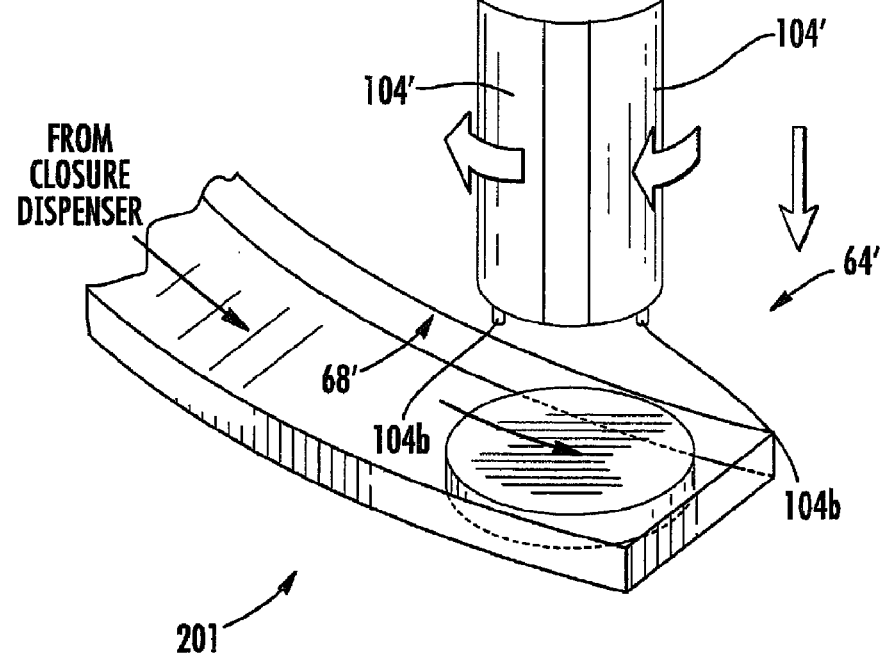

DEVICES USEFUL IN SYSTEM AND METHOD FOR DISPENSING PRESCRIPTIONS

CROSS REFERENCE TO RELATED APPLICATIONS

This application is a divisional of patent application Ser. No. 11/111,270, filed Apr. 21, 2005 now U.S. Pat. No. 7,344,049, the disclosure of which is hereby incorporated herein in its entirety.

FIELD OF THE INVENTION

The present invention is directed generally to the dispensing of prescriptions of pharmaceuticals, and more specifically is directed to the automated dispensing of pharmaceuticals.

BACKGROUND OF THE INVENTION

Pharmacy generally began with the compounding of medicines which entailed the actual mixing and preparing of medications. Heretofore, pharmacy has been, to a great extent, a profession of dispensing, that is, the pouring, counting, and labeling of a prescription, and subsequently transferring the dispensed medication to the patient. Because of the repetitiveness of many of the pharmacist's tasks, automation of these tasks has been desirable.

Some attempts have been made to automate the pharmacy environment. Different exemplary approaches are shown in U.S. Pat. No. 5,337,919 to Spaulding et al. and U.S. Pat. Nos. 6,006,946; 6,036,812 and 6,176,392 to Williams et al. These systems utilize robotic arms to grasp a container, carry it to one of a number of bins containing tablets (from which a designated number of tablets are dispensed), carry it to a printer, where a prescription label is applied, and release the filled container in a desired location. Tablets are counted and dispensed with any number of counting devices. Drawbacks to these systems typically include the relatively low speed at which prescriptions are filled and the absence in these systems of securing a closure (i.e., a lid) on the container after it is filled.

One automated system for dispensing pharmaceuticals is described in some detail in U.S. Patent Publication No. US-2004-0004085-A1. This system has the capacity to select an appropriate vial, label the vial, fill the vial with a desired quantity of a selected pharmaceutical tablet, apply a cap to the filled vial, and convey the labeled, filled, capped vial to an offloading station for retrieval. Although this particular system can provide automated pharmaceutical dispensing, it may be desirable to modify certain aspects of the system to address particular needs.

SUMMARY OF THE INVENTION

As a first aspect, embodiments of the present invention are directed to a bin for dispensing solid pharmaceutical items. The dispensing bin comprises: an upper half having an upper chamber; a lower half having a lower chamber; and a dispensing outlet projecting from the front portion of the lower half. The lower chamber is in fluid communication with the upper chamber. Each of the upper and lower halves has a front portion profile configured to mate with a frame, the frame being configured to supply low and high pressure air to the lower and upper chambers. The front portions of each of the upper and lower halves have substantially identical front profiles such that the bin can be received within the frame, with the exception that the front portion of the upper half is not configured to receive high and low pressure air. In this configuration, the dispensing bin can replace two smaller dispensing bins having the same front profile, such that larger amounts of the same tablet can be stored in one bin.

As a second aspect, embodiments of the present invention are directed to a bin for dispensing solid pharmaceutical articles, comprising: a floor, a ceiling, and side walls defining a chamber; a lower screen positioned in the floor; an upper screen positioned in the ceiling; and a first partition spanning the side walls. The partition divides the chamber into four quadrants, wherein a first quadrant is positioned forwardly of the first partition, a second quadrant is positioned above the first quadrant, a third quadrant is positioned rearwardly of the first partition, and a fourth quadrant is positioned below the third quadrant. The partition is positioned such that, when air is drawn through the chamber from the lower screen to the upper screen, at least some tablets positioned in the first quadrant travel serially from the first quadrant to the second, third and fourth quadrants. This configuration can assist in dispensing by reducing the tendency of tablets within the chamber to jam or obstruct a dispensing channel leading from the first quadrant.

As a third aspect, embodiments of the present invention are directed to a splash guard for a dispensing bin. The splash guard comprises: a grasping portion including an annular lip configured to receive and compress an outlet of the dispensing bin, the lip being formed of a first resilient material; and an annular mating portion mounted to the grasping portion, the mating portion being configured to mate with an open end of a vial. This configuration can enable the splash guard to be inserted on and removed from the dispensing channel easily and to mate with multiple vial sizes.

As a fourth aspect, embodiments of the present invention are directed to an apparatus for dispensing containers. The apparatus comprises: a plurality of dispensing tubes mounted in a generally vertical disposition and configured to receive a plurality of containers in vertically stacked relationship; a rotary drive unit associated with the dispensing tubes that rotates the dispensing tubes about a substantially vertical axis of rotation; a lower plate member positioned below the dispensing tubes, the lower plate member having a cutaway region positioned such that, as the dispensing tubes rotate about the axis of rotation, each dispensing tube passes over the cutaway region; a receptacle positioned below the cutaway region; and dislodging structure that is positioned and configured such that, when a lowermost container in a dispensing tube is lodged with a second lowermost container in that dispensing tube, the dislodging structure dislodges the lowermost container from the second lowermost container.

As a fifth aspect, embodiments of the present invention are directed to an apparatus for transporting a hollow container or closure. The apparatus comprises: a plurality of fingers having an outer surface, each of the fingers being eccentrically mounted on a mounting structure to extend generally parallel to each other in a first direction, each finger being rotatable about an axis of rotation that is generally parallel to the first direction; and a rotary drive unit operatively associated with the finger that rotates the fingers about their respective axes of rotation. The fingers are moveable between a retracted position, in which the outermost portions of the outer surfaces of the fingers define a first circle, and an extended position, in which the outermost portions of the outer surfaces of the fingers define a second circle that is larger in diameter than the first circle, the second circle corresponding to the inner perimeter of a container. The fingers include prongs extending generally parallel with the axes of rotation, the prongs being configured to grip the exterior of a lid for the container.

As a sixth aspect, embodiments of the present invention are directed to an apparatus for dispensing containers, comprising: a plurality of dispensing tubes mounted in a generally vertical disposition and configured to receive a plurality of containers in vertically stacked relationship; a rotary drive unit associated with the dispensing tubes that rotates the dispensing tubes about a substantially vertical axis of rotation; a lower plate member positioned below the dispensing tubes, the lower plate member having a cutaway region with a contact edge, the cutaway region and the contact edge being positioned such that, as the dispensing tubes rotate about the axis of rotation, each dispensing tube passes over the cutaway region; and a receptacle positioned below the cutaway region. This configuration can provide a simple, effective device for dispensing vials from the tubes.

As a seventh aspect, embodiments of the present invention are directed to an apparatus for dispensing containers, comprising: a plurality of dispensing tubes mounted in a generally vertical disposition and configured to receive a plurality of containers in vertically stacked relationship; a rotary drive unit associated with the dispensing tubes that rotates the dispensing tubes about a substantially vertical axis of rotation, the rotary drive unit being configured such that the dispensing tubes may be rotated in a first rotative direction and in a second rotative direction opposite the first rotative direction; a lower plate member positioned below the dispensing tubes, the lower plate member having a cutaway region; and a receptacle positioned below the cutaway region. The cutaway region is sized and positioned such that, as the dispensing tubes rotate about the axis of rotation in the first rotative direction, each dispensing tube passes over the cutaway region, such that a vial contained therein falls through the cutaway region into the receptacle, but when the dispensing tubes rotate in the second rotative direction, each dispensing tube passes over the cutaway region, but a vial contained therein does not fall through the cutaway region. This configuration can enable vials of different sizes to be employed in dispensing tubes of the same apparatus.

BRIEF DESCRIPTION OF THE DRAWINGS

FIGS. 20A and 20B are section views of the dispensing bin of FIG. 19 showing how the size of the dispensing channel of the dispensing bin can be adjusted.

FIG. 21 is a greatly enlarged side view of the dispending bin of FIG. 19 showing how the height of the dispensing channel can be adjusted.

FIG. 22 is a bottom view of the dispensing bin of FIG. 19 showing how the width of the dispensing channel can be adjusted.

FIG. 23 is an enlarged exploded view of the dispensing bin of FIG. 19 showing its interconnection with the low pressure manifold, the high pressure conduit, and the electronics mounted on the frame of FIG. 3.

FIG. 24 is an enlarged assembled view of the dispensing bin of FIG. 19 with the low pressure manifold, the high pressure conduit, and the electronics mounted on the frame.

FIG. 25 is an enlarged side view of the securing member of the dispensing bin of FIG. 19 showing how the securing member locks the dispensing bin in place on the frame.

FIG. 29b is a perspective view of the dispensing bin of FIG. 29a.

FIG. 29c is a greatly enlarged perspective view of the splash guard for the dispensing bin of FIG. 29a.

FIG. 38a is a perspective view of an alternative embodiment of a labeling carrier that can be used to apply a cap to a vial according to embodiments of the present invention.

DETAILED DESCRIPTION OF THE INVENTION

Figure 1:
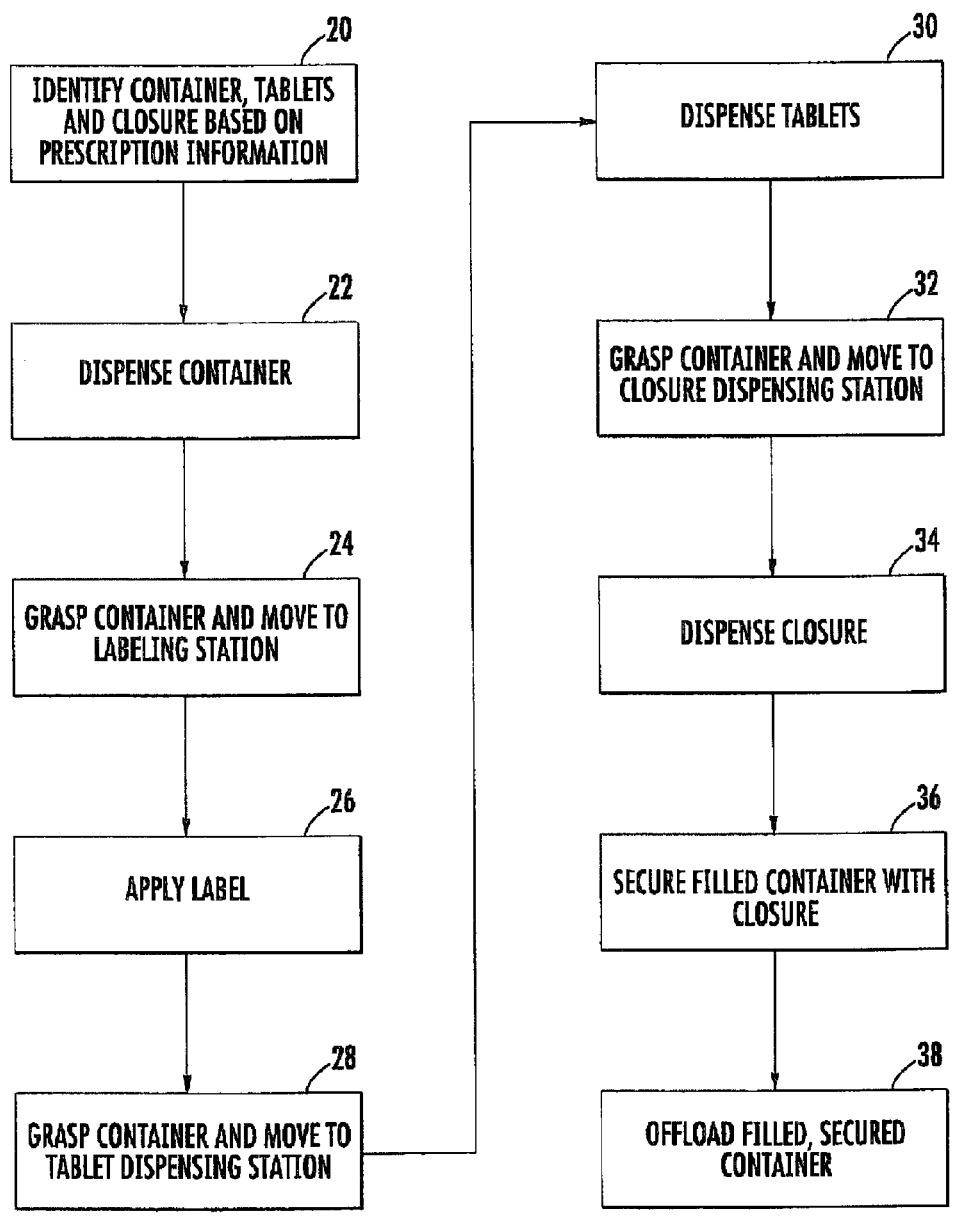
FIG. 1 is a flow chart illustrating an embodiment of a method according to the present invention.

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity. It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

As described above, the invention relates to a system and process for dispensing pharmaceuticals. The process is described generally with reference to FIG. 1. The process begins with the identification of the proper container, tablets or capsules and closure to be dispensed based on a patient's prescription information (Box 20). A container of the proper size is dispensed at a container dispensing station (Box 22), then grasped and moved to a labeling station (Box 24). The labeling station applies a label (Box 26), after which the container is transferred to a transport system and moved to a tablet dispensing station (Box 28), from which the designated tablets are dispensed in the designated amount into the container (Box 30). The filled container is then grasped again and moved to a closure dispensing station (Box 32), where a closure of the proper size has been dispensed (Box 34). The filled container is secured with a closure (Box 36), then transported to an offload station and offloaded (Box 38).

Figure 2:
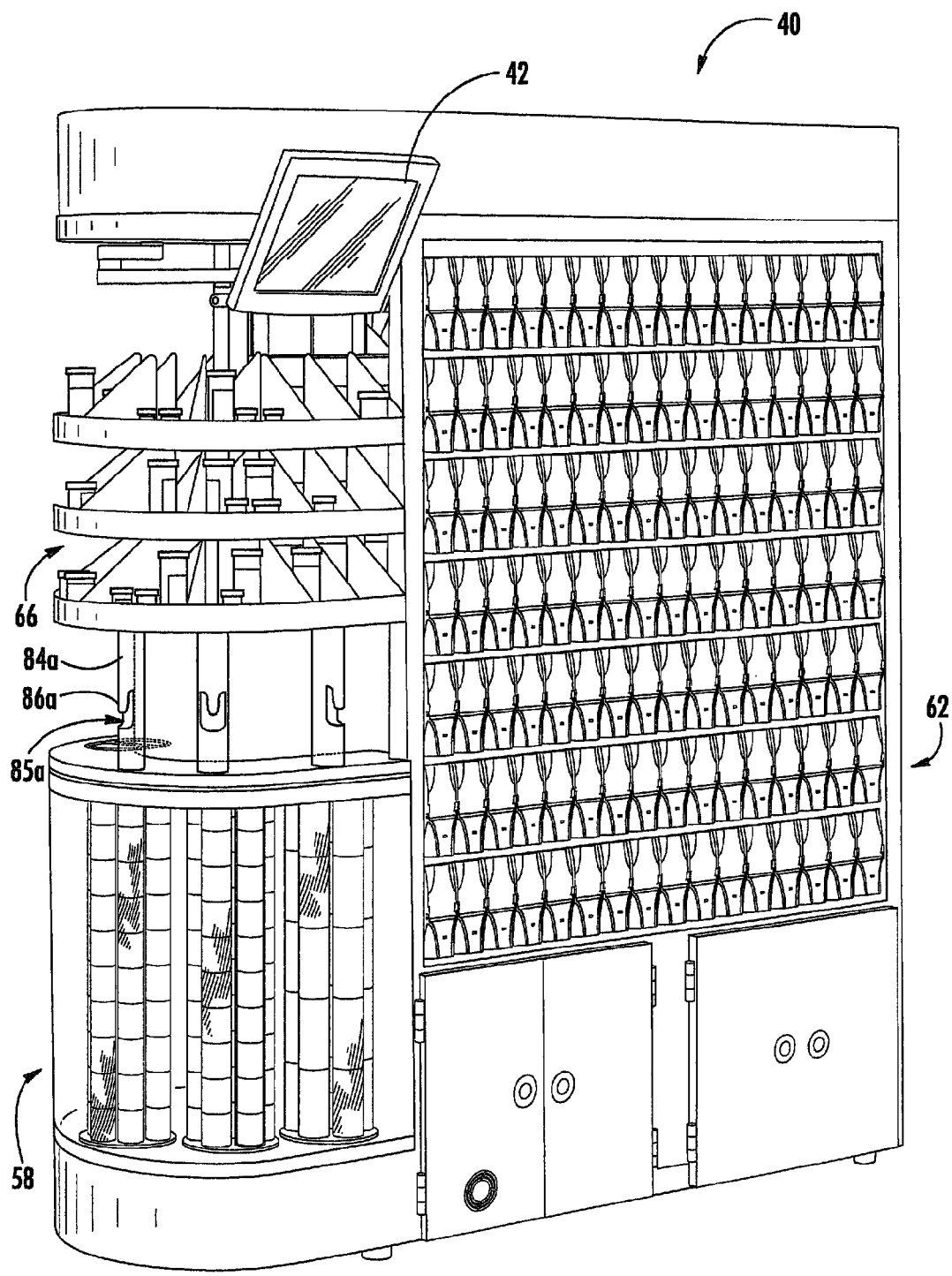
FIG. 2 is a perspective view of a pharmaceutical tablet dispensing system according to the present invention.
Figure 3:
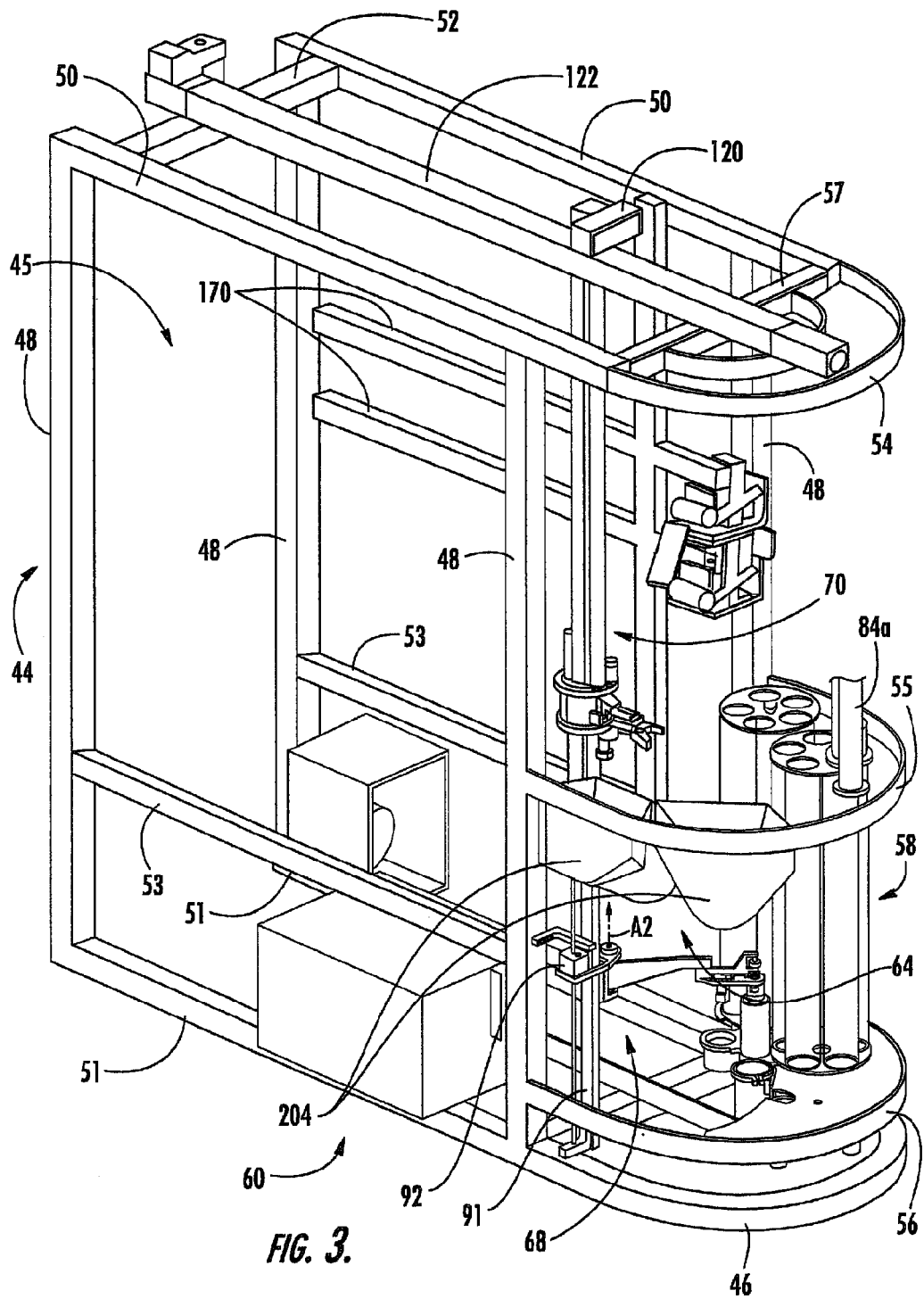
FIG. 3 is a cutaway view of the system of FIG. 2 illustrating the container dispensing station, the labeling carrier, the dispensing carrier, and the closure dispensing station.

A system that can carry out this process is illustrated in FIGS. 2-37 and designated broadly therein at 40. Referring first to FIGS. 2 and 3, the system 40 includes a support frame 44 for the mounting of its various components. The illustrated support frame 40 includes a base 46 that rests on an underlying surface. Four uprights 48 extend vertically from the base 46 and define an internal cavity 45 within which the operable components of the system 40 generally reside. A pair of top rails 50 are attached to the upper ends of the uprights 48, and two cross-members 52 span the distance between the front and rear ends of the top rails 50. Top, intermediate and bottom arches 54, 55, 56 are mounted to extend from the front surfaces of the front uprights 48. The frame 44 also includes two lower rails 51 that extend between pairs of uprights 48 well below the top rails 52, and further includes a pair of intermediate rails 53 that are mounted in vertical alignment between two uprights 48 below one of the top rails 52.

Those skilled in this art will recognize that the frame 40 illustrated herein is exemplary and can take many configurations that would be suitable for use with the present invention. The frame 40 provides a strong, rigid foundation to which other components can be attached at desired locations, and other frame forms able to serve this purpose may also be acceptable for use with this invention.

Referring again to FIGS. 2 and 3, the system 40 generally includes as operative stations a controller 42, a container dispensing station 58, a labeling station 60, a tablet dispensing station 62, a closure dispensing station 64, and an offloading station 66. Containers, tablets and closures are moved between these stations with two different conveying devices: a labeling carrier 68 and a dispensing carrier 70. Each of the operative stations and the conveying devices is described in detail below.

The controller 42, which is mounted to and below the top arch 54, controls the operation of remainder of the system 40. In some embodiments, the controller 42 will be operatively connected with an external device, such as a personal or mainframe computer, that provides input information regarding prescriptions. In other embodiments, the controller 42 may be a stand-alone computer that directly receives manual input from a pharmacist or other operator. An exemplary controller is a conventional microprocessor-based personal computer.

Figure 4:
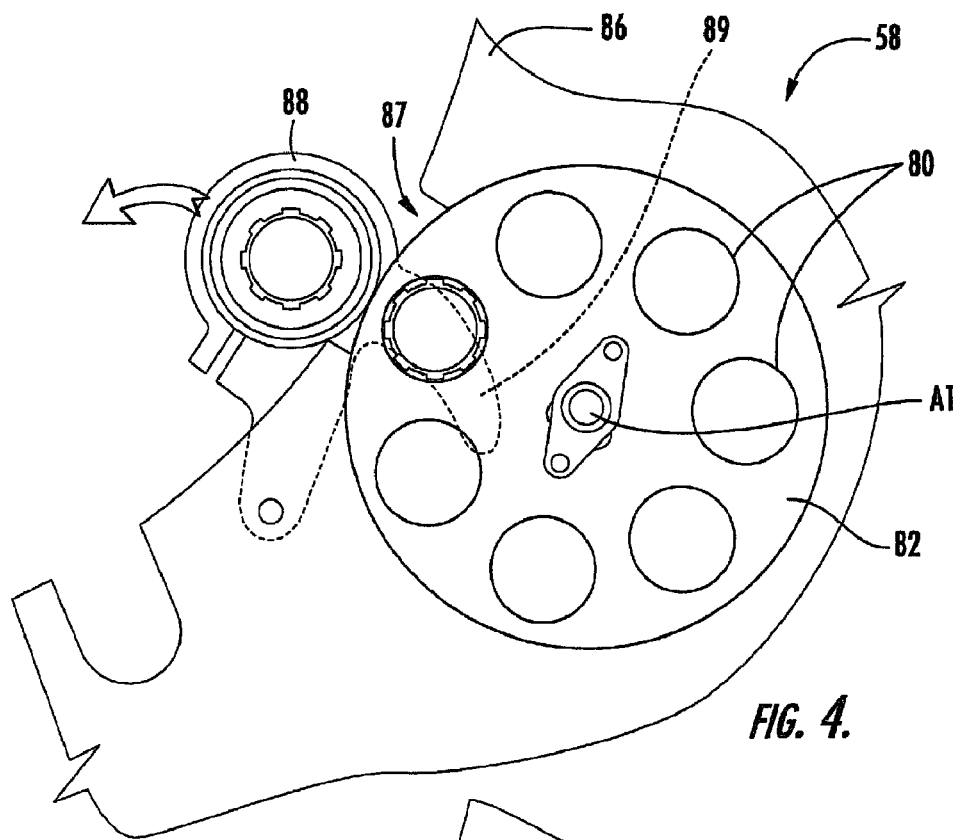
FIG. 4 is a top view of the container dispensing station of the system of FIG. 2 showing the cup holding a container in the donating position.
Figure 5:
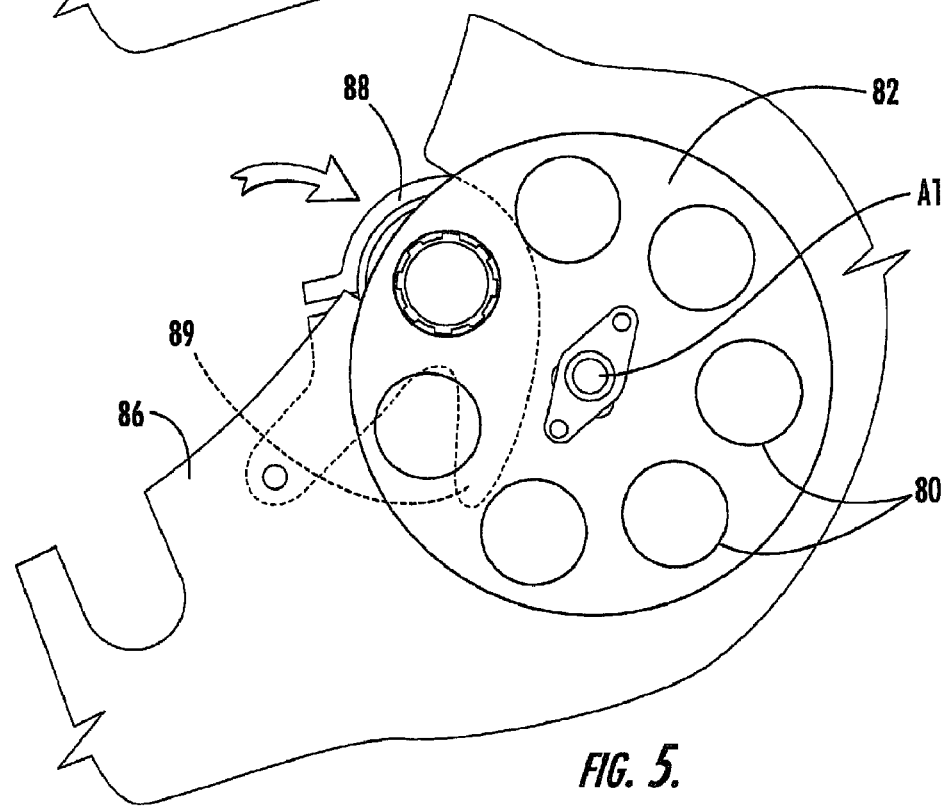
FIG. 5 is a top view of the container dispensing station of FIG. 4 showing the cup holding a container in the receiving position.
Figure 6:
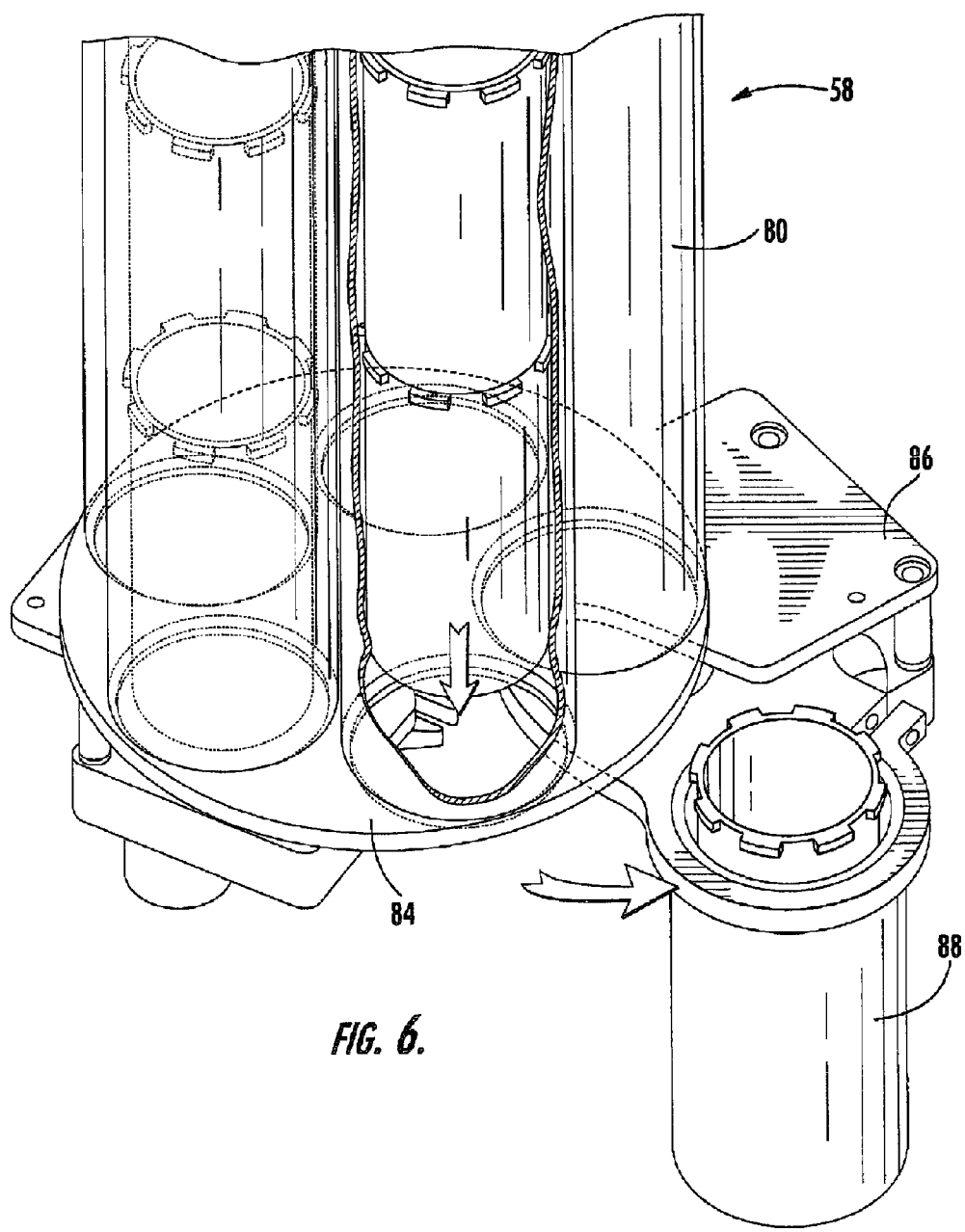
FIG. 6 is an enlarged perspective view of the container dispensing station of FIG. 4.

Referring now to FIGS. 4-6, the container dispensing station 58, which is mounted to the bottom arch 56, comprises a plurality of tubes 80 oriented generally vertically and about a common axis of rotation. In the illustrated embodiment, three sets of tubes 80 of different sizes are illustrated; the ensuing discussion is equally applicable to each.

A bottom plate 82 is fixed to the bottom ends of the tubes 80 and a top plate 84 fixed to the top ends of the tubes 80. Each of the bottom and top plates 82, 84 have apertures that correspond to the ends of the tubes 80. The tubes 80 and bottom and top plates 82, 84 are free to rotate as a unit about the axis of rotation A1 and are driven by a motor or other rotary drive unit attached to the bottom plate 82 (the motor is not shown). A sorting plate 86 or other member is fixed to the lower arch 56 below and parallel to the bottom plate 82. The sorting plate 86 includes a slotted opening 87 at one edge. As is shown in FIGS. 5 and 5, a cup 88 or other receiving member is pivotally attached to lower surface of the sorting plate 86 such that it may move between a receiving position below the opening 87 (FIG. 5) and a donating position beyond the perimeter of the sorting plate 86 (FIG. 4) (pivoting of the cup 88 is controlled by the controller 42 through a second motor (not shown)).

Prior to operation, the tubes 80 within each set are filled with containers of similar size, with each set of tubes 80 housing containers of different sizes. Filling can be carried out by loading the containers in a preferred orientation through an orientation tube 84a (see FIG. 2), which has an opening 85a with a downward extending finger 86a that ensure that the containers are loaded with their open ends facing upwardly. The containers travel through the orientation tube 84 through the openings in the top plate 84 in an upright orientation with their open ends facing upwardly, so that they are vertically stacked within the tubes 80. In some embodiments, each set of tubes 80 is filled with different sizes of containers, while in other embodiments, individual tubes 80 within the same set of tubes may be filled with different sizes of containers.

In operation, the controller 42 signals the container dispensing station 58 that a container of a specified size is desired. The bottom and top plates 82, 84 rotate until a tube 80 that houses a container is positioned above the opening 87. At this point, the cup 88 is in its receiving position beneath the opening 87 (FIG. 5). The lowermost container drops downwardly through the opening 87 and into the cup 88. The controller 42 then signals the cup 88 to pivot to its donating position (FIGS. 4 and 6), wherein the container can be grasped by the labeling carrier 68. The cup 88 includes a support finger 89 trailing the receptacle portion of the cup 88 to support containers remaining in the tubes 80 when the cup 88 is in the donating position.

An alternative embodiment of the container dispensing station is illustrated in FIGS. 6a-6f and designated broadly therein at 58'. The container dispensing station 58' includes tubes 80' vertically mounted around a central spindle (not shown) for rotation about an axis of rotation Z. Each of the tubes 80' has a bottom edge 80a configured such that the radially outward portions of the bottom edges 80a are raised relative to the radially inward portions. A bottom plate 82' is disposed below the tubes 80' at an elevation that is slightly lower than that of the radially inward portions of the bottom edges 80a of the tubes 80'. The bottom plate 82' has a cutaway portion 82c that is bounded on one side by a contact edge 82a. A ramp 83 leads from the upper surface of the bottom plate 82' to the cutaway area 82c, such that the bottom edge of the ramp 83 and the contact edge 82a form an angle of approximately 90 degrees (although this angle may differ in other embodiments). A guide plug 82b is mounted on the upper surface of the bottom plate 82' below the radially inward portion of one of the tubes 80' near the entry of the ramp 83. A guide wedge 89 is mounted to the upper surface of the bottom plate 80' at the radially outward end of the contact edge 82a. An engagement ledge 81 extends into the radially inward portions of the tubes 80' positioned above or immediately adjacent the cutaway area 82c and extends for approximately 180 degrees about the axis Z; the engagement ledge 81 is mounted such that it remains stationary when the tubes 80' rotate about the axis Z.

Still referring to FIGS. 6a-6f, the container dispensing station 58' also includes a slide channel 88'. The slide channel 88' includes a slide surface 88a that leads downwardly from the bottom end of the ramp 83. A receptacle 88b is located in the lower portion of the slide channel 88'.

In operation, vials are loaded into the tubes 80' as described above with respect to the dispensing station illustrated in FIGS. 4-6. As the tubes 80' rotate about the axis Z, the lowermost vial V1 in each tube 80' slides down the ramp 83 to the cutaway area 82c (FIG. 6c). Ordinarily the movement of the tube 80' and the interaction between the tube 80' and the vial V1 drags the vial V1 across the cutaway area 82c such that the lower end of the descending vial V1 strikes the contact edge 82a. The rotational movement of the vial V1 ceases, and the vial V1 slides down the slide surface 88a of the slide channel 88' to the receptacle 88b for retrieval by the labeling carrier 68 (FIG. 6d).

Those skilled in this art will recognize that other configurations for capturing the lowermost vial V1 may also be employed. For example, the container dispensing unit may lack a ramp leading to the cutaway area, and the contact edge may comprise a raised ledge or wall that the vial V1 strikes, or a dispensing unit may have both an entry ramp and a raised wall. Other configurations known to those skilled in this art may also be suitable.

Figure 6A:
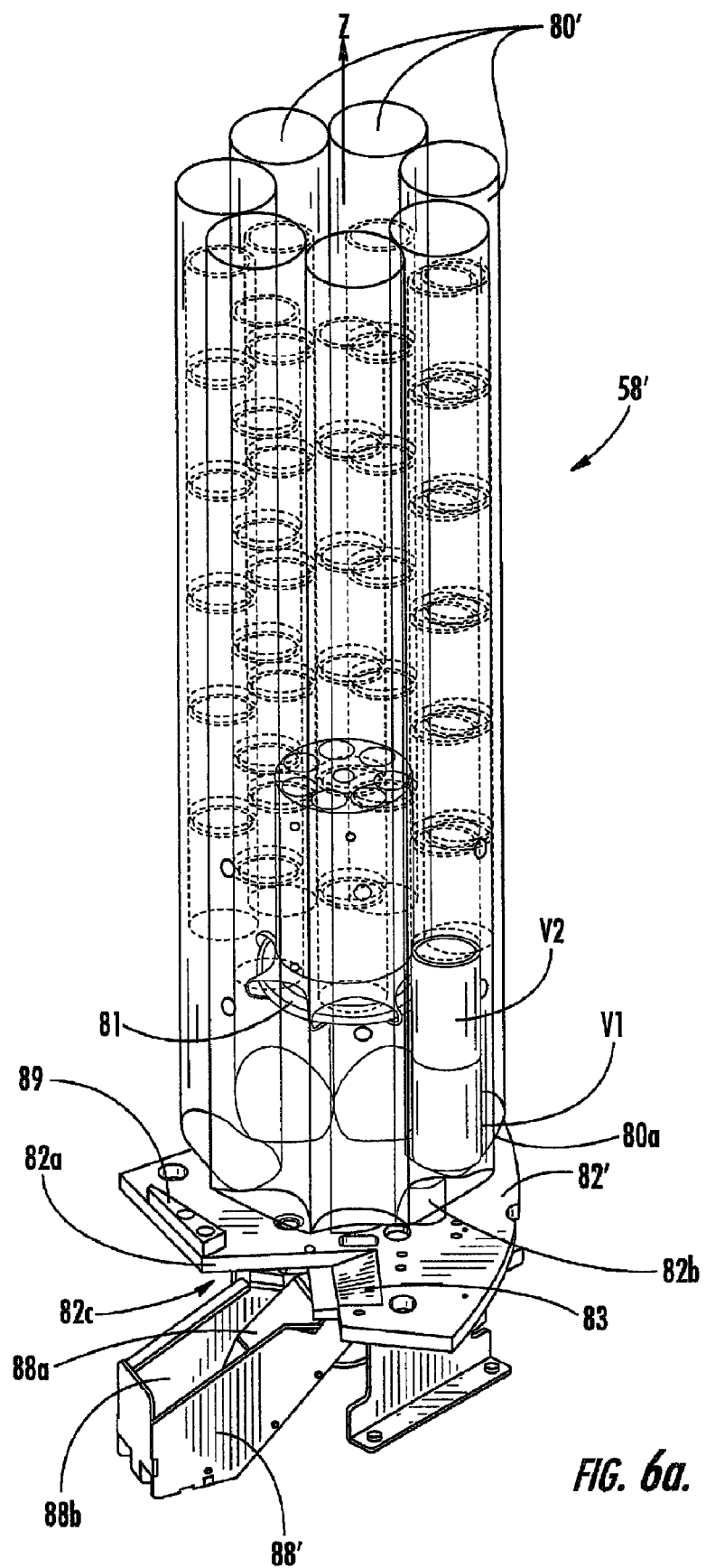
FIG. 6a is a perspective view of a container dispensing station according to alternative embodiments of the present invention.
Figure 6B:
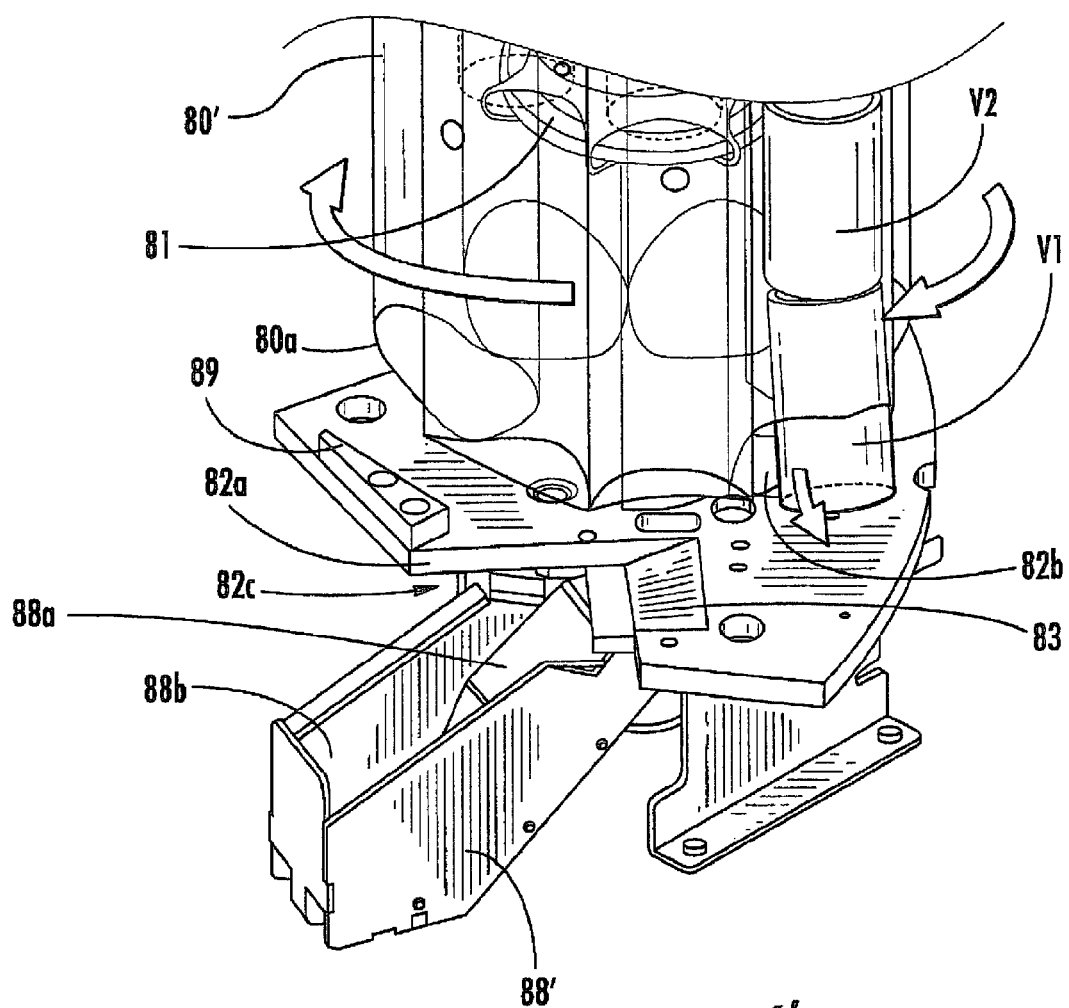
FIG. 6b is an enlarged view of the container dispensing station of FIG. 6a showing a lowermost vial in a dispensing tube being forced radially outwardly by a guide plug during dispensing of the vial.
Figure 6C:
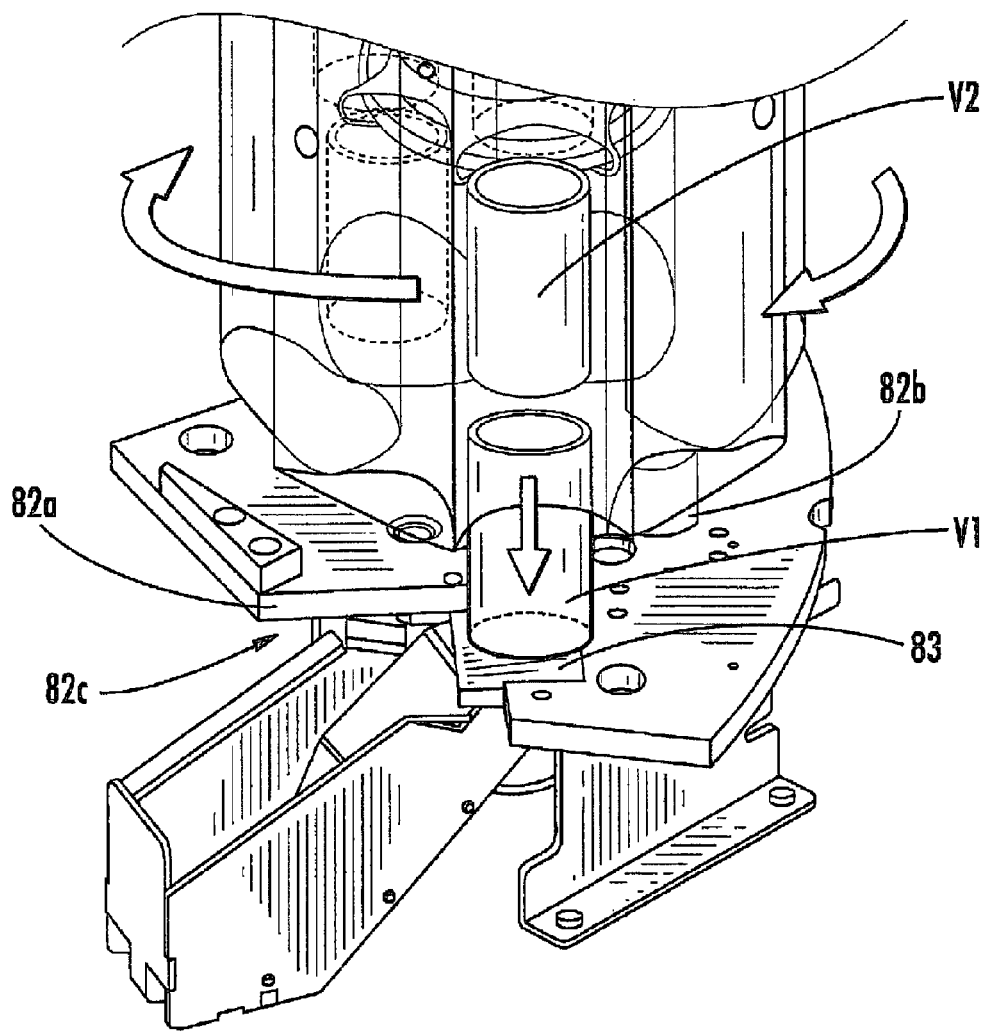
FIG. 6c is an enlarged view of the container dispensing station of FIG. 6a showing the lowermost vial moving down the ramp of the lower plate and striking the engagement edge thereof.
Figure 6D:
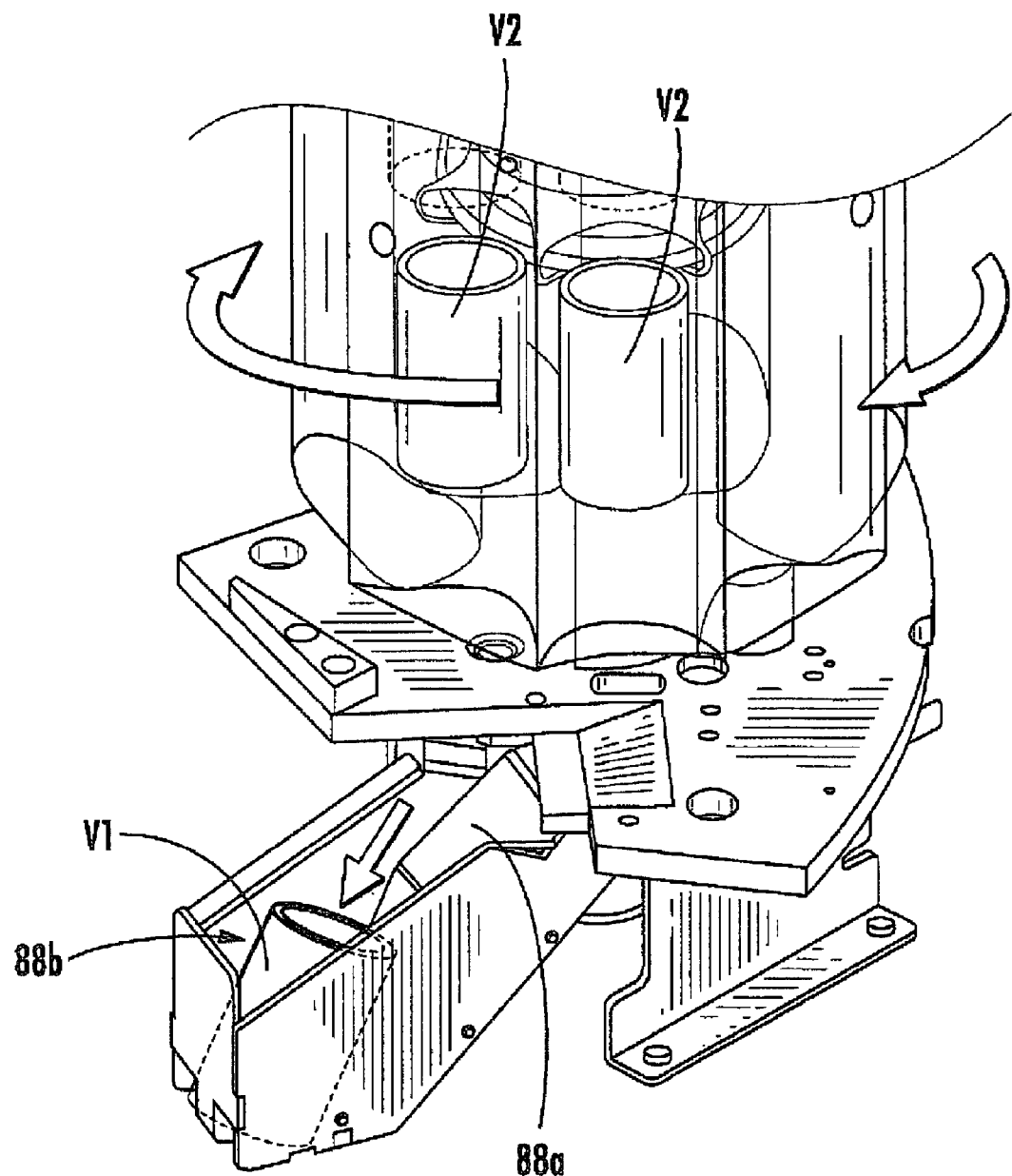
FIG. 6d is an enlarged view of the container dispensing station of FIG. 6a showing the lowermost vial descending into slide channel.

In some instances, the lowermost vial V1 may become lodged with the second lowest vial in the stack V2 (see FIG. 6a). To prevent both vials V1, V2 from dropping into the receptacle 88b, the engagement ledge 81 is positioned vertically such that, as a stack of vials is positioned in a tube 80', the radially inward lip of the second vial V2 from the bottom is above the engagement ledge 81 (FIG. 6d). As such, when the tubes 80' rotate about the axis Z to dispense a vial (the rotation is clockwise when viewed from above), the lowermost vial V1 is free to drop into the cutaway area 82c while the vial V2 is prevented from following the lowermost vial V1 into the cutaway area 82c by the engagement ledge 81. As the tubes 80' continue to rotate, the tube 80' holding vial V2 reaches the end of the engagement ledge 81 (which, as noted above, only extends approximately 180 degrees about the axis Z), at which point the vial V2 is free to drop to the bottom of the stack for dispensing.

In addition, the guide plug 82b assists in dislodging the lowermost vial V1 from the vial V2. As shown in FIG. 6b, as the tube 80' containing the vials V1, V2 passes the guide plug 82b, the radially inward portion of the lowermost vial V1 contacts the guide plug 82b. This contact forces the lower end of the vial V1 to swing radially outward. Because the bottom edge 80a of the dispensing tube 80' is beveled, the lower end of the vial V1 can swing outwardly a sufficient distance that any lodging or sticking between the upper end of the vial V1 and the lower end of the vial V2 is overcome.

Figure 6E:
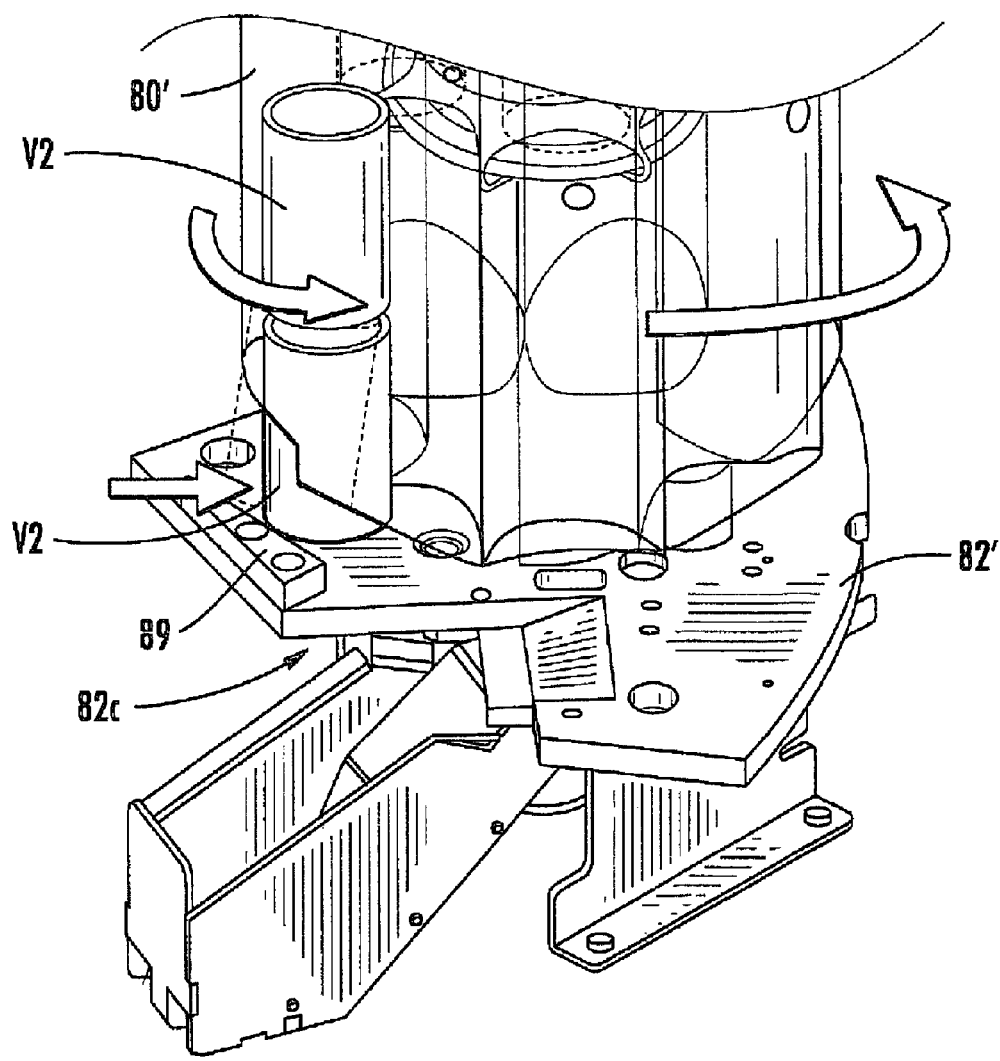
FIG. 6e is an enlarged view of the container dispensing station of FIG. 6a rotating in a non-dispensing direction showing the guide wedge forcing the lowermost vial radially inwardly.
Figure 6F:
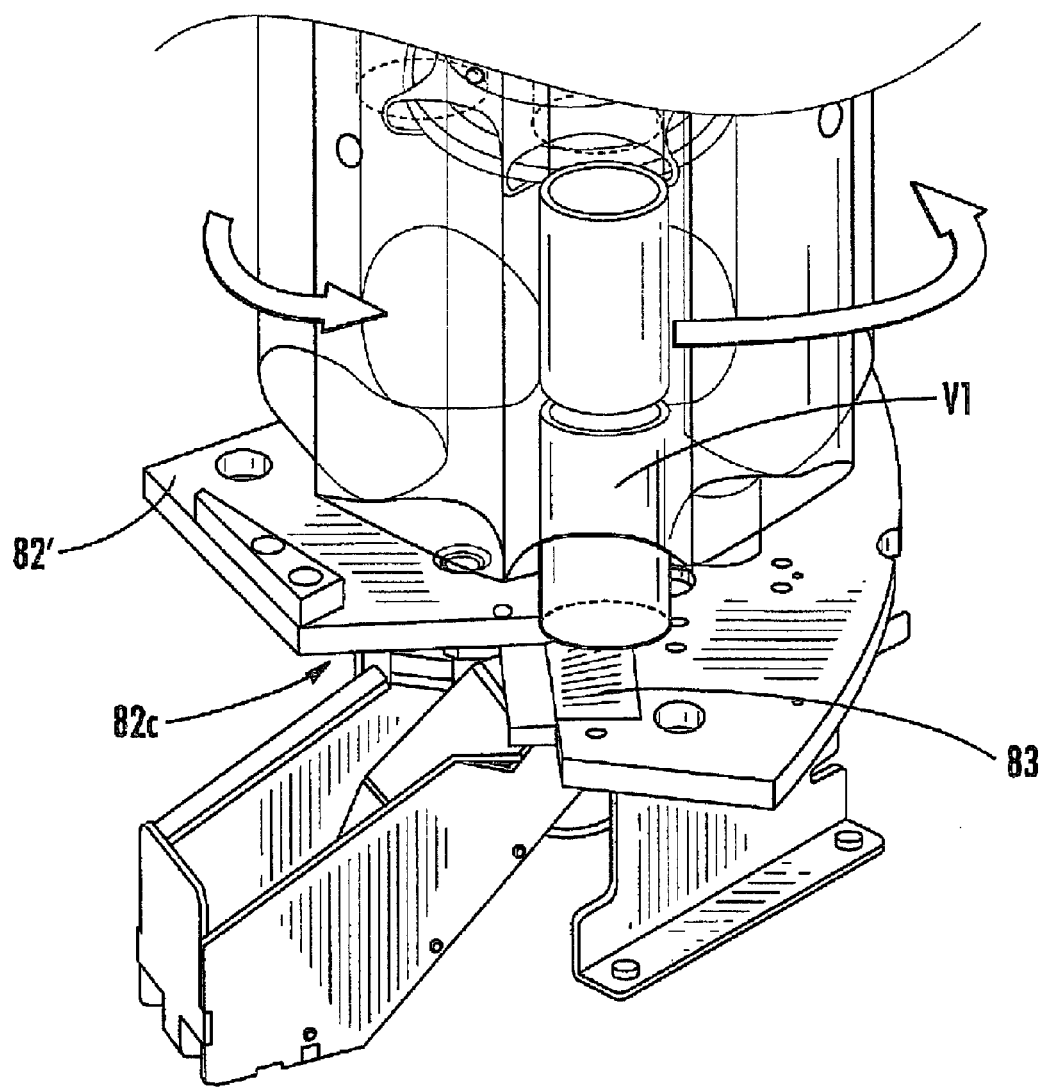
FIG. 6f is an enlarged view of the container dispensing station of FIG. 6a rotating in a non-dispensing direction showing how the lowermost vial can travel past the cutaway area of the lower plate without sliding into the slide channel.
Figure 7:
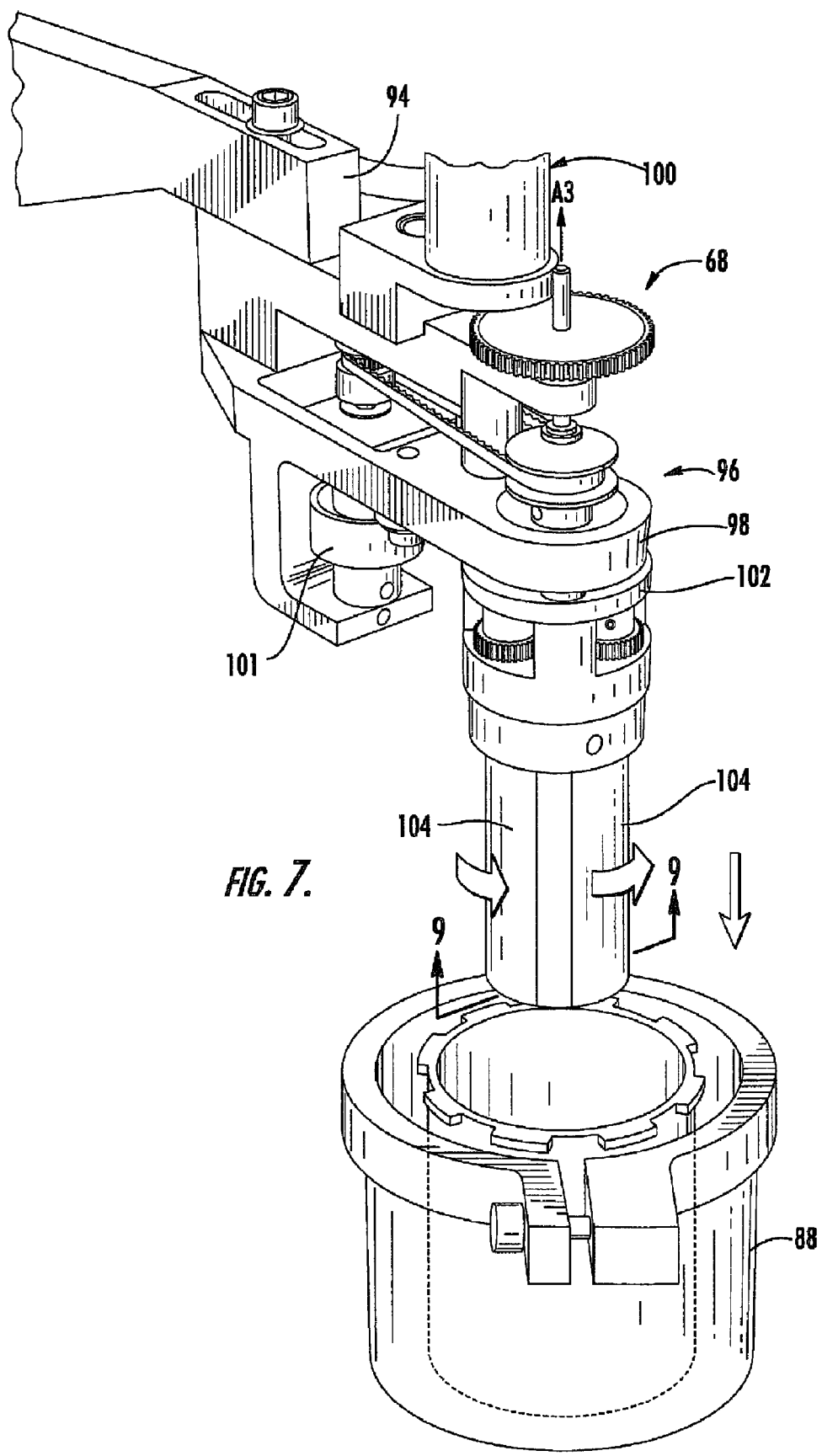
FIG. 7 is a perspective view of the gripping unit of the label carrier of the system of FIG. 2 with the fingers thereof rotated to a radially inward position and the unit itself in a raised position above the container-dispensing cup.
Figure 7A:
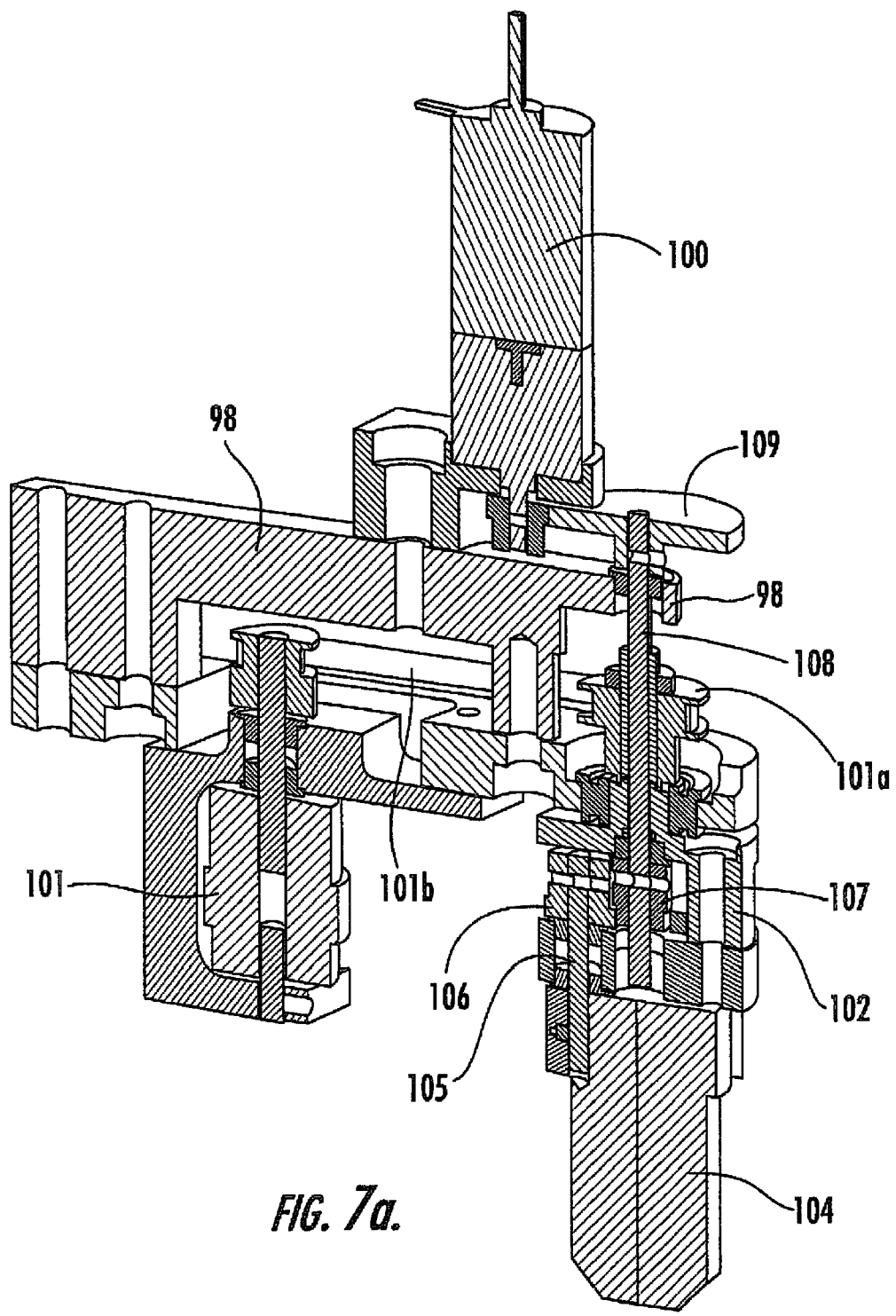
FIG. 7A is a section view of the gripping unit of FIG. 7.
Figure 8:
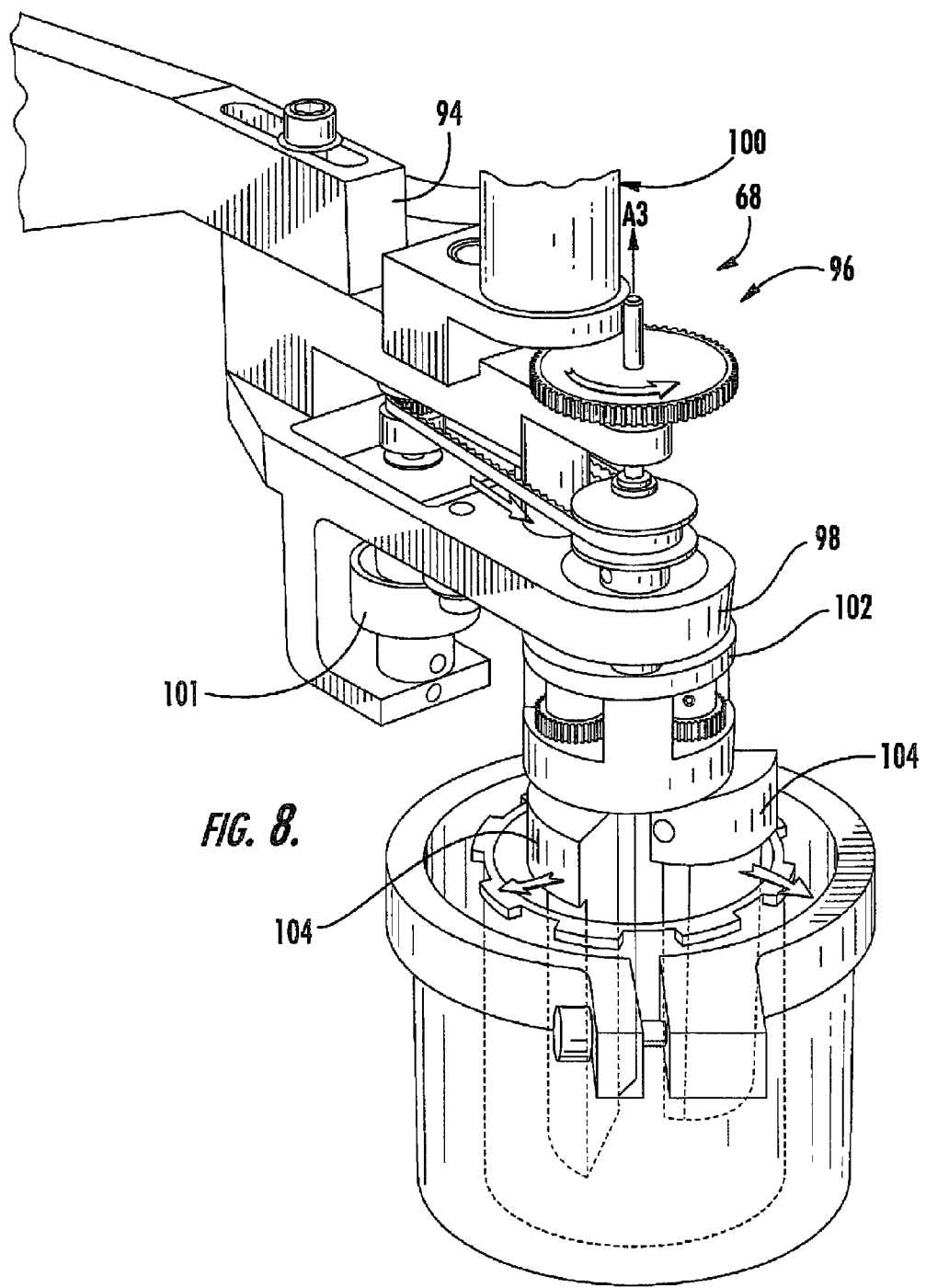
FIG. 8 is a perspective view of the gripping unit of FIG. 7 with the fingers thereof in the process of rotating radially outwardly and the unit itself in a lowered position into a container in the container dispensing cup.
Figure 9:
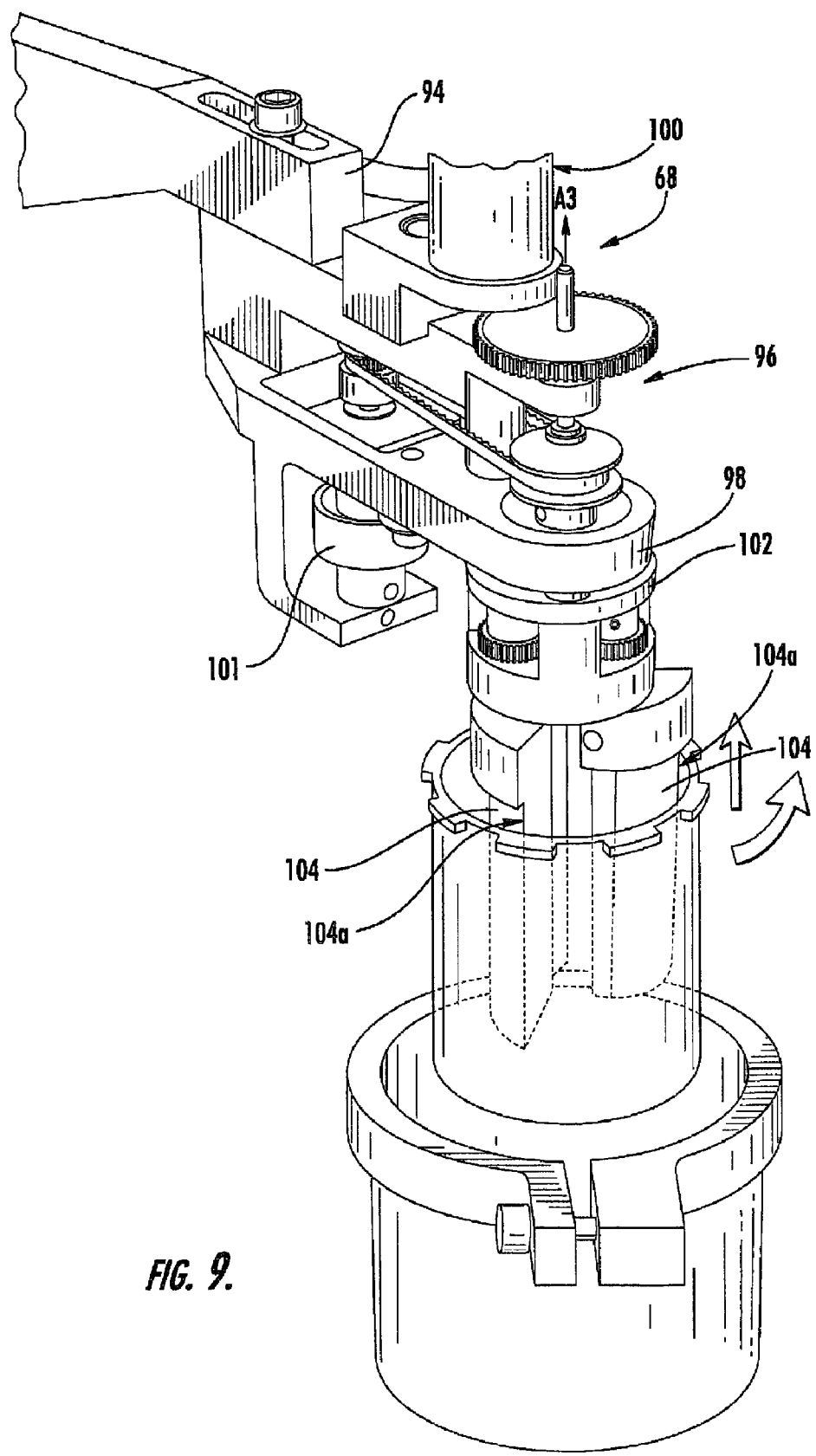
FIG. 9 is a perspective view of the gripping unit of FIG. 7 with the fingers thereof rotated to a radially outward position and the unit itself rising with the container above the container dispensing cup.
Figure 10:
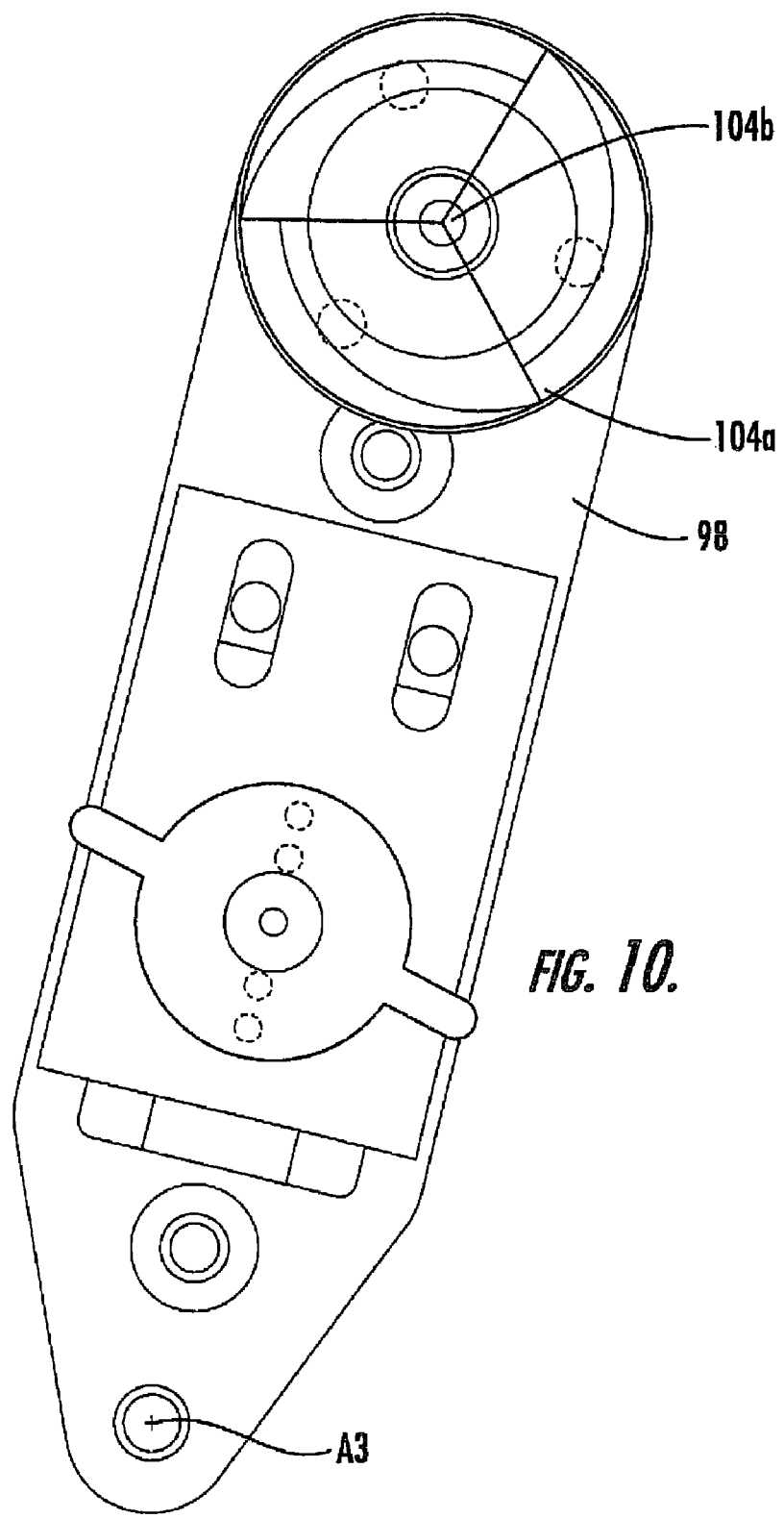
FIG. 10 is a bottom view of the gripping unit of FIG. 7 with the fingers thereof in rotated to a radially inward position.
Figure 11:
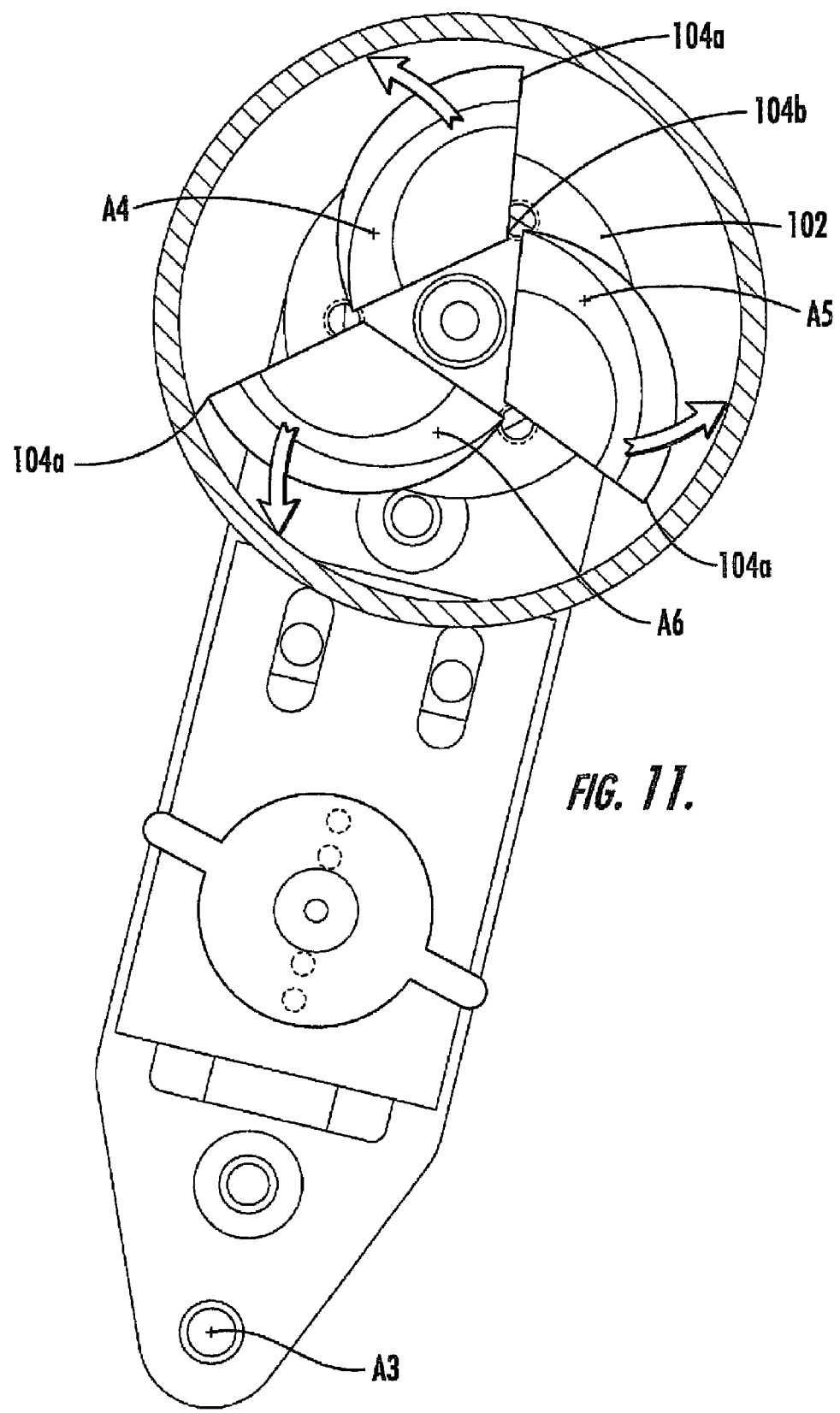
FIG. 11 is a bottom view of the gripping unit of FIG. 7 with the fingers thereof rotated to an intermediate position.
Figure 12:
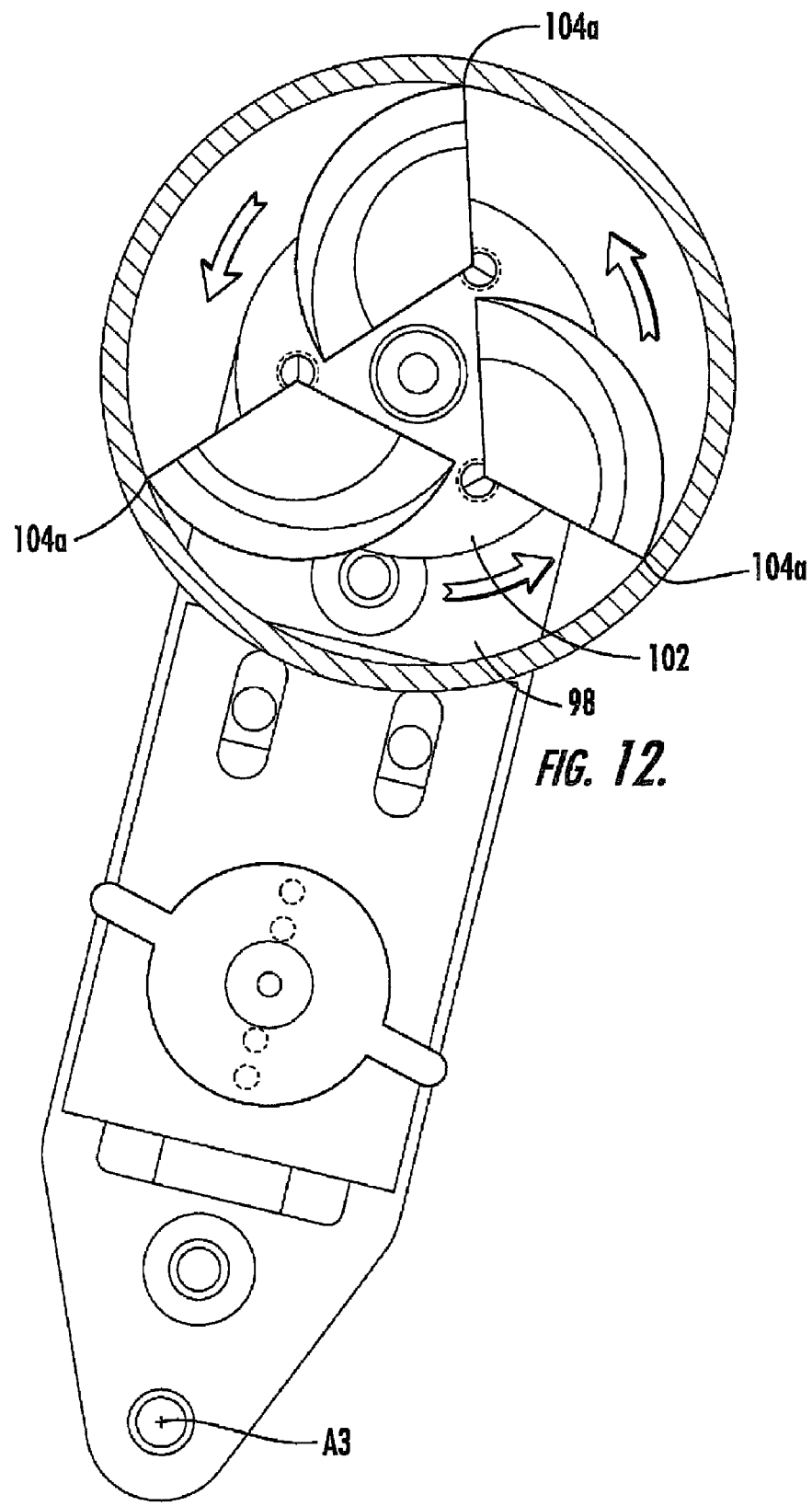
FIG. 12 is a bottom view of the gripping unit of FIG. 7 with the fingers thereof in rotated to a radially outward position.

Referring now to FIGS. 6e and 6f, it should also be noted that the presence of the guide wedge 89 can allow the tubes 80' to be rotated in the opposite direction (counterclockwise when viewed from above) without vials being dispensed. If the tubes 80' are rotated in the non-dispensing direction, the lowermost vial V1 in each tube 80' contacts the guide wedge 89 prior to reaching the cutaway area 82c. This contact shifts the vial V1 radially inwardly, which movement positions the vial such that some of its lower surface rests on the bottom plate 82 and is not directly above the cutaway area 82c as it passes thereover. Interaction between the moving tube 80' and the vial V1 is sufficient to drag the vial V1 up the ramp 83 and escape the cutaway area 82c without dropping in. Rotation of the tubes 80' in the opposite direction may be desirable, for example, if vials of different sizes are stored and dispensed in the tubes 80'.

Those skilled in this art will appreciate that other configurations for enabling reversible rotation of the container dispensing unit to occur without any vials dropping into the receptacle 88b. For example, the guide wedge 89 may be omitted, in which case the cutaway area 82c may not extend radially inwardly as far as would be the case otherwise. Other configurations may also be employed.

Those skilled in this art will appreciate that other container dispensing apparatus may be employed with the present invention. For example, the containers may be presented for grasping in a horizontal disposition, or the dispensing apparatus may include a conveyor unit that presents the containers one at a time for grasping. Also, other apparatus for dislodging lodged vials, such as a moveable finger or arm that contacts the lowermost vial as it passes by, may also be used. The skilled artisan will recognize additional embodiments that would be suitable for use with the inventive system.

From the container dispensing station 58, the container is moved to the labeling station 60; this movement is carried out by the labeling carrier 68 (see FIGS. 3 and 7-12). The labeling carrier 68 comprises an upright support member 91 fixed to the base of the frame 40, a carriage 92 attached to and moveable vertically on the support member 91, a swing arm 94 attached thereto that pivots about a vertical axis A2, and a gripping unit 96 attached to the free end of the swing arm 94. Both the vertical movement of the carriage 92 and the pivoting of the swing arm 94 and gripping unit 96 can be induced with conventional robotic techniques that need not be described in detail herein.

The gripping unit 96 has a body portion 98, a base 102 rotatably attached to the body portion 98 for rotation about an axis A3, a clutch mechanism 101 attached to the body portion 98 and coupled to the base 102, a plurality of fingers 104 (three are illustrated herein) that are rotatable and eccentrically mounted to the base 102 and extend downwardly therefrom generally parallel to each other, and a motor 100 attached to the body portion 98 and coupled to the fingers 104. Each finger 104 is fixed to a finger shaft 105, which in turn is fixed to a planet gear 106 such that, as the planet gear 106 rotates, so must the attached finger 104. Each planet gear 106 is attached to the base 102 in such a way as to be able to rotate freely relative thereto. A sun gear 107 is rotatably mounted onto the base 102 and can freely rotate in relation thereto about the axis A3. Each planet gear 106 engages the sun gear 107, so that when the sun gear 107 rotates in relation to the base 102, the planet gears 106 also rotate relative to the base 102 about a respective axis A4, A5, A6. A motor shaft 108 is fixed to the sun gear 107 along the axis A3 and is coupled to the motor 100 via a motor gear train 109.

Each finger 104 has an arcuate outer surface 104a that defines a portion of a circle, such that, when all of the fingers 104 are rotated to a radially inward position (FIGS. 7 and 10), the outer surfaces 104a of the fingers 104 form a stepped vertical cylinder, with their vertices 104b adjacent to one another. The fingers 104 can be rotated about their eccentric axes of rotation A4, A5, A6 (FIG. 11) so that their vertices 104b move radially outwardly from each other; rotation in this manner expands the circle defined by the radially outwardmost portions of the outer surfaces 104a of the fingers 104 (see FIGS. 8, 9 and 12). In operation, after the container of the desired size has been dispensed in one of the cups 88 as discussed above, the controller 42 signals the labeling carrier 68 to grasp the container. The carriage 92 slides on the support member 91, thereby moving the swing arm 94 to a height such that the lower ends of the fingers 104 are above the upper edge of the container. Also, the swing arm 94 pivots relative to the carriage 92 such that the fingers 104 are positioned directly over the container. At this point, the fingers 104 are rotated radially inwardly (FIGS. 7 and 10) to a retracted position. The carriage 92 then descends, which action lowers the fingers 104 into the cavity of the container. The motor 100 then exerts a torque on the sun gear 107 via the motor gear train 109 and the motor shaft 108, thereby causing the sun gear 107 to exert a torque on the planet gears 106 and a torque on the base 102 (via the planet gears 106 and finger shafts 105). Because the clutch 101 restrains the base 102 from rotating (via a pulley 101a and a belt 101b), the planet gears 106 rotate about axes A4, A5, A6 in response to this torque, causing the fingers 104 to turn and expand radially outward (see FIGS. 8 and 11) until they contact the inside surface of the container (see FIGS. 9 and 12). At this point, the container wall resists further expansion of the fingers 104, thereby inducing an opposing torque on the base 102 transmitted via the fingers 104, finger shafts 105, and planet gears 106. Once this opposing torque exceeds the frictional torque of the clutch 101, the base 102 and container—now held by the fingers 104—rotates about the axis A3. The clutch 101 continues to exert a restraining torque on the base 102 as the base 102 rotates. The fingers 104 continue to exert radially-outward force on the inside of the container (as explained above) as the base 102 rotates, thereby inducing the container to rotate and enabling the fingers 104 to lift the container from the cup 88. The controller 42 signals the carriage 92 to rise on the support member 91. As this occurs, the fingers 104 lift and carry the container from the cup 88, and the container continues to rotate relative to the body portion 98 due to the rotation of the base 102.

Other techniques for grasping and moving the container from the container dispensing station 58 will be apparent to those skilled in this art. For example, the gripping fingers may take a different configuration (e.g., they may not form a cylinder when rotated inwardly). As another example, gripping fingers may be used that grip the outer surface of the container. Alternatively, suction may be employed to temporarily grasp and move the container.

Once the labeling carrier 68 has retrieved the container from the cup 88, it carries the container to the labeling station 60 (see FIGS. 3 and 13-16). The labeling station 60 includes a printer 110 that is controlled by the controller 42. The printer 110, which is mounted to one side of the base 46, prints and presents an adhesive label that is to be affixed to the container. The labeling station 60 also includes a wiping device, such as the brush 112 illustrated in FIG. 8, that is positioned adjacent to the exit port 114 of the printer 110.

Figure 13:
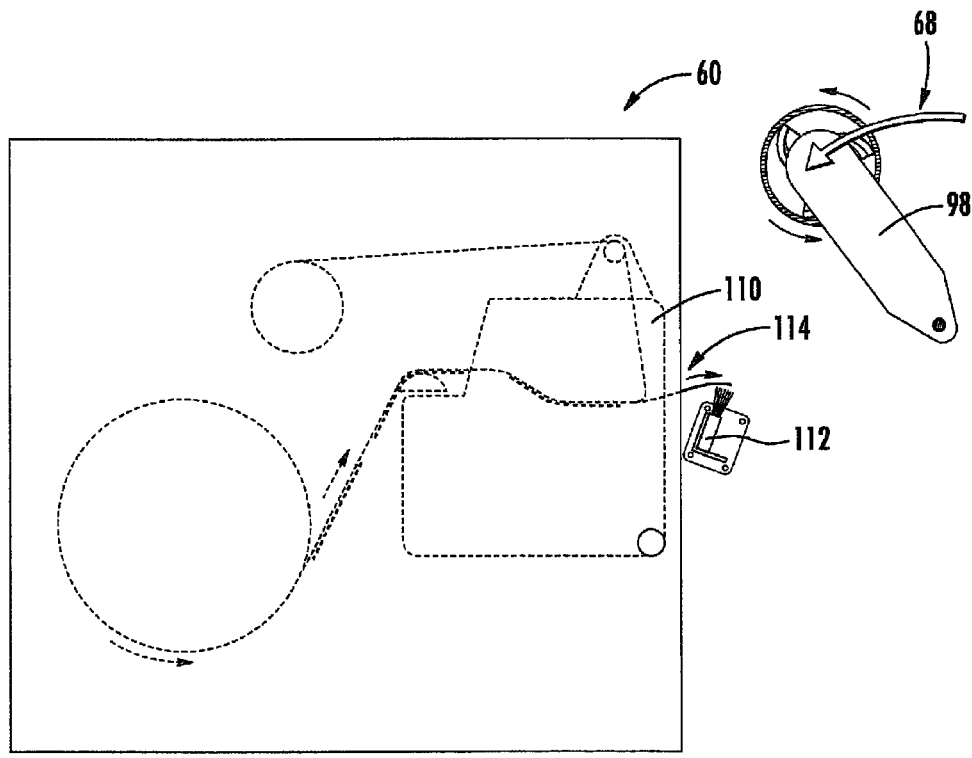
FIG. 13 is a schematic top view of the labeling station of the system of FIG. 2 prior to the application of a label on a container.
Figure 14:
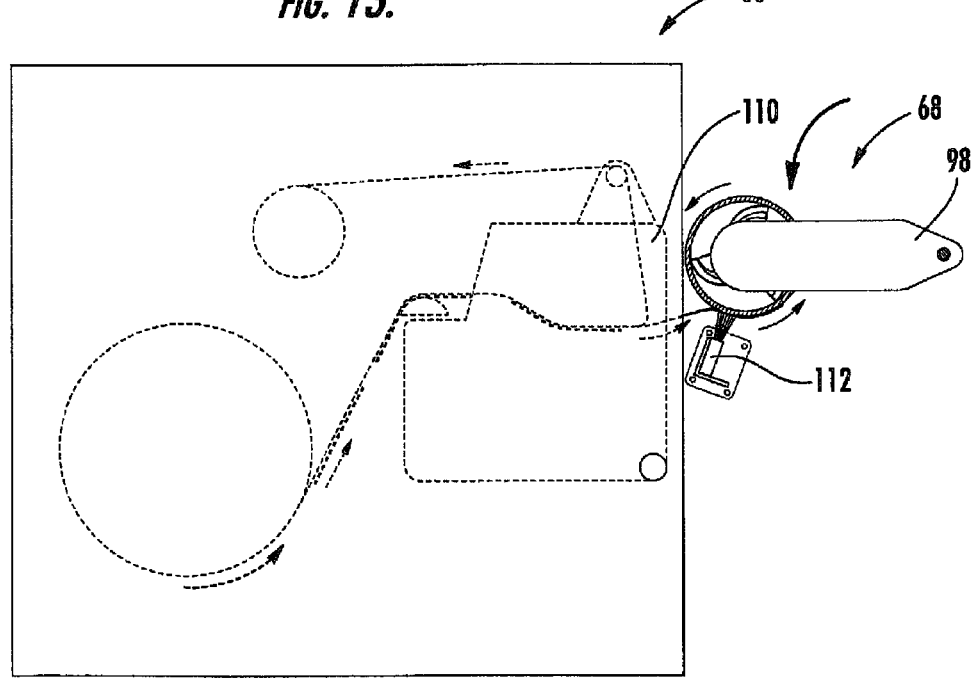
FIGS. 14-16 are schematic top views of the labeling station of FIG. 13 during the application of a label on a container as the container is held and rotated by the gripping unit of FIG. 7.
Figure 15:
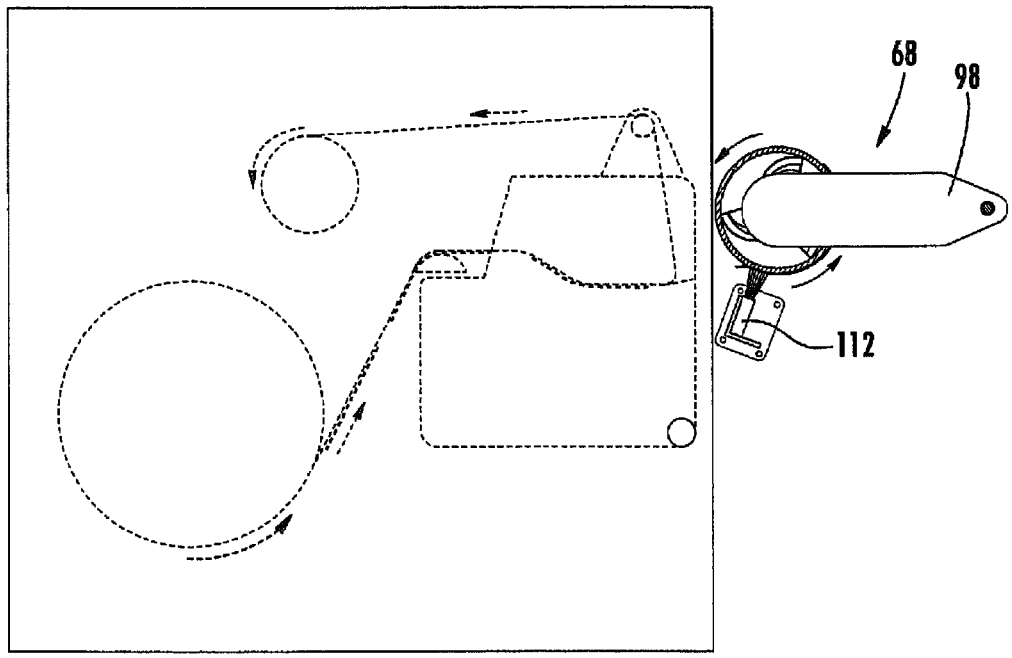
Figure 16:
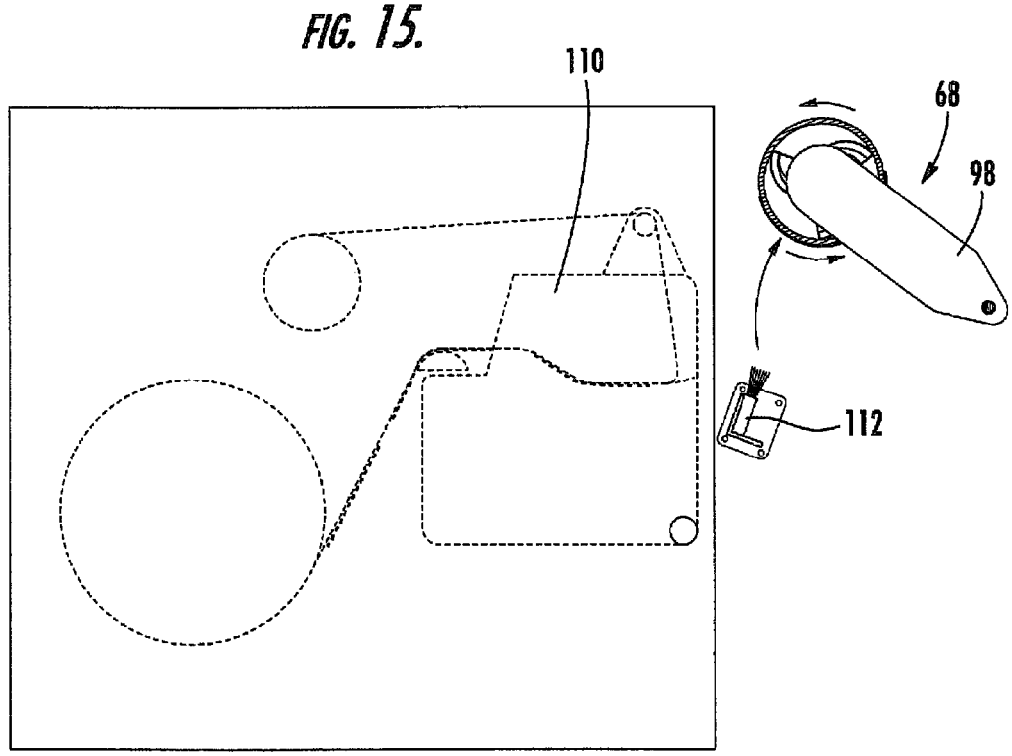

Returning to the operation of the system 40, once the container has been grasped and is being rotated by the labeling carrier 68, it is moved (under the direction of the controller 42) to the exit port 114 of the printer 110 through appropriate translation of the carriage 92 on the support member 91 and pivoting of the swing arm 94 relative to the carriage 92 (FIG. 13). Once the printed label has exited the exit port 114, the labeling carrier 68 presents the rotating container to the label (FIG. 13); the rotation of the container enables the wiping device to smoothly apply the label to the container (augmented by the brush 112—see FIGS. 14-16).

Those skilled in this art will appreciate that other structures and components for affixing a printed label to a container may also be employed with the present invention. For example, the container may be transferred to pinch rollers located at the exit port 114.

Figure 17A:
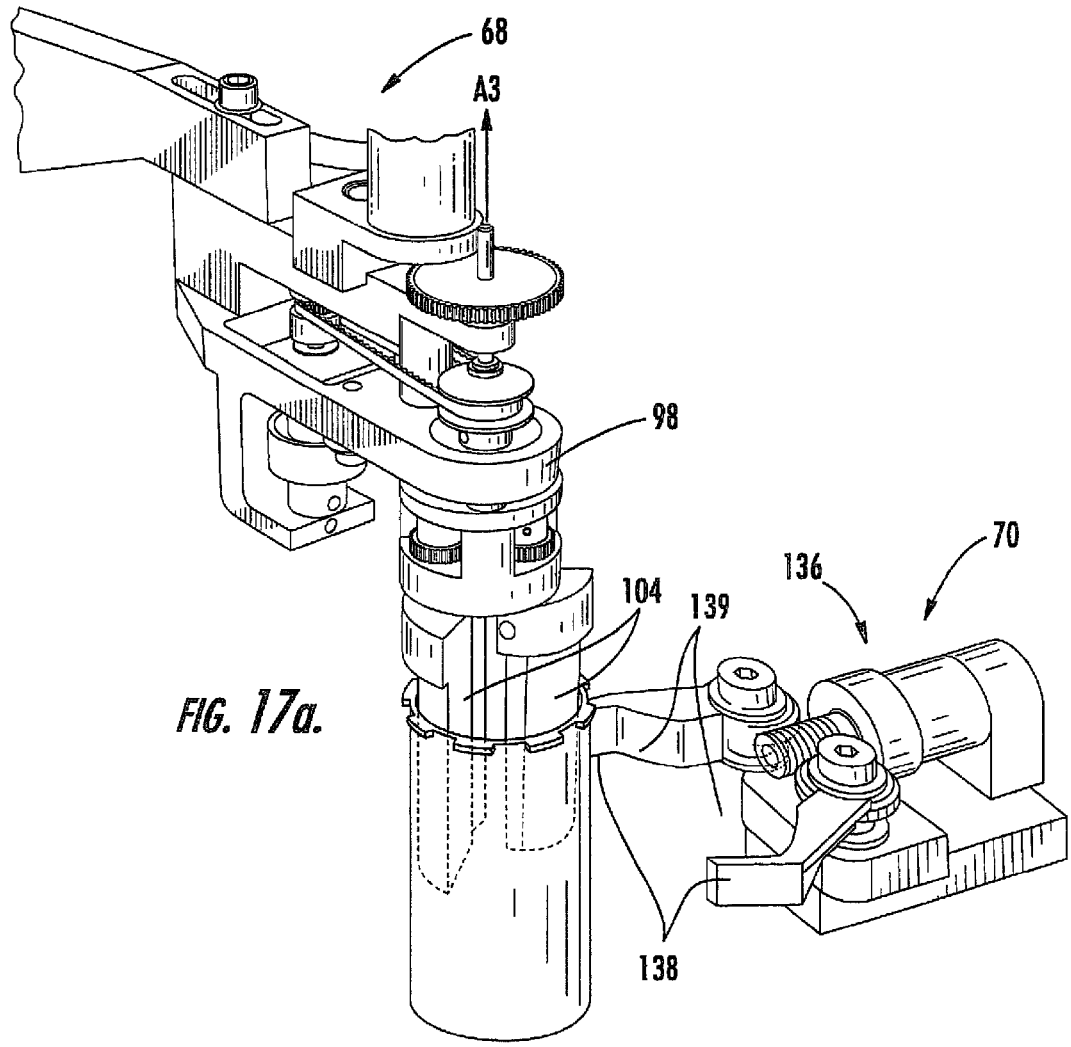
FIGS. 17a-17c are enlarged perspective views of the transfer of a container from the labeling carrier of FIG. 7 to the dispensing carrier of the system of FIG. 2.
Figure 17B:
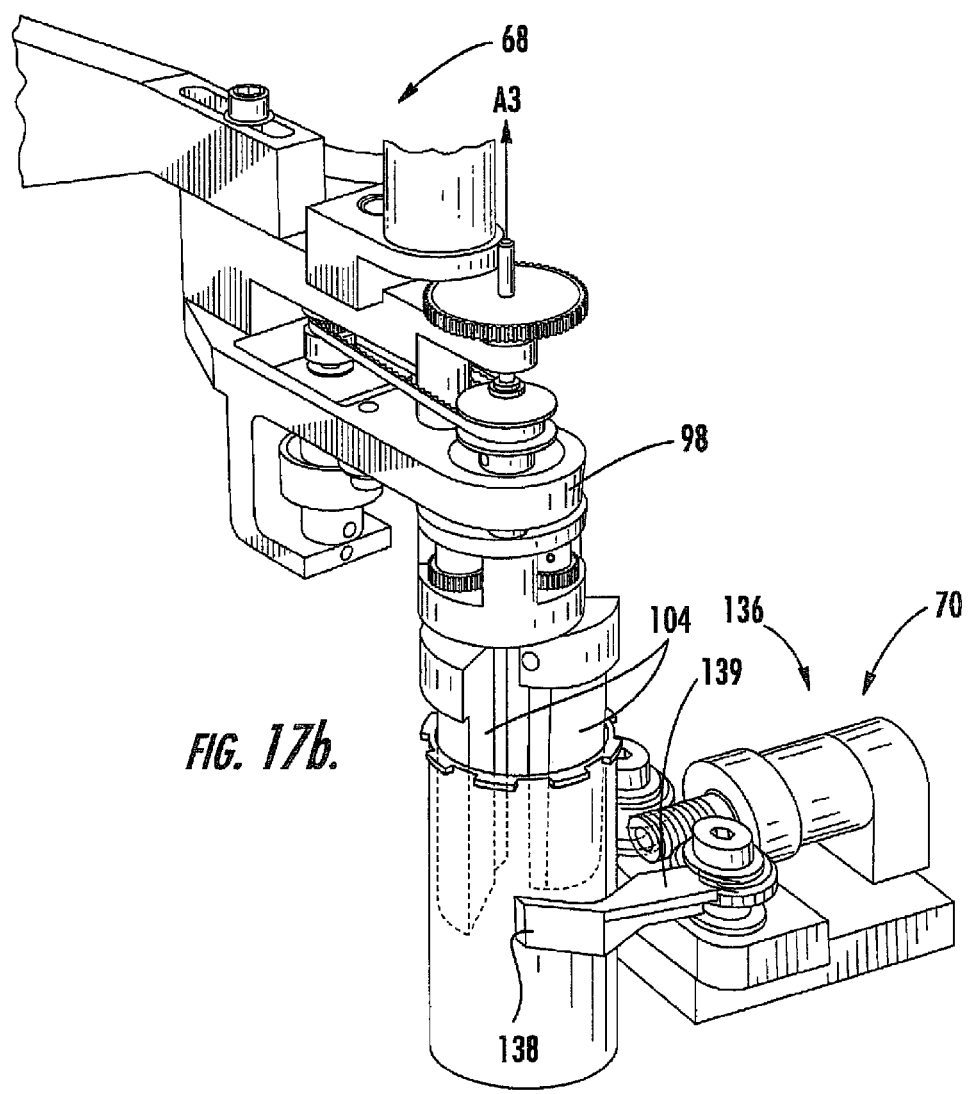
Figure 17C:
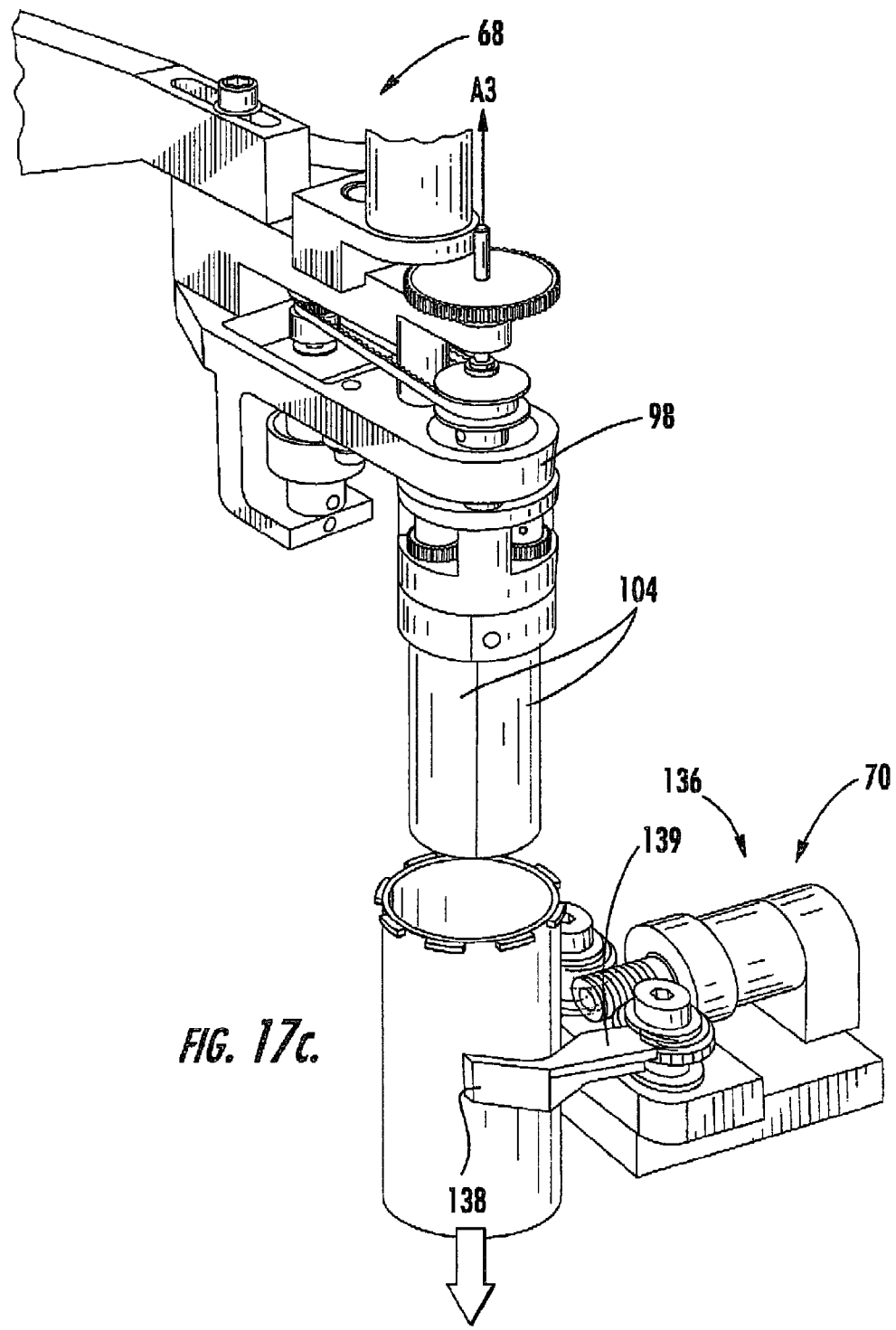
Figure 18:
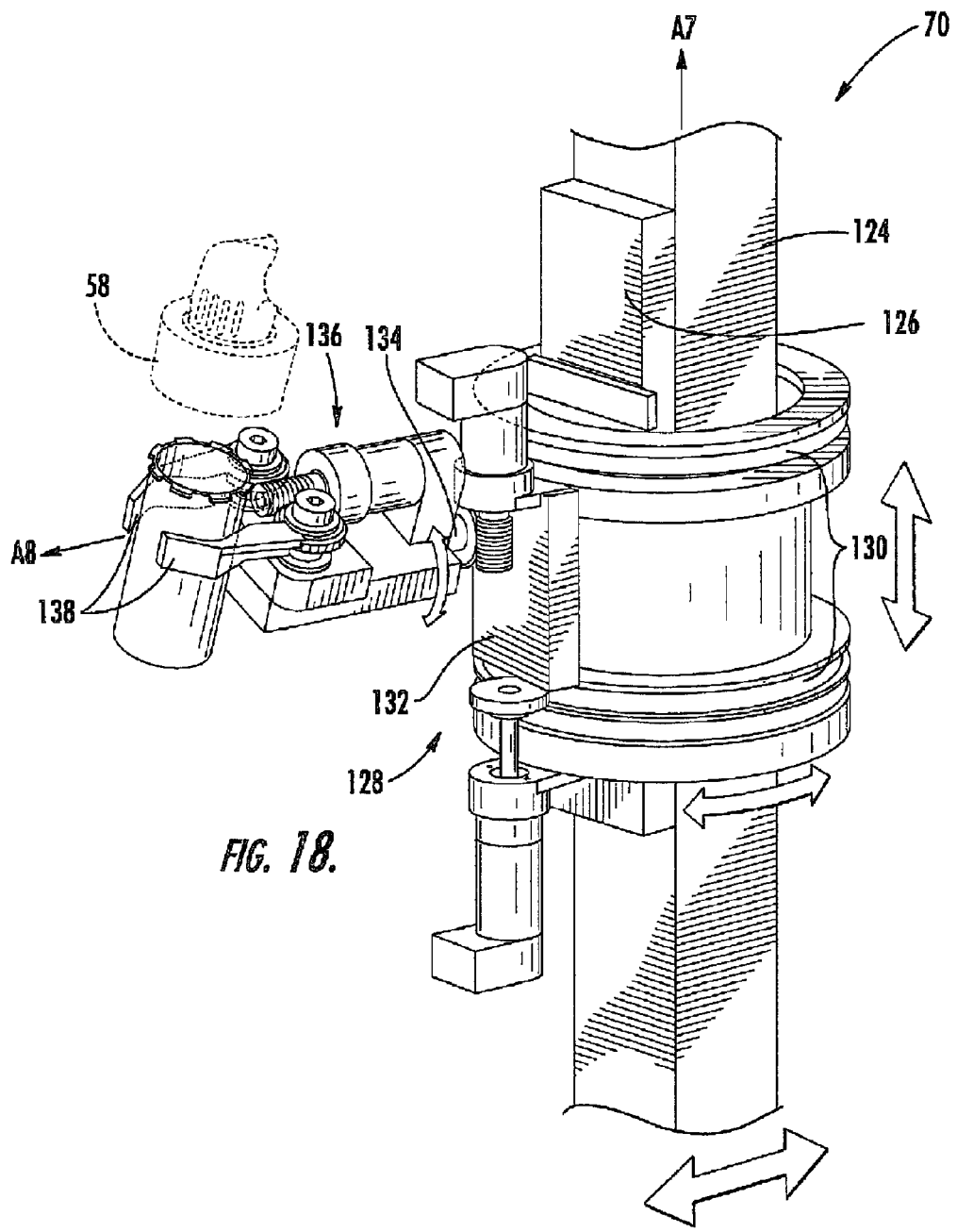
FIG. 18 is an enlarged perspective view of the lower carriage and the grip unit of the dispensing carrier of FIG. 17 illustrating that the lower carriage can be moved vertically and horizontally and that the grip unit can be rotated about two axes.
Figure 19:
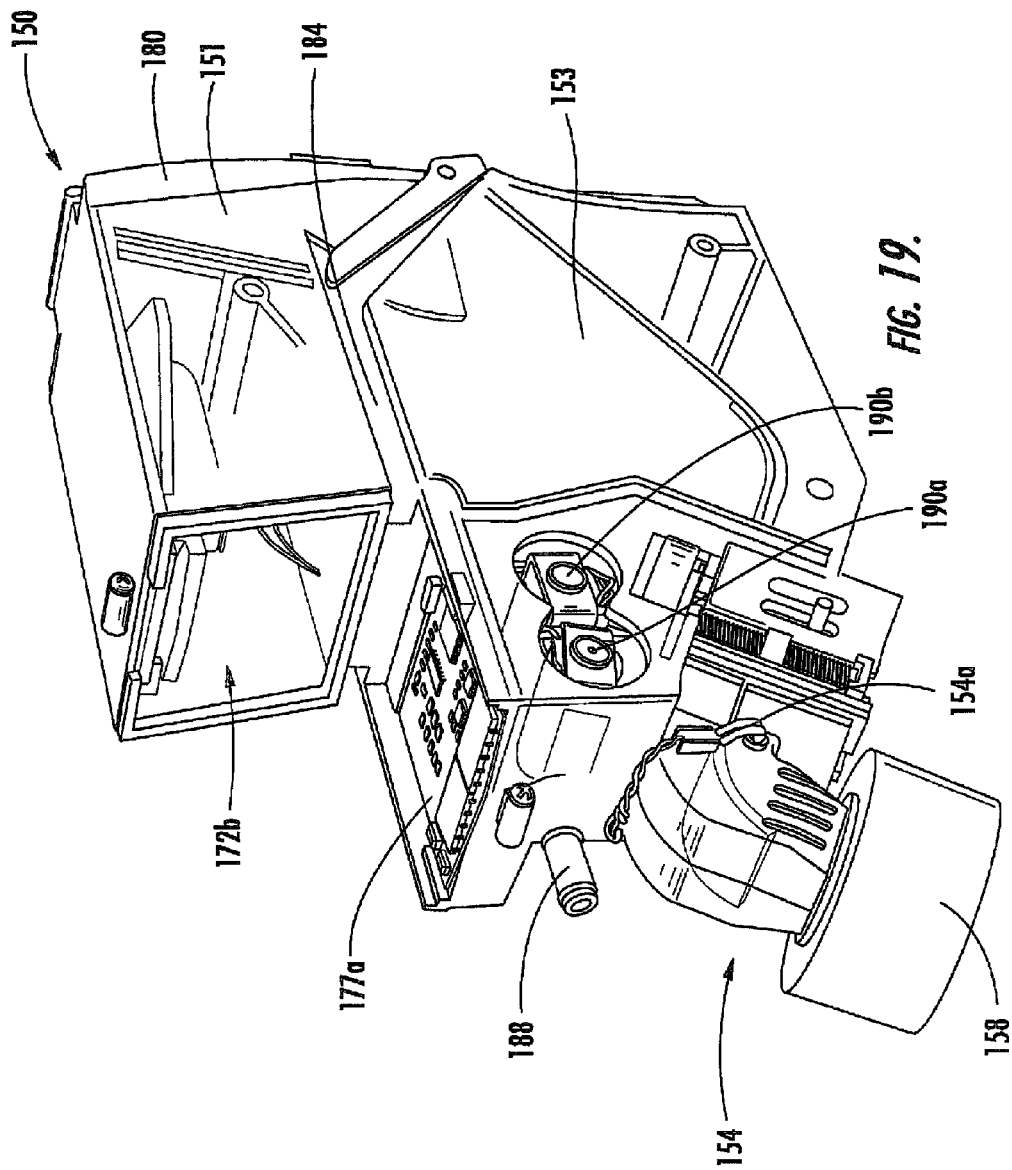
FIG. 19 is an enlarged perspective view of a dispensing bin employed in the system of FIG. 2.

After the container has been labeled, the labeling carrier 68 moves to a transfer position (through appropriate movements of the carriage 92, swing arm 94, and body portion 98, as directed by the controller 42) and transfers the labeled container to the dispensing carrier 70 (FIGS. 3, 17 and 18). The dispensing carrier 70 includes an upper carriage 120 that slides upon a rail 122 extending between the cross-members 52, a rail 124 that extends downwardly from the carriage 120, a lower carriage 126 that slides vertically along the rail 124, and a grip unit 128 that is mounted on the lower carriage 126 via horizontally disposed circular tracks 130 that revolve around the lower carriage 126. The grip unit 128 includes a traveler unit 132 that is mounted to the tracks 130, an axle 134 that is rotatably mounted in and extends from the traveler unit 132, and a gripping mechanism 136 that is attached to and is rotatable with the axle 134. The gripping mechanism 136 has two jaws 138 that can confront each other and exert clamping force on an object (such as a container of the type discussed herein). Notably, the jaws 138 have a curved portion 139 that assists in gripping the cylindrical container. Also, the jaws 138 may be configured such that they compress the container only to a desired torque level (e.g. with a clutch mechanism, or with a sensor that detects a predetermined current level for the drive motor) in order to prevent crushing of the container, or such that they compress only to predetermined positions selected to match the sizes of the different containers used with the system 40.

The dispensing carrier 70 has the capability of moving the gripping mechanism 136 (and, in turn, an object grasped therein) to designated locations within the cavity 45 of the frame 44. Movement from end to end within the cavity 45 (i.e., toward and away from the arches 54, 55, 56) is accomplished by inducing movement of the upper carriage 120 on the rail 122. Vertical movement is accomplished by inducing movement of the lower carriage 126 on the rail 124. The grip unit 128 may also revolve around the rail 124 about an axis A7 through revolution of the tracks 130 around the carriage 126. The gripping mechanism 136 may rotate relative to the traveler unit 132 about an axis A8 defined by the axle 134. Induction and control of these movements may be achieved through conventional robotic techniques that need not be described in detail herein. The skilled artisan will also appreciate that other components for grasping and maneuvering a container may also be employed with the present invention.

Returning to operation of the system 40, transfer of the labeled container from the labeling carrier 68 to the dispensing carrier 70 is achieved by the controller 42 directing the dispensing carrier 70 to move the gripping mechanism 136 to a position in which the jaws 138 can clamp onto the outer surface of the container as it is presented by the labeling carrier 68. Preferably, the position for transfer is proximate to the printer 110 and the tablet dispensing station 62. The controller 42 first signals the dispensing carrier 70 to close the jaws 138 onto the outer surface of the container, then directs the labeling carrier 68 to retract the fingers 104 to their radially inward positions so that the container is held only by the jaws 138. The fingers 104 are then withdrawn from the container (through either upward movement of the fingers 104 by the labeling carrier 68 or downward movement of the labeled container by the dispensing container 70), and the labeled container is ready to be filled with tablets.

Filling of labeled containers with tablets is carried out by the tablet dispensing station 62 (see FIGS. 2 and 19-29). The tablet dispensing station 62 comprises a plurality of tablet dispensing bins 150, each of which holds a bulk supply of individual tablets (typically the bins 150 will hold different tablets). The dispensing bins 150, which are typically substantially identical in size and configuration, are organized in an array mounted on the intermediate rails 53 of the frame 44, and each has a dispensing channel 154 with an outlet that faces generally in the same direction, to create an access region for the dispensing carrier 70. The identity of the tablets in each bins is known by the controller 42, which can direct the dispensing carrier 70 to transport the container to the proper bin 150. In some embodiments, the bins 150 may be labeled with a bar code or other indicia to allow the dispensing carrier 70 to confirm that it has arrived at the proper bin 150.

The dispensing bins 150 are configured to singulate, count, and dispense the tablets contained therein, with the operation of the bins 150 and the counting of the tablets being controlled by the controller 42. Some embodiments may employ the controller 42 as the device which monitors the locations and contents of the bins 150; others may employ the controller 42 to monitor the locations of the bins, with the bins 150 including indicia (such as a bar code or electronic transmitter) to identify the contents to the controller 42; in still other embodiments the bins 150 may generate and provide location and content information to the controller 42, with the result that the bins 150 may be moved to different positions on the frame 42 without the need for manual modification of the controller 42 (i.e., the bins 150 will update the controller 42 automatically).

Any of a number of dispensing units that singulate and count discrete objects may be employed; however, dispensing units that rely upon targeted air flow and a singulating nozzle assembly, such as the devices described in co-pending U.S. patent application Ser. No. 09/934,940, filed Aug. 22, 2001 and entitled DEVICE TO COUNT AND DISPENSE ARTICLES and in U.S. Provisional Application No. 60/306,782, filed Jul. 20, 2001 for DEVICE TO COUNT AND DISPENSE ARTICLES, are preferred (these applications are hereby incorporated herein by reference in their entireties). Bins of this variety may also include additional features, such as those described below.

Referring now to FIGS. 19 and 23-29, the bins 150 can be described generally as having a tablet-filled hopper 153 through which air flows and agitates the tablets contained therein, and the aforementioned dispensing channel 154 through which the tablets are dispensed one at a time. Suction can be applied to the channel 154 through a forwardly-directed jet 155; a rearwardly-directed jet 156 is also included that can reverse the motion of tablets within the channel 154. The jets 155, 156 are controlled by the controller 42, which initiates forward air flow in response to a customer order and activates rearward air flow in response to the passage of a certain quantity of tablets through in the dispensing channel 154 (as detected by a counting sensor 154a located in the dispensing channel 154). Alternatively, the jets 155, 156 may be controlled by a local controller unique to each bin 150 (as described in some detail below). The bins 150 can filled or replenished with tablets via access from a pivoting door 180 located at the upper rear portion of the bin 150. Notably, the location of the door 180 opposite the outlet of the dispensing channel 154 enables an operator to replenish the bin 150 without disconnecting it from the frame 44 or interfering with the dispensing from this or another bin 150. Also, the pivoting of the lower end portion of the door 180 and the inclusion of side walls 180a causes an open door 180 to form a funnel-like configuration, which configuration can facilitate pouring of pharmaceuticals into the bin 150.

Referring now to FIGS. 20A through 22, the bins 150 may include components that permit the entry to the dispensing channel 154 to be adjusted in size to complement the size and configuration of the tablet to be dispensed. This can be achieved through a stationary wall 160, a moveable wall 161, a moveable ceiling 162 and a moveable floor 163 that form the entry to (and in some instances the perimeter of) the dispensing channel 154. In the illustrated embodiment, the stationary wall 160 is a portion 151a of the housing 151 of the bin 150. The stationary wall 160 also forms a portion of a recess 301 that extends inwardly into the housing 151. The ceiling 162 is part of a ceiling unit 302 that fits within the recess 301. The ceiling unit 302 also includes a vertical panel 304 extends downwardly from a lateral edge of the ceiling 162. The vertical panel 304 includes two apertures and an engagement projection 306 that engages a slot in a wall of the recess 301. Also, an adjustment knob 320 and attached threaded shank 322 insert through a threaded nut 324 attached to the vertical panel 304; the knob 320 is held in place within a recess in the housing 151. The moveable wall 161 is part of a moveable wall unit 308 that includes front and rear panels 310, 312 that extend transversely from front and rear portions of the moveable wall 161. Two posts 314 extend from the moveable wall 161 and pass through the apertures of the vertical panel 304 of the ceiling unit 302 into elongated slots 316 of the housing. A front projection 318 extends beyond the front panel 310 and is received in a slot 319 in the housing. The moveable floor 163 is part of a floor unit 326 that also includes a front portion 328 with a slot 330 that receives the front projection 318 of the moveable wall 161, gussets 331, 332, 333 that help to guide the moveable wall 161, and an adjustment knob 334 and an attached threaded shank 336 that extend into and through an attached nut 338. The adjustment knob 334 is maintained in place within a slot 340 in the housing of the bin 150, and the floor 163 is maintained in vertical position by two tines 342. Two springs 344 surround the posts 314 between the moveable wall 161 and the vertical panel 304.

In addition, the floor 163 includes a series of apertures 349 located to the side of the dispensing channel 154. These apertures 349 can provide additional flow to this region of the bin 150. The additional flow can encourage tablets that tumble to a position adjacent the dispensing channel 154 during agitation to rejoin the remaining tablets; otherwise, they may remain in this "dead" area, which can tend to clog entry into the dispensing channel 154.

To adjust the width of the dispensing channel 154 (FIG. 22), the adjustment knob 334 is rotated about its axis. Rotation of the shank 336 within the nut 338 induces the floor 163 to slide horizontally between the housing 151 and the tines 342. In doing so, the posts 314 are free to slide through the apertures in the vertical panel 304; the moveable wall 161 is maintained in contact with the floor 163 by compression from the springs 344. In the illustrated embodiment, the exact position of the moveable wall 161 can be monitored with markings 346 located on the rear portion of the floor 163.

To adjust the height of the ceiling 162 (FIG. 21), the adjustment knob 320 is rotated. Interaction between the shank 322 and the nut 324 causes the ceiling unit 302 to slide within the recess 301. The posts 314 slide within the slots 316 in the housing 151, and the moveable wall 161 is driven upwardly or downwardly by the ceiling 162. The front projection 318 of the moveable wall 161 remains in the slots 319, 330. The exact position of the ceiling 162 can be monitored with markings 348 located on the side of the housing 151.

Notably, the configuration of the dispensing channel 154 described above can provide an essentially "gapless" channel for the tablets to travel in, which can improve performance of the system 40. Also, the floor 163 and the stationary wall 160 of the dispensing channel 154 remain in place, which provides a constant location to which the container receiving tablets can be delivered.

A further optional feature of the illustrated dispensing channel 154 is a splash guard 158 (FIG. 28), which is located at the outlet of the dispensing channel 154. The splash guard 158 can reduce or eliminate the risk that a tablet traveling to the container falls or bounces outside the container. In one embodiment, the splash guard 158 is formed of a spongy foam material (such as polyethylene foam); such a material enables the container to be compressed against the splash guard 158, causing it to deform around the upper edge of the container and seal it so that tablets do not stray from the container. With a splash guard of this construction, the presentation of the container to the dispensing channel 154 by the dispensing carrier 70 can occur with a larger margin for error in positioning.

Another feature of the tablet dispensing station 62 that may be included with the present invention is illustrated in FIGS. 3 and 23-25. As can be seen therein, a low pressure manifold 170 having a number of inlets 171 is mounted to the frame 44 and extends horizontally; the manifold 170, which is fluidly connected to a low pressure source such as a vacuum motor (not shown), provides low level (i.e., about 2 psi) suction to the bin 150 to either (a) maintain a door 172 in a closed position when the particular bin 150 is not in use or (b) agitate tablets within the bin when the door 172 is opened by a solenoid 173 or other actuating unit within the bin 150. Of course, individual blowers may be used for each bin in lieu of the manifold 170 with multiple inlets 171. Also, a high pressure (i.e., about 30 psi) conduit 175 with a fitting 176 also extends horizontally from its mounting point on the frame 44, with the fitting 176 projecting toward the bin 150. The fitting 176 may be a check valve, so that high pressure air is not expelled if the bin 150 is not present. The high pressure conduit 175 is fluidly connected to a high pressure source (not shown). Further, a connector circuit board 177 is mounted horizontally below the manifold 170; the circuit board 177 or other electrical connector provides an electrical connection between the controller 42 and the bin-controlling circuit board 177a (or other electronic component) of the bin 150 for power and data signals from the controller 42, such as those that control the opening and closing of the door 172, the application of suction and/or positive pressure through the conduit 175, and the counting sensor 154a. Thus, all three of these connections should be made for the bin 150 to operate.

Despite the presence of the hopper door 180 through which the hopper 153 can be refilled, there are instances for which it would be desirable to remove the bin 150 from the frame 44 (for example, to adjust the size of the entry to the dispensing channel 154). When the bin 150 has been removed, reinstallation requires that connections be re-established between the bin 150 and the manifold 170, the conduit 175, and the connector circuit board 177.

The frame 44 illustrated herein includes prongs 183 (FIG. 23) that facilitate re-establishment of the aforementioned connections. The prongs 183 are positioned below the manifold 170 and are configured for slidable movement with slots 184 on the housing 151 that receives the prongs 183. The prongs 183 include recesses 183a that receive pins 187 located on a pivoting member 189. As the prongs 183 slide to completely fill the slots 184, an opening 172*b* of the housing 151 aligns with an inlet 171 of the manifold 170, the bin-controlling circuit board 177*a* located on the front edge of the hopper 153 comes into contact with the connector circuit board 177, and a fitting 188 that extends from the front of the housing 151 below the bin-controlling circuit board 177*a* locks with the fitting 176 of the conduit 175. As such, simply sliding the bin 150 back into place (FIGS. 23 and 24) can re-establish all of these operative connections without additional steps. The bin 150 can be secured firmly into place by pivoting the member 189 so that the posts 187 fill the slots 183*a* (FIGS. 24 and 25).

Figure 23A:
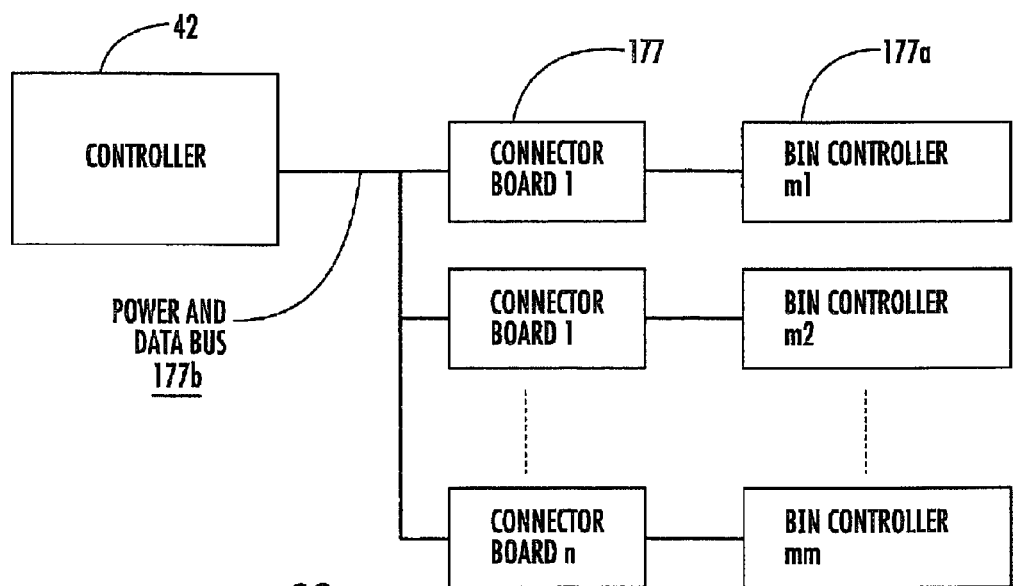
FIG. 23A is a schematic diagram of the controller and three exemplary connector boards from the frame and three exemplary bin-controlling circuit boards.

Referring now to FIG. 23A, the connector board 177 is mounted to the frame 44 and supports electronic circuitry which contains a "location identifier" unique to the physical location of the connector board 177 on the frame 44. The connector board 177 provides its mating bin-controlling circuit board 177*a* with regulated and unregulated power, a physical connection to the data bus 177*b*, and the location identifier for the connector board 177. The connector board 177 communicates power and data to the bin-controlling circuit board 177*a* via the bus 177*b* (which is a power and data bus).

Still referring to FIG. 23A, the bin-controlling circuit board 177*a* contains a "bin identifier" unique to that bin that can be read by the controller 42. The bin-controlling circuit board 177*a* processes counting and dispensing functions such as triggering the solenoid 173, triggering the air valves 190, and processing signals from the sensor 154*a*. The bin-controlling circuit board 177*a* can receive dispense instructions and communicate its unique identifier and other information relative to its counting function, such as count status, empty condition, and the like. In some embodiments the bin-controlling circuit board 177*a* may also send or receive data such as inventory levels or sensor condition. Upon command from the controller 42 the bin controlling circuit board 177*a* can initiate and control the dispense and count process.

With this configuration, the controller 42 can search for a unique bin identifier and associate it with a certain location identifier. The controller 42 may then direct the dispensing carrier 70 to carry the container to the appropriate position for dispensing. Thus, once a pharmaceutical has been associated with a particular bin 150 via its "bin identifier", accurate dispensing of the pharmaceutical becomes independent of a priori knowledge of the pharmaceutical's physical location on the frame 44. This gives the user the ability to quickly re-arrange the bin locations according to changing requirements such as alphabetization or utilization ranking.

Figure 23B:
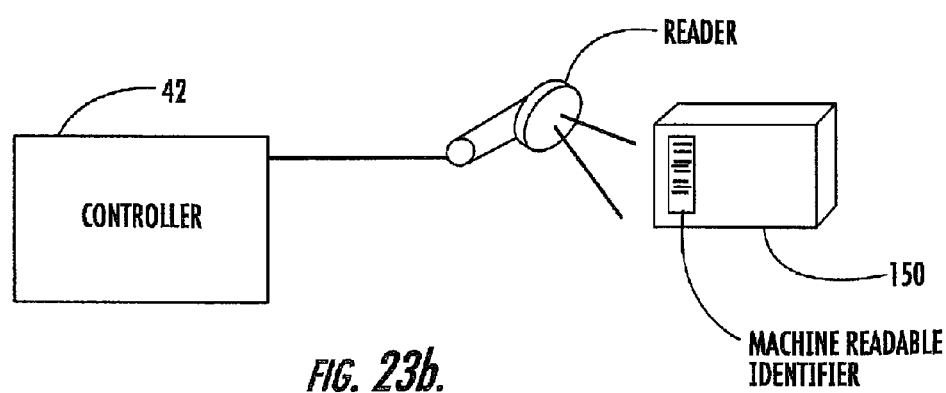
FIG. 23B is a schematic diagram of another embodiment of the controller of the system of FIG. 2.
Figure 26:
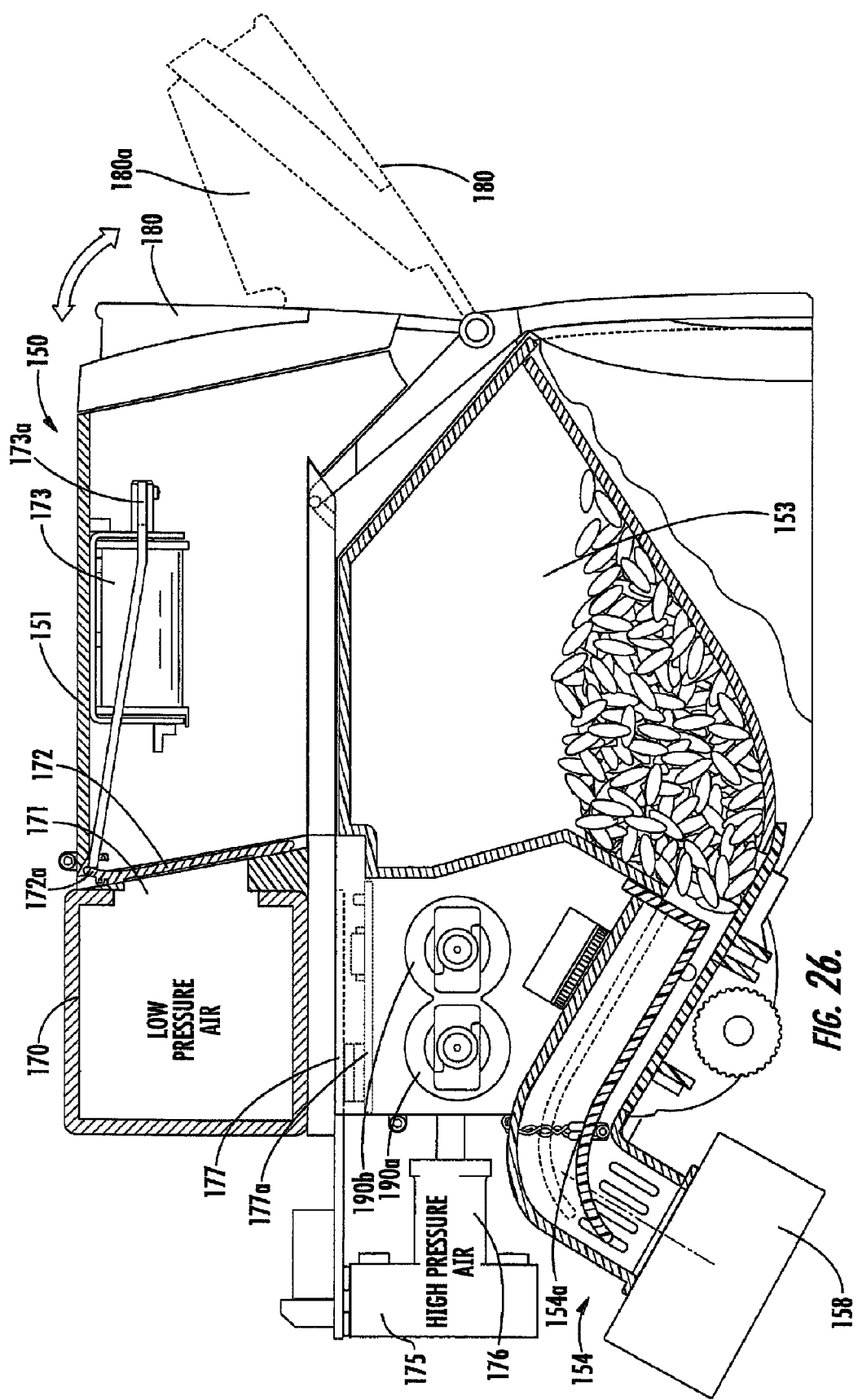
FIG. 26 is an enlarged section view of the assembled dispensing bin and frame of FIG. 24 with tablets loaded into the bin.

Referring now to FIG. 23B, in other embodiments of the system 42, each bin 150 may contain an additional machine readable identifier 150*a* which is more readily accessible to an operator wielding a reader 150 *b* which is connected to the controller 42. Using this reader 150*b*, the operator may select and read the bin identifier 150*a* to automatically associate various external data such as pharmaceutical identifiers, replenishment quantities, etc., to the bins' information set. This identifier 150*a* may be placed on the inside of the replenishment door 180 so that the door 180 must be opened before the reader can access the identifier 150*a*.

Figure 27:
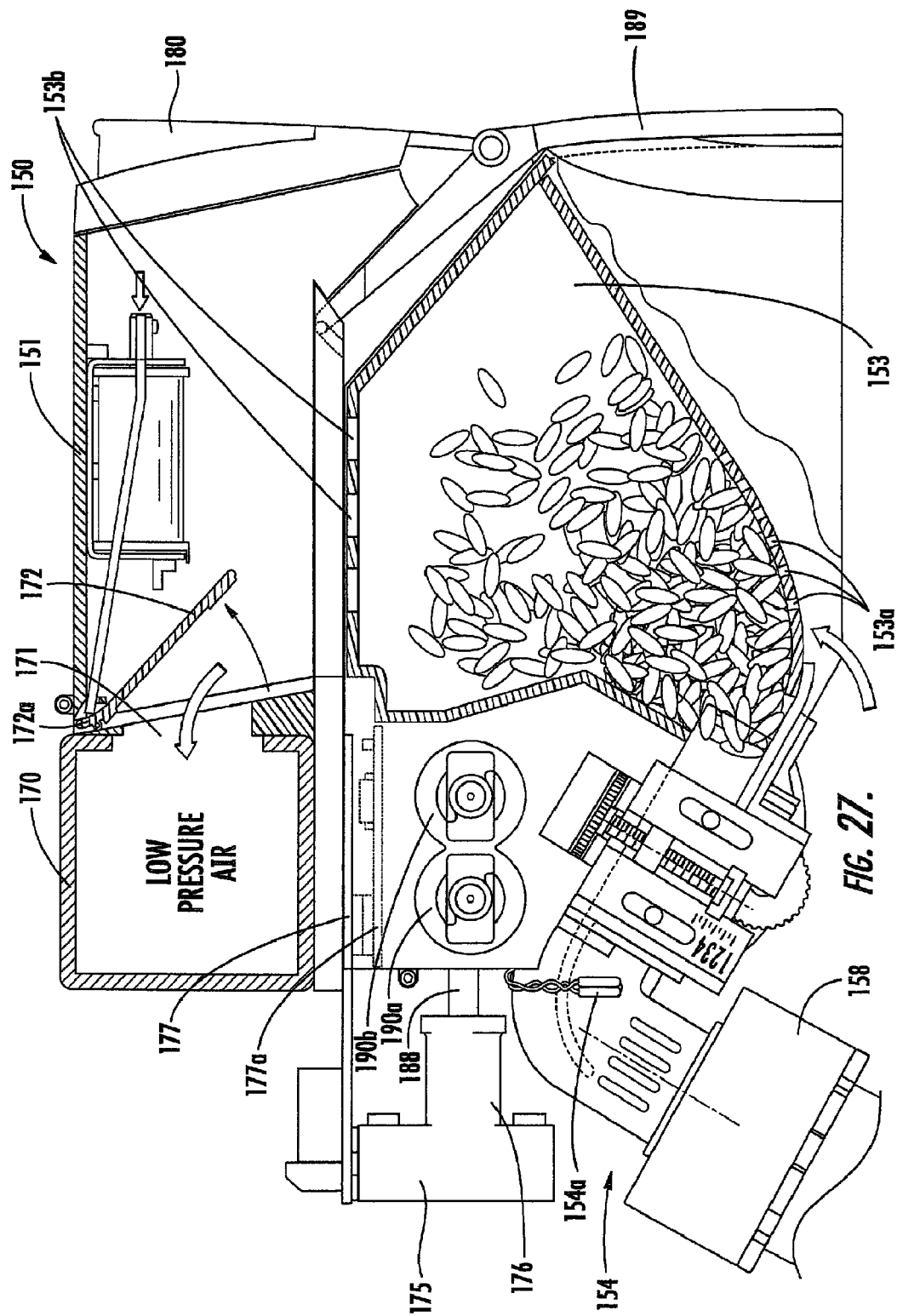
FIG. 27 is an enlarged section view of the assembled dispensing bin and frame of FIG. 24 with tablets being agitated by low pressure air flowing upwardly through the bin.
Figure 28:
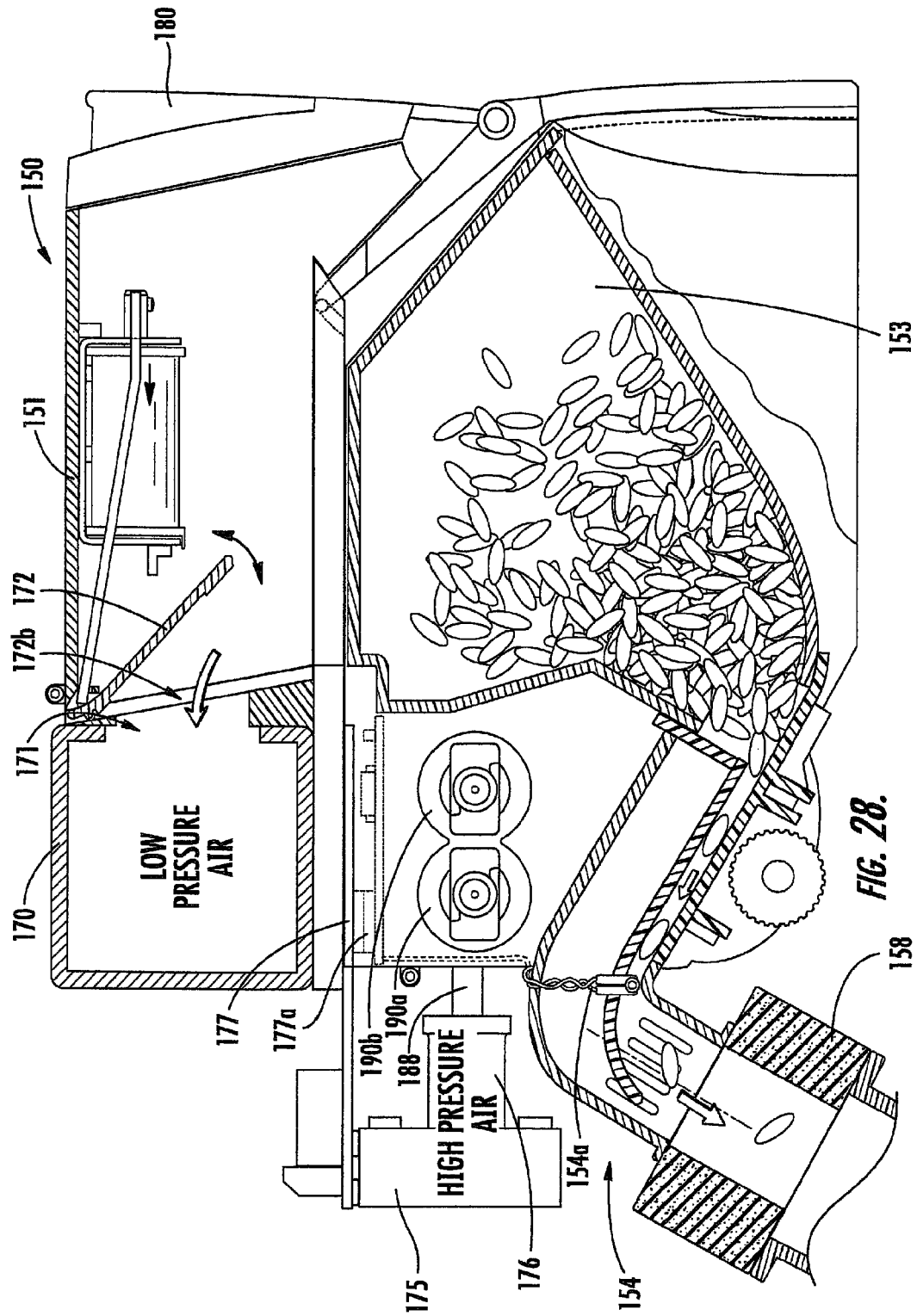
FIG. 28 is an enlarged section view of the assembled dispensing bin and frame of FIG. 24 with high pressure air being applied to the dispensing channel, such that tablets are drawn therein in single file in a lengthwise orientation.

To fill the container, the dispensing carrier 70, directed by the controller 42, moves the container to the exit port of the selected dispensing bin 150. The controller 42 signals the solenoid 173 to open the door 172 (more specifically, the solenoid 173 retracts, and a plunger 173*a* moves toward the door 172, striking a finger 172*a* located on the top portion of the door 172 and causing it to pivot open—see FIG. 27). This opening of the door 172 draws low pressure air up through the hopper 153 from a screen 153*a* on the bottom of the hopper 153, through another screen 153*b* on the top portion of the hopper 153, and to the opening 172*b*, thereby agitating the tablets contained in the hopper 153 (FIG. 27). Once agitation has commenced, the controller 42 signals a valve 190*a* connected with the forwardly-directed jets to open, which causes high pressure air to be drawn outwardly through the dispensing channel 154 (FIG. 28). Tablets are oriented into a preferred orientation by the shape of the entry to the dispensing channel 154 and dispensed into the container through the dispensing channel 154. The counting sensor 154*a* counts the tablets as they pass through a predetermined point in the dispensing channel 154. Once dispensing is complete (i.e., a predetermined number of tablets has been dispensed), the controller 42 activates the valve 190*b* associated with the rearwardly-directed jet 56 and deactivates the dispensing bin 150, the solenoid 173 deactivates, thereby closing the door 172 (FIG. 29), and the dispensing carrier 70 moves the filled container to the closure dispensing station 64.

Figure 29:
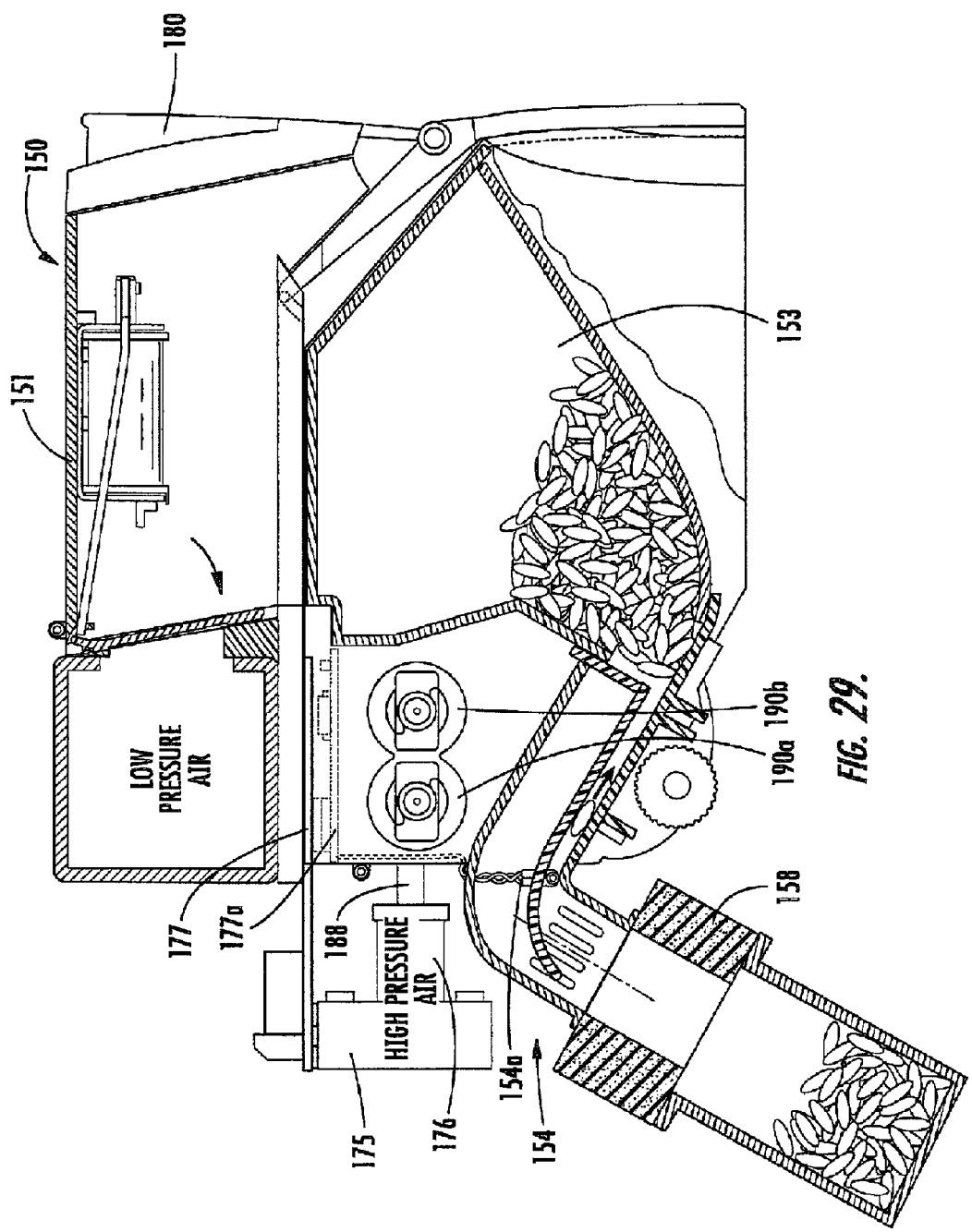
FIG. 29 is an enlarged section view of the assembled dispensing bin and frame of FIG. 24 with a desired number of tablets dispensed into the container.
Figure 29A:
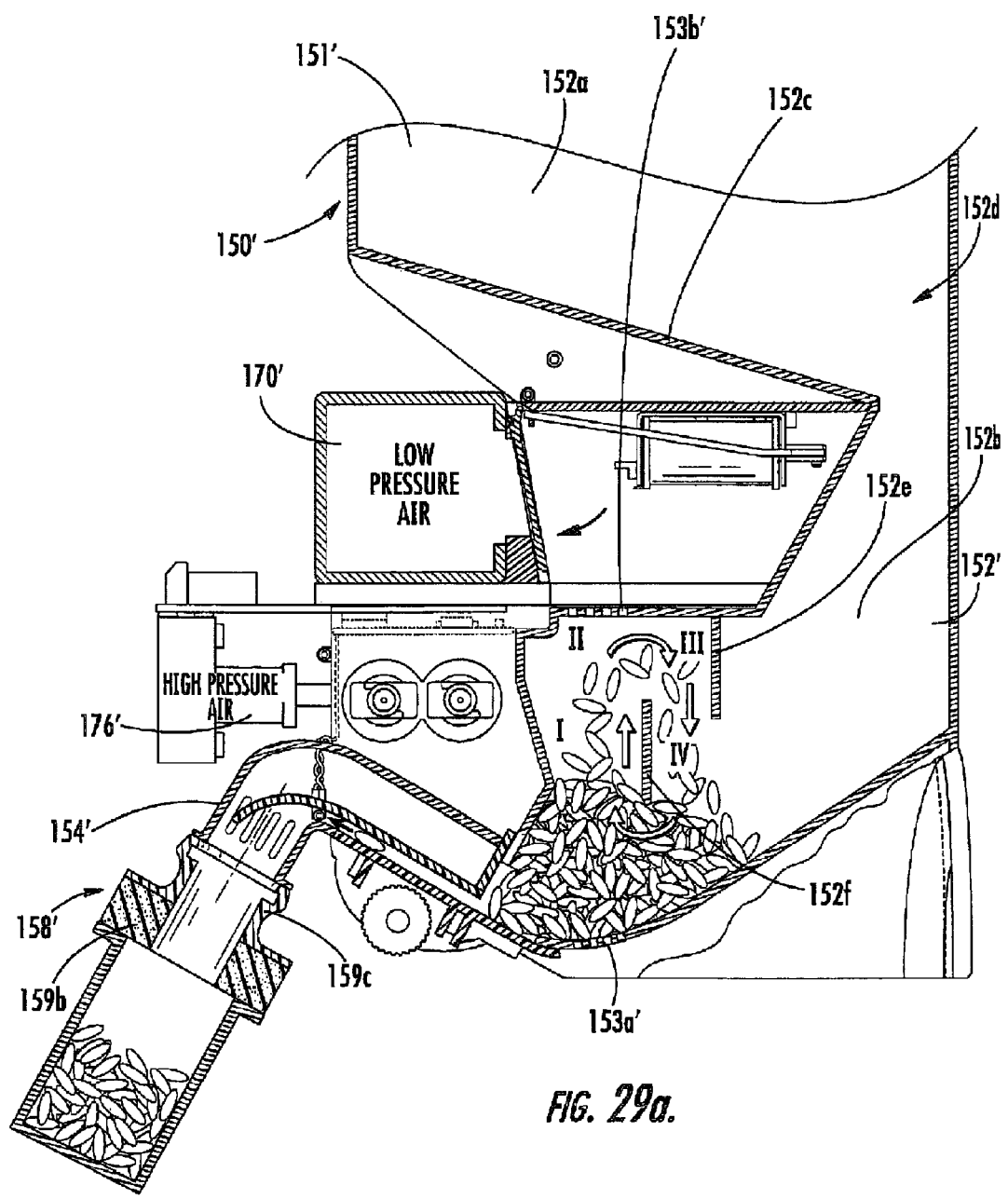
FIG. 29a is a partial side section view of a dispensing bin according to alternative embodiments of the present invention.
Figure 29B:
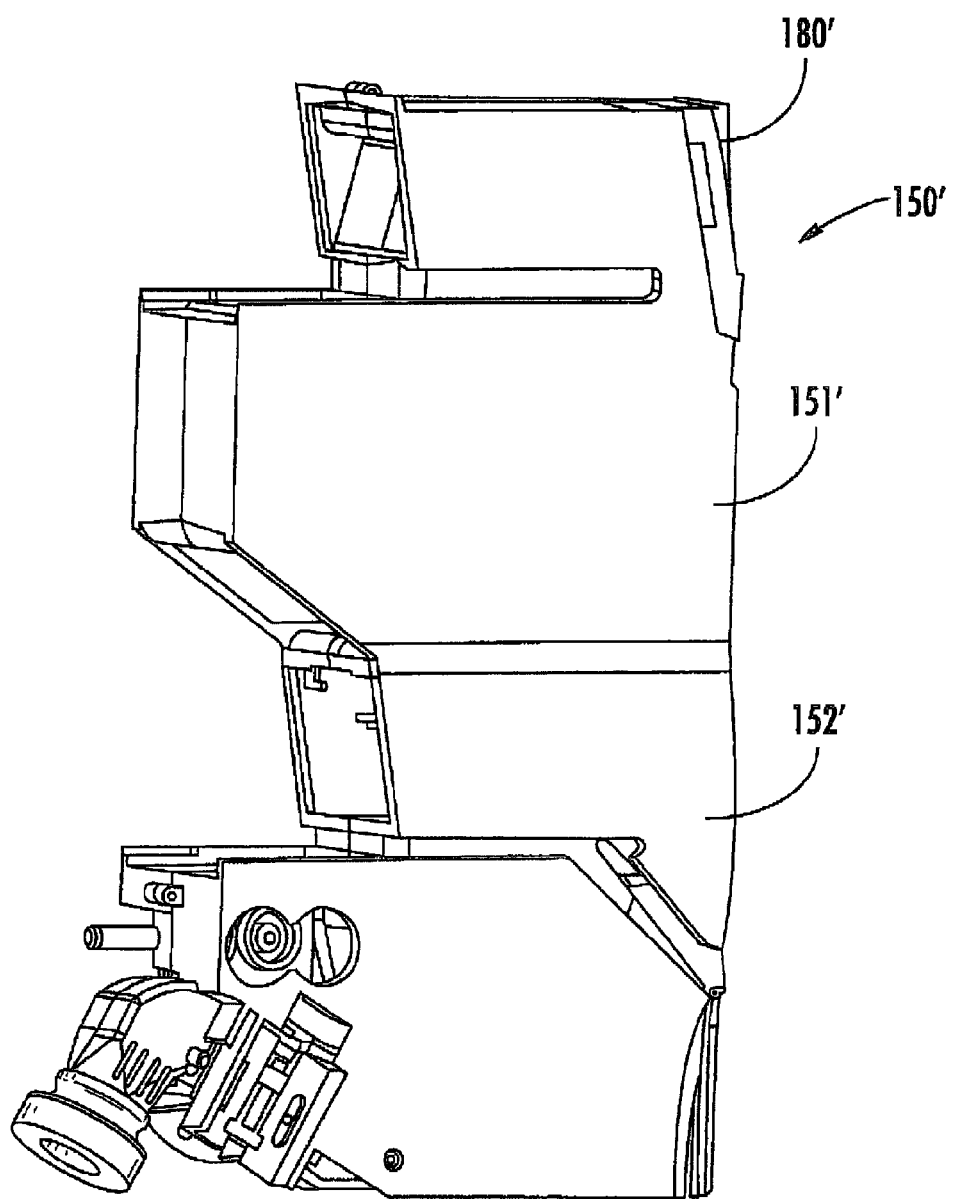

Referring now to FIGS. 29*a* and 29*b*, an alternative embodiment of a dispensing bin, designated broadly at 150', is illustrated therein. The dispensing bin 150' is attached to a low pressure manifold 170' in the manner of the dispensing bin 150 described above and dispenses tablets through a dispensing channel 154' with the assistance of air drawn through a high pressure source 176'; however, the dispensing bin 150' includes additional features that may be desirable to the performance of the bin 150. These features are described below.

Referring first to FIG. 29A, the dispensing bin 150' includes an upper half 151' and a lower half 152'. It can be seen that the front profiles of the upper and lower halves 151', 152' (i.e., those portions thereof that would mate with the low and high pressure sources 170', 176') are substantially identical, and form a "double-decker" bin. The bin 150' has an upper chamber 152*a* and a lower chamber 152*b*. The upper chamber 152*a* has a floor 152*c* that slopes downwardly from front to back and leads to a vertical passage 152*d* that empties into the lower chamber 152*b*. A hopper door 180' is mounted onto the upper rear portion of the upper half 151'. Thus, tablets can be supplied through the hopper door 180' to the upper chamber 152*a*; they remain there until they are fed via gravity down the floor 152*c* to the passage 152*d* and into the lower chamber 152*b*.

In operation, the bin 150' can be used to house tablets that can benefit from a larger capacity bin than the bin 150 illustrated and described above. For example, the tablets may be particularly bulky, or the tablets may be dispensed with great frequency, such that replenishment frequency of the bin can be reduced by having greater capacity. It can be seen from FIGS. 29*a* and 29*b* that the substantially identical profiles of the upper and lower halves 151', 152' enable the bin 150' to be inserted in any position in the system 40 that two vertically-stacked bins 150 might occupy, so that they can be interchanged easily as demand requires.

Referring again to FIG. 29*a*, the lower half 152' of the bin 150' includes a depending partition 152*e* that extends downwardly from the portion of the ceiling of the lower half 152' in front of the vertical passage 152*d*. The lower half 152' also includes a central partition 152*f* that spans the side walls of the lower half 152' just rearwardly of the screen 153*a'* located in the floor of the lower half 152'. The central partition divides the lower chamber 152*b* into four quadrants I, II, III and IV (with quadrants III and IV being bounded in the rear by the depending partition 152*e*).

The depending partition 152e and the central partition 152f can assist in directing the flow of tablets within the lower chamber 152b. In operation, air is drawn through the screen 153a', upwardly through the lower chamber 152b, and out of a screen 153b' in the ceiling of the lower half 152' (i.e., through quadrants I and II). Such air flow causes tablets in quadrant I to be agitated. Agitated tablets are either drawn into the dispensing channel 154' as described above or rise to quadrant II. Tablets that reach quadrant II either descend back into quadrant I for further agitation or are drawn over the top edge of the central partition 152f into quadrant III. Once in quadrant III, where there is no upward air flow, tablets descend downwardly into quadrant IV (aided by the presence of the depending partition 152e, which directs rearwardly-traveling tablets downwardly). In quadrant IV the descending tablets join tablets that have already arrived there from the vertical passage 152d. Tablets from quadrant IV are fed via gravity to quadrant I, where they are agitated as described above.

A dispensing bin having the configuration described above may benefit from the more organized and predictable tablet flow path, as this path can help to prevent jamming of the mouth of the dispensing channel 154'.

Figure 29C:
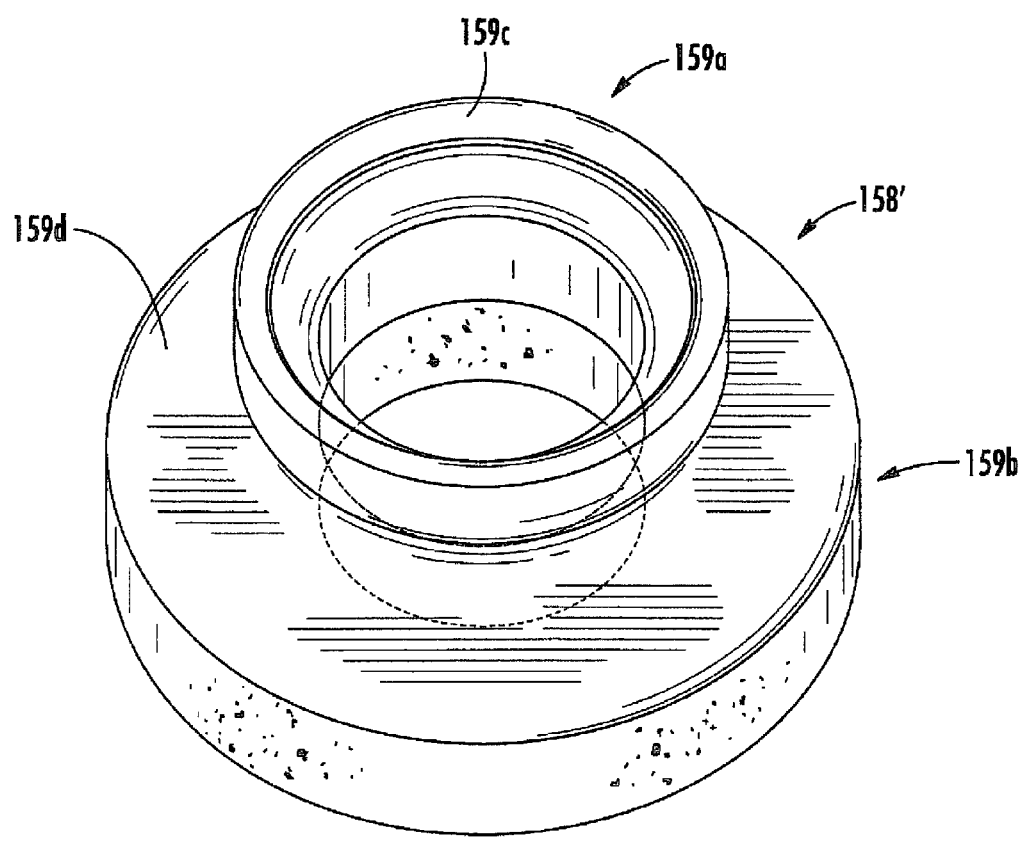
Figure 30:
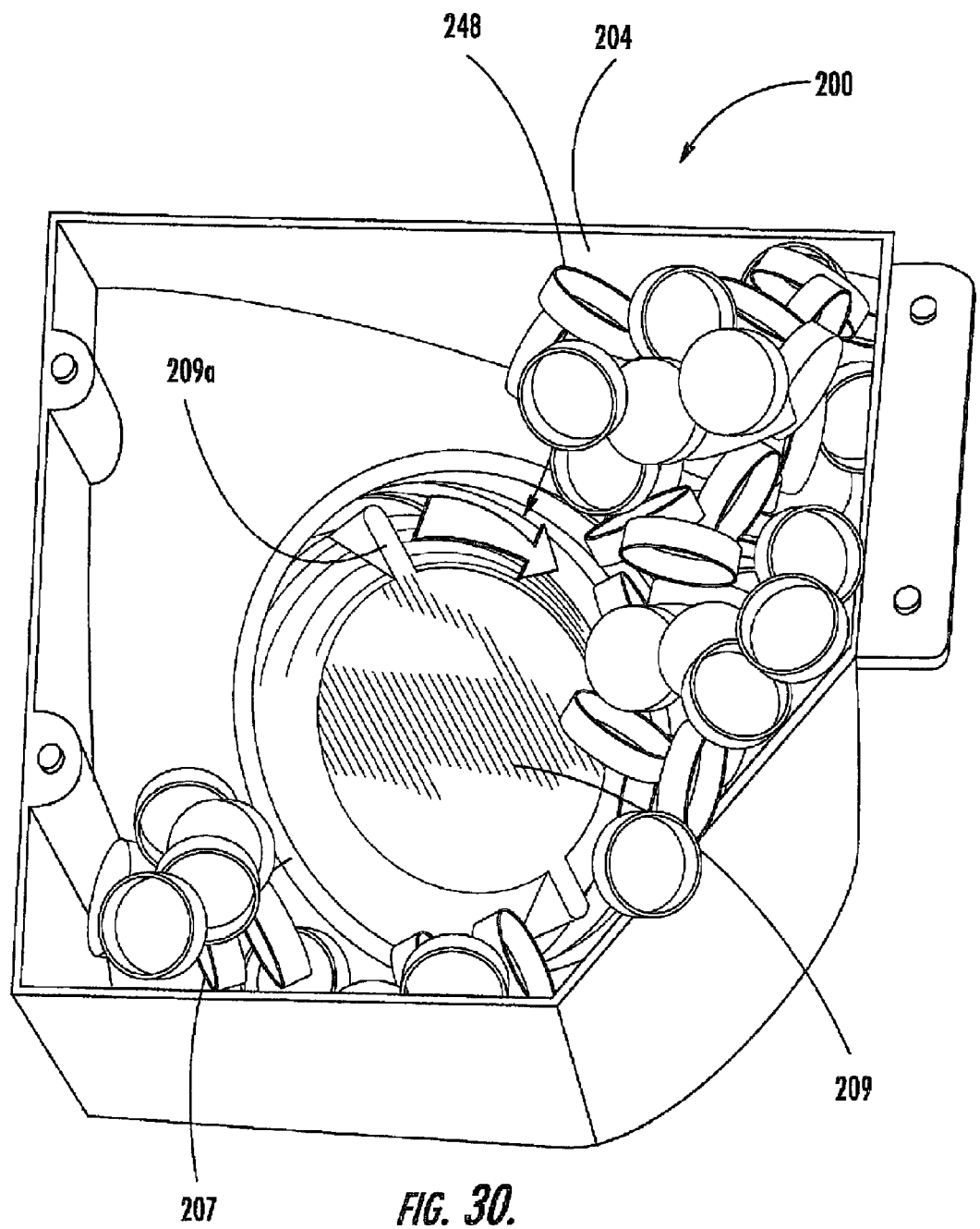
FIG. 30 is an enlarged perspective view of the closure dispenser of the closure dispensing station of the system of FIG. 2.
Figure 31:
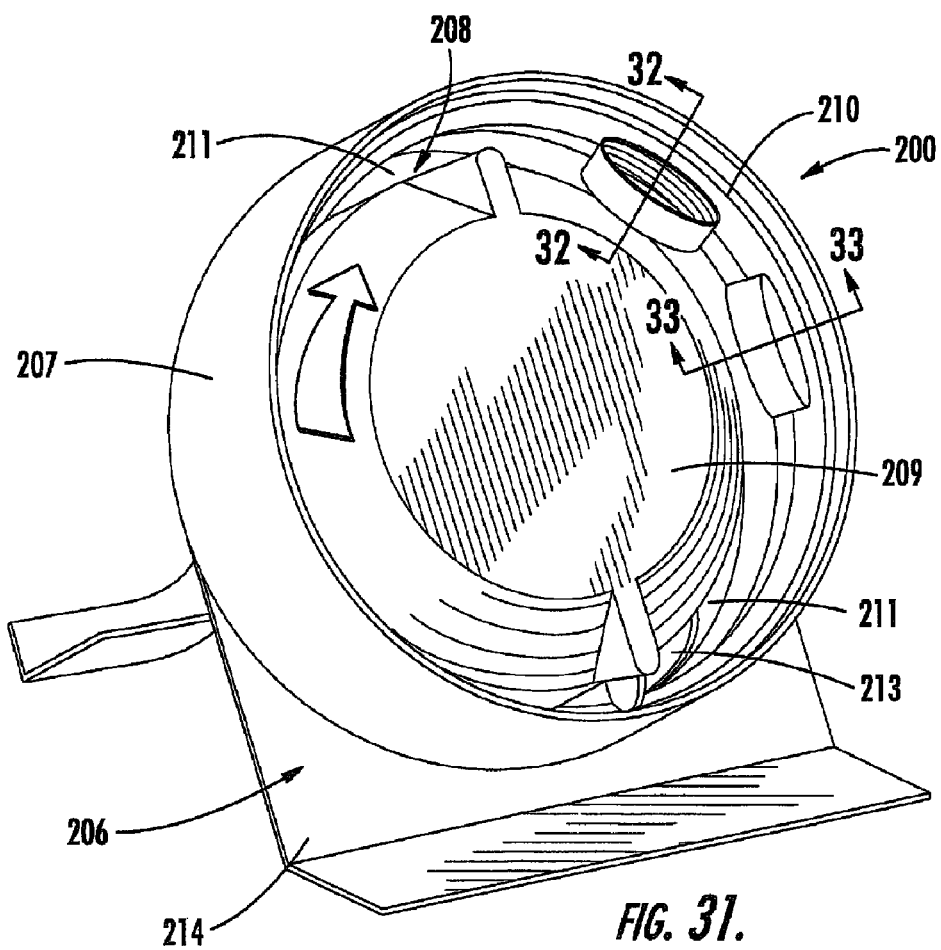
FIG. 31 is an enlarged perspective view of the closure dispenser of FIG. 30 with the closure supply bin removed.
Figure 32:
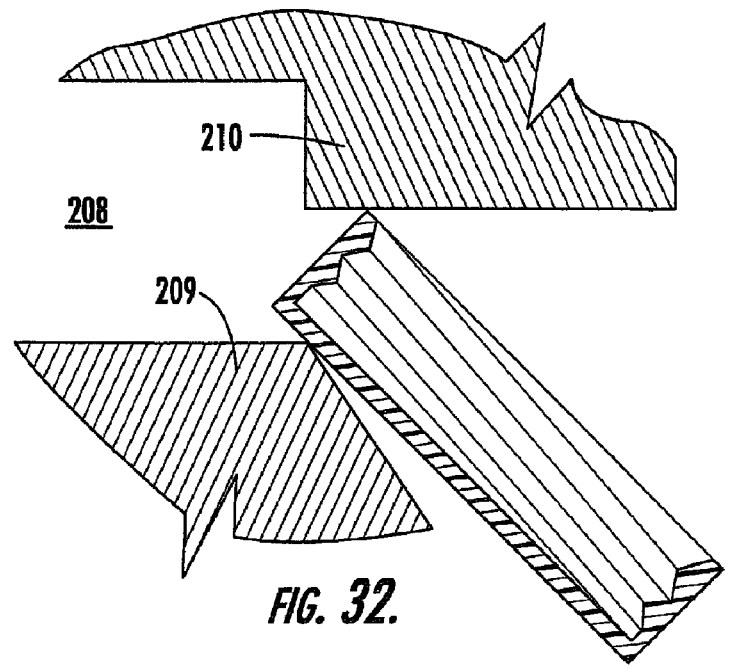
FIG. 32 is a greatly enlarged section view of a closure unable to be oriented with the closure dispenser of FIG. 30.
Figure 33:
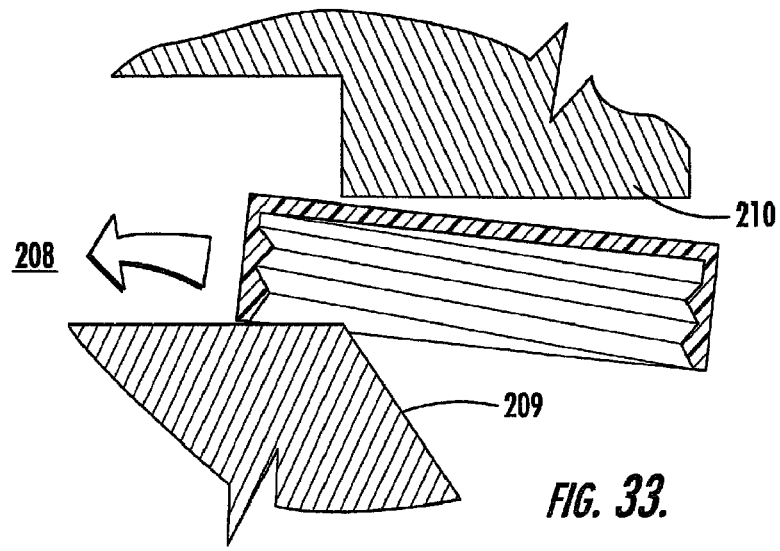
FIG. 33 is a greatly enlarged section view of a closure able to be oriented with the closure dispenser of FIG. 30.
Figure 34:
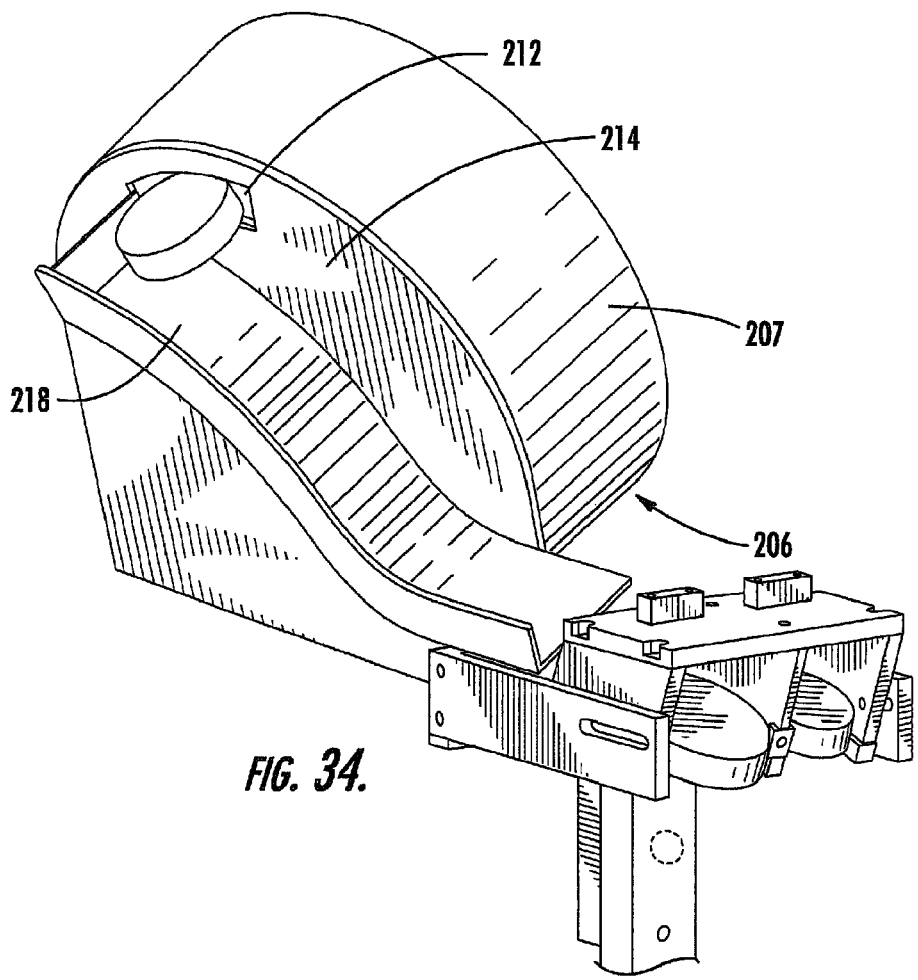
FIG. 34 is a bottom perspective view of the closure dispenser of FIG. 30.

Referring again to FIG. 29a and to FIG. 29c, the bin 150' includes an alternative embodiment of a splash guard, designated at 158', mounted to the downstream end of the dispensing channel 154'. The splash guard 158' includes a grasping portion 159a and a mating portion 159b. The grasping portion 159a includes a resilient lip 159c that fits over the end of the dispensing channel 154'. The lip 159c also has a base 159d that abuts the upper surface of the annular mating portion 159b. In some embodiments, the grasping portion 159a is formed of an elastomeric material, such as rubber or silicone, to enable it to be slipped over the end of the end of the dispensing channel 154'. The mating portion 152b is typically formed of a spongy, foamed material to enhance mating with a vial presented for dispensing. The resilient material forming the lip 159c can enable the splash guard to be easily mounted and removed in the event it wears out or deforms. The spongy material comprising the mating portion can enable the bin 150' to dispense into vials of different sizes and diameters without spilling tablets filling the vial, and can do so even if the vial is not positioned precisely against the splash guard 158'.

Referring now to FIGS. 30-37, the closure dispensing station 64 includes two closure dispensers 200 and two closure holders 202, each of which is mounted to the intermediate arch 55 of the frame 44 between the container dispensing station 58 and the labeling station 60. Typically, each closure dispenser 200 and closure holder 202 contains and manipulates a single size of closure. The closure dispensers 200 house a bulk supply of closures and dispense them, in a preferred orientation, one at a time to a respective closure holder 202, where they are secured onto a filled container. One each of a closure dispenser 200 and a closure holder 202 are described in detail below; those skilled in this art will appreciate that any number of closure dispensers and closure holders may be employed with the present invention.

The closure dispenser 200 (FIGS. 30-34) includes an open-ended bin 204 that feeds a rotatable hopper 206. The hopper 206 has an open top end to receive closures from the bin 204 and a circumferential groove 208 at its lower end that surrounds a central circular island 209. The groove 208 has a depth that is approximately the diameter of a closure and a width that is approximately the width of the closure. A circumferential protrusion 210 juts radially inwardly from the wall 207 of the hopper 206 above the groove 208 and island 209. The sizes and configurations of the groove 208, island 209 and protrusion 210 are such that a closure (which is a flat, open-ended cylinder) can enter the groove 208 from above only when the closure is oriented so that the open end of the closure faces the island 209. This occurs because the open end of the closure can receive a portion of the edge of the island 209, thereby allowing the closure to be positioned slightly farther from the wall 207 (and, therefore, slide into the groove 208) than a closure oriented with the closed end facing the island 209, which cannot pass between the island 209 and the protrusion 210 in this manner (compare FIGS. 32 and 33).

The floor 211 of the hopper 206 has an opening 213 through which one closure can pass. The floor 211 abuts a plate 214 (FIG. 34) that also includes at least one opening 212 that has a length in a direction substantially tangent to the groove 208 that is sufficient to pass one closure. The hopper 206 is rotatably mounted on the plate 214. A channel 218 is positioned below the opening 212 and leads to the closure holder 202; the channel 218 is sized such that the closure substantially maintains the orientation it takes upon exiting the opening 212.

Closures are dispensed by filling the bin with closures and rotating the hopper 206 relative to the plate 214. As the hopper 206 rotates, each closure tumbles until it eventually reaches the desired orientation and slides into the groove 208 (tumbling of the closures is augmented by two agitating projections 209a). As the hopper 206 continues to rotate, the closure eventually reaches the opening 213, at which point it passes through the opening 212 and falls into the channel 218. The channel 218 conveys the closure in its desired orientation to the closure holder 202.

Those skilled in this art will appreciate that other techniques for separating and orienting closures may also be employed. For example, a conventional "pick-and-place" device may be used. Additional sensors and controllers may also be used.

Figure 35:
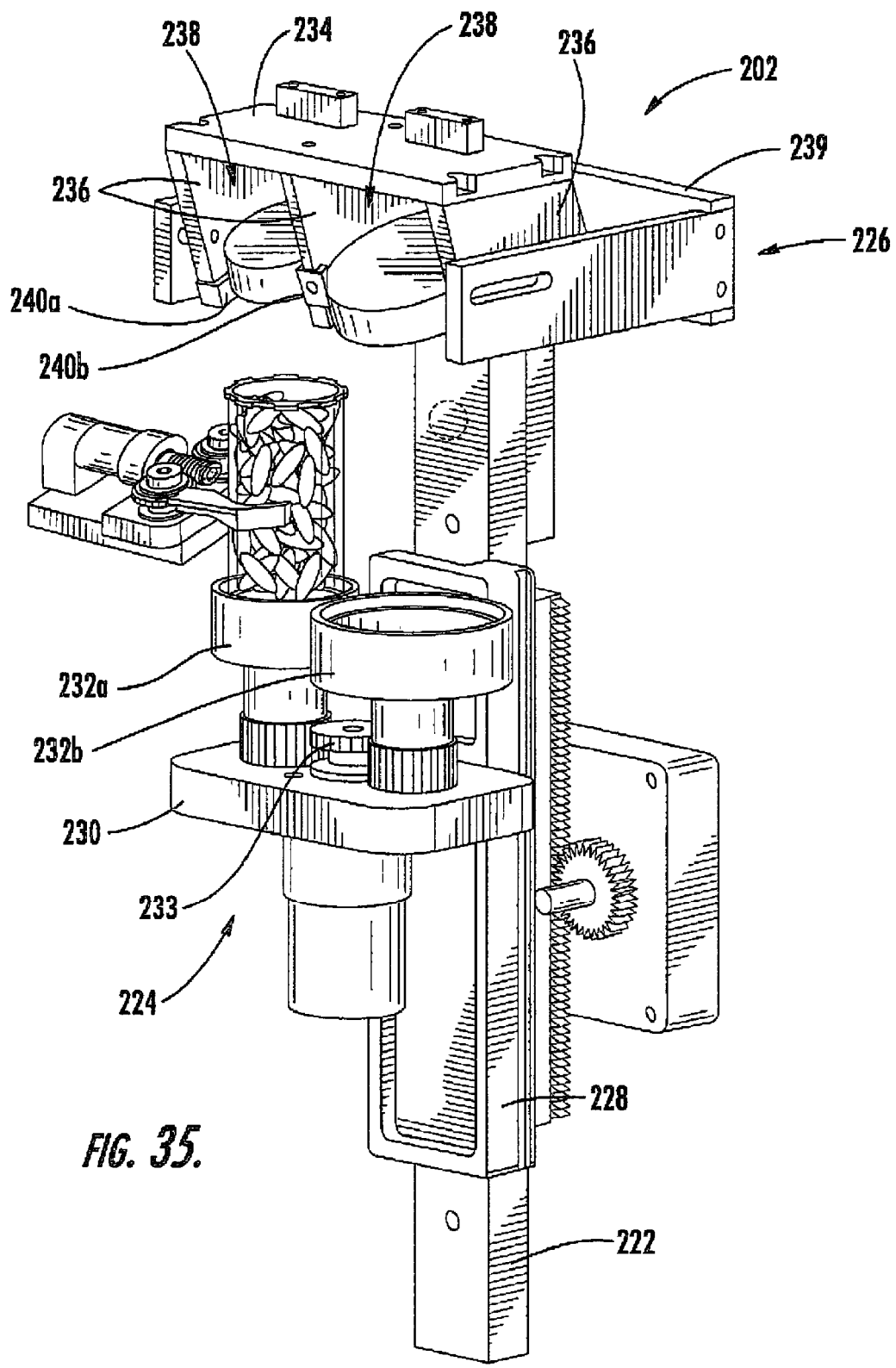
FIG. 35 is an enlarged side perspective view of the closure holder of the system of FIG. 2 with a filled container in a lower position.

Referring now to FIG. 35, the closure holder 202 includes a vertical mounting post 222 upon which are mounted a container receiving stage 224 and a closure holding stage 226. The container receiving stage 226 comprises a block 228 that is slidable relative to the mounting post 222 driven by a rack-and-pinion drive unit 227. A platform 230 extends generally horizontally away from the block 228. Two open-ended cups 232a, 232b sized to receive filled containers are mounted on the upper surface of the platform 230. A rotatable drive wheel 233 or other rotary drive unit is positioned between the cups 232a, 232b that rotates the cups 232a, 232b about their respective longitudinal axes; rotation of the drive wheel 233 is controlled by the controller 42.

Referring still to FIG. 35, the closure holding stage 226 has a ceiling 234 and three downwardly-extending walls 236 that form two closure securing compartments 238. A fork 239 is mounted to the mounting post 222 and forms the rear wall of the securing compartments 238; the fork 239 includes openings that receive closures from the channels 218. A pair of ledges 240a, 240b extend into each compartment 238 from the opposing surfaces of the walls 236. The ledges 240a, 240b extend a sufficient distance from the walls 236 that a closure cannot pass downwardly between the ledges 240a, 240b, but a container can pass upwardly between them. The ledges 240a, 240b, walls 236 and ceiling 234 are also configured so that a closure can pass forwardly (i.e., away from the fork 239) to allow a combined container and closure to pass out of the compartments 238.

Figure 36:
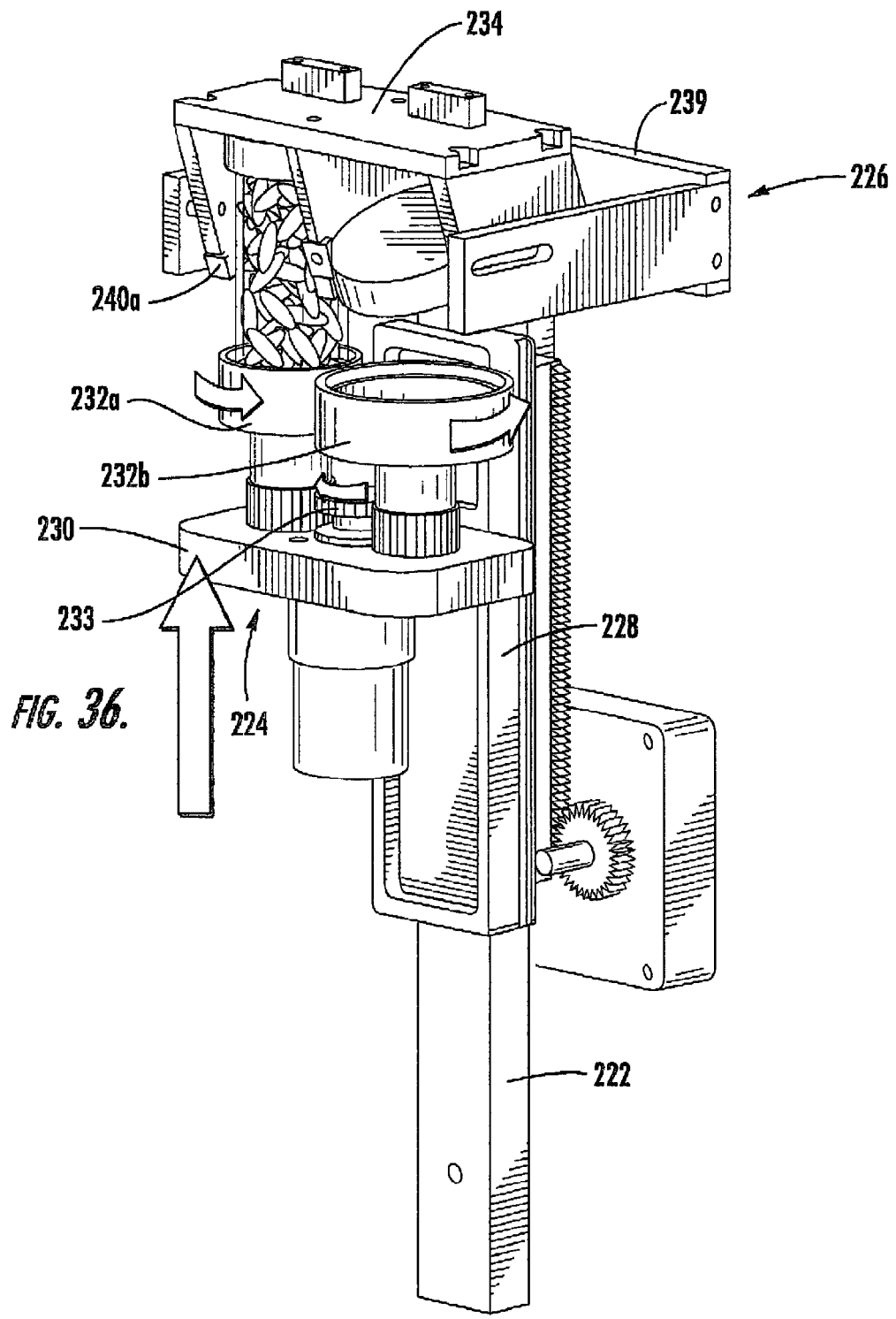
FIG. 36 is an enlarged side perspective view of the closure holder of FIG. 35 with the container raised to engage a closure.
Figure 37:
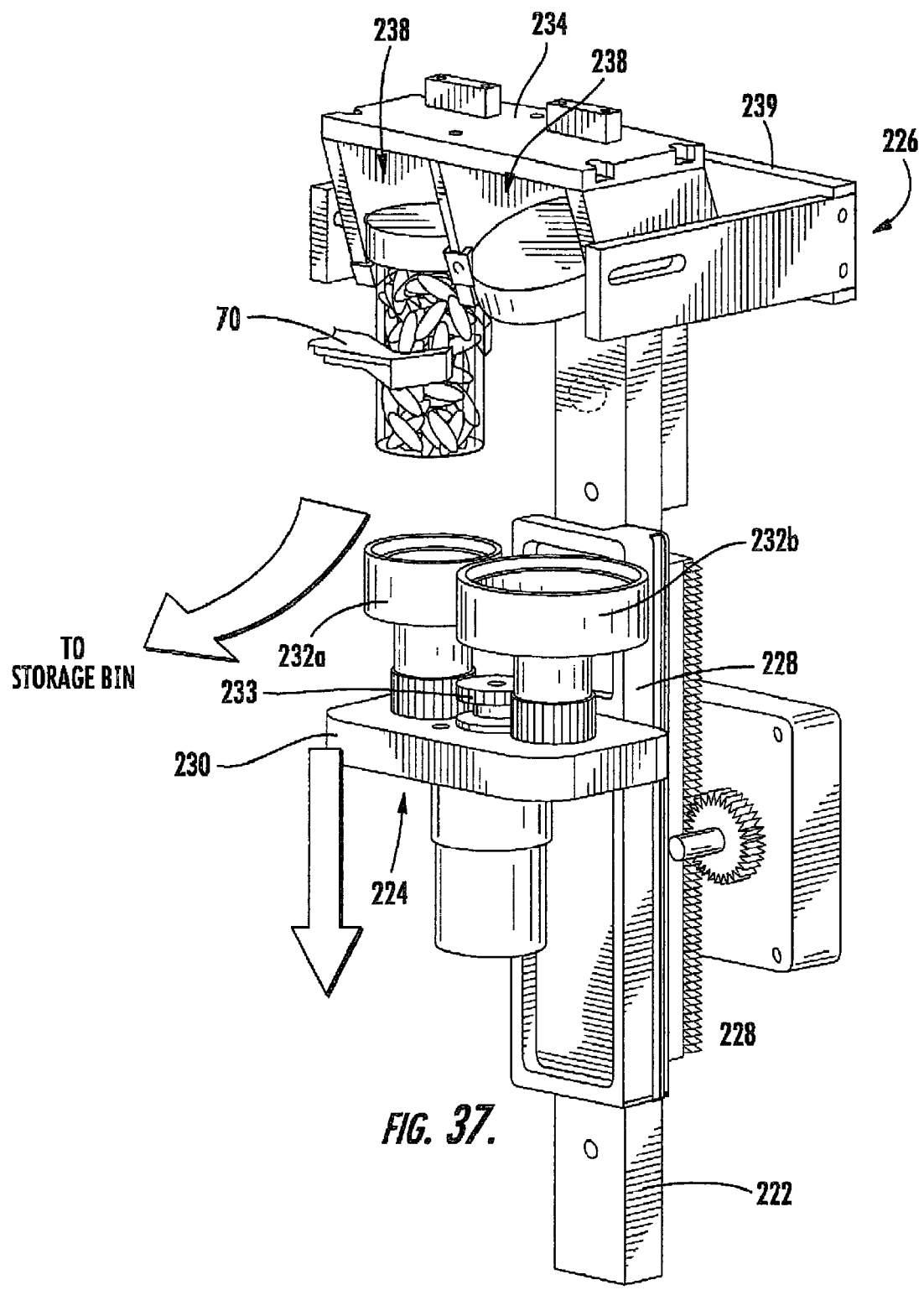
FIG. 37 is an enlarged side perspective view of the closure holder of FIG. 35 with the filled, closed container lowered.

Returning to the operation of the system 40, after the container is filled with tablets at the tablet dispensing station 62, the dispensing carrier 70 grasps the filled container, conveys it to the closure dispensing station 64, and places it in a selected cup 232a, 232b as directed by the controller 42 (FIG. 35). The block 228 slides upwardly relative to the mounting post 222, thereby moving the platform 230 upwardly. The platform 230 ascends, and the upper end of the container contacts and intercepts the closure positioned in the compartment 238. The container and closure continue to rise until the container compresses the closure against the ceiling 234 (FIG. 36). The selected cup 232a then rotates, thereby rotating the container, as the ceiling 234 holds the closure in place, causing the container to rotate relative to the closure. This rotation secures the closure to the container. The platform 230 then lowers; the closed container descends until the closure contacts the ledges 240a, 240b, with the closed container dangling therefrom (FIG. 37). The dispensing carrier 70 then moves to the closed container, grasps it, and moves it to the offloading station 66.

Figure 38B:
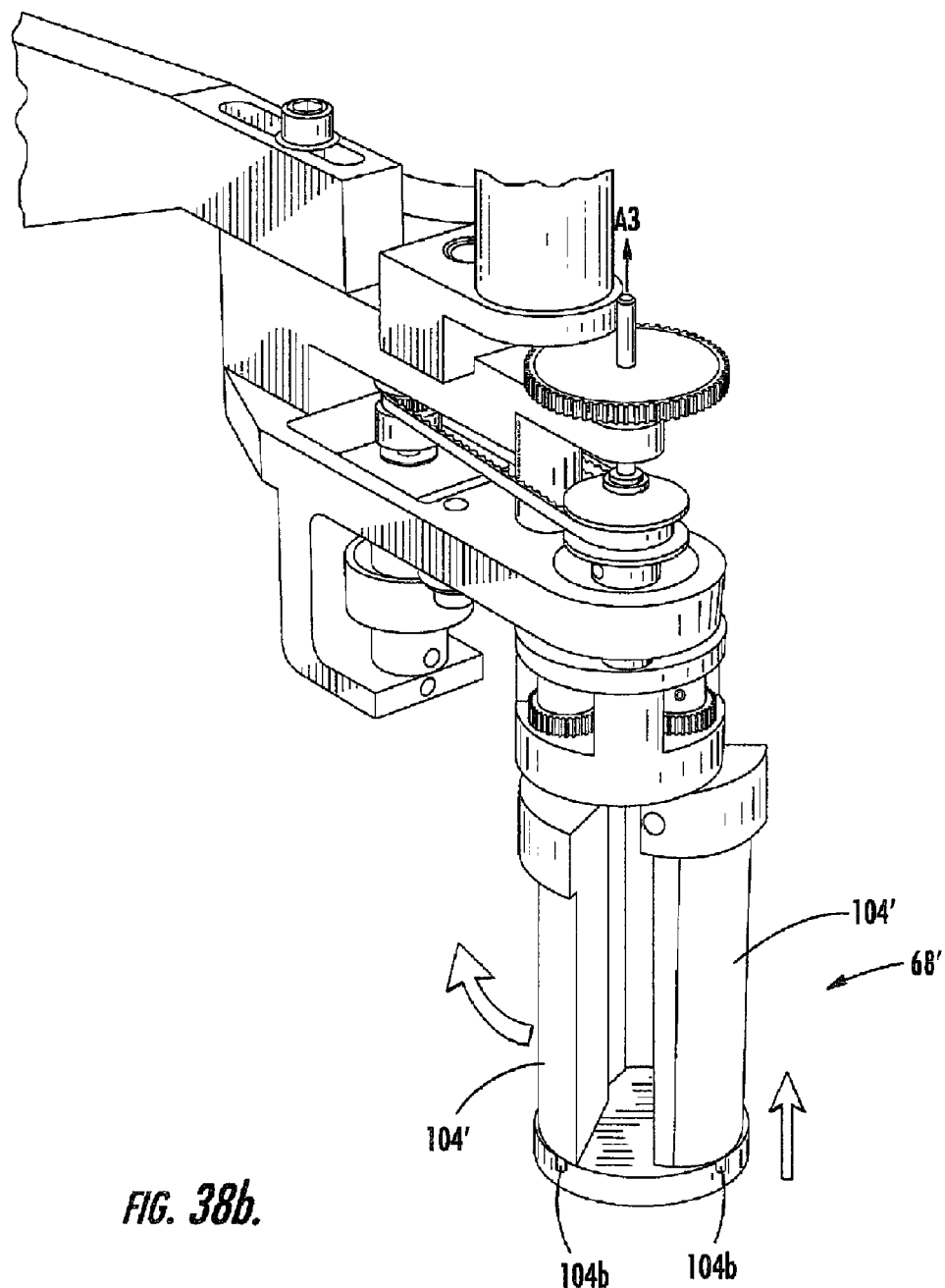
FIG. 38b is a perspective view of the labeling carrier of FIG. 38a gripping a cap.
Figure 38C:
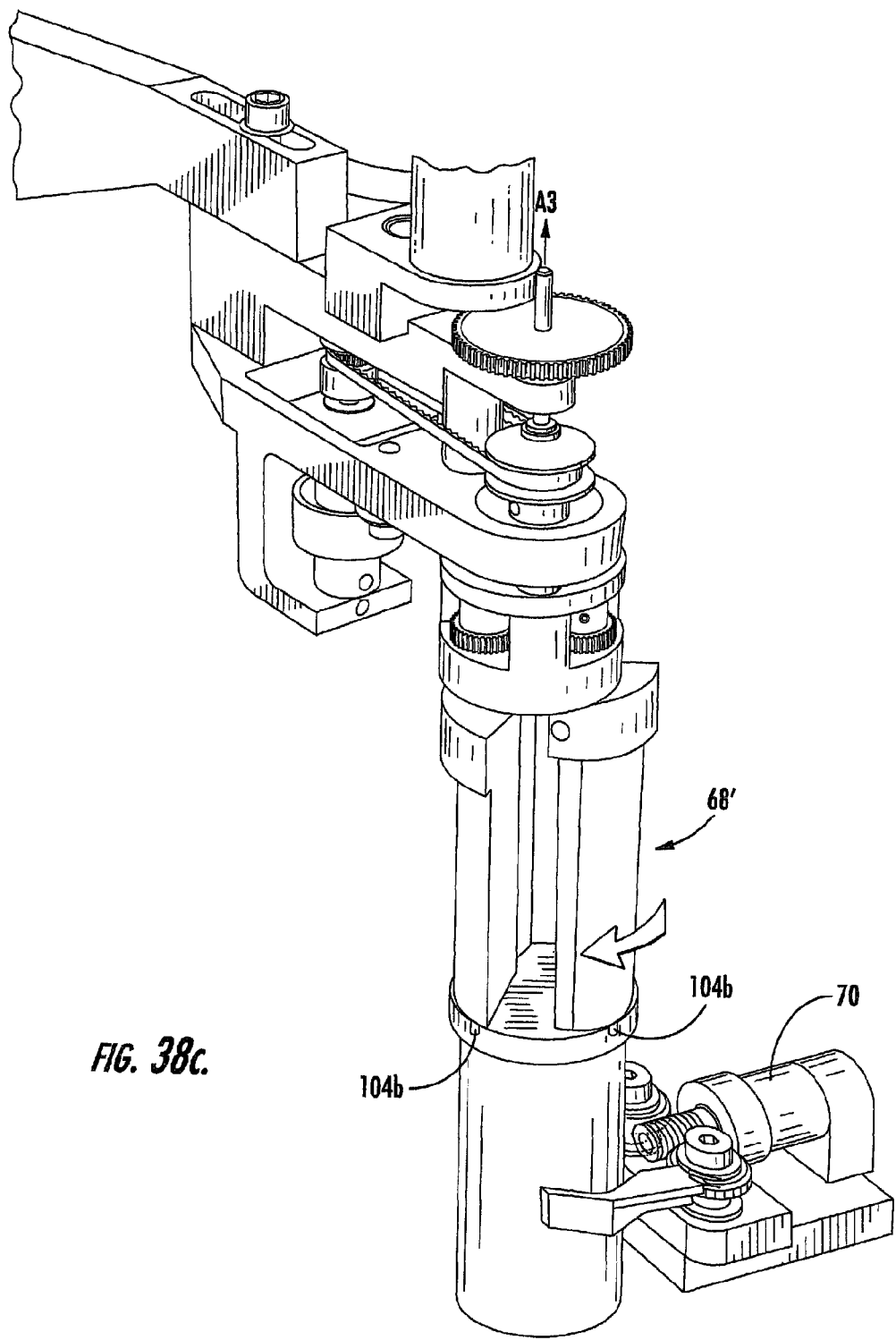
FIG. 38c is a perspective view of the labeling carrier of FIG. 38a applying a cap to a filled vial held by the dispensing carrier of FIG. 17.

Referring now to FIGS. 38a-38c, an alternative embodiment of the closure dispensing station, designated broadly at 64', is disclosed therein. The closure dispensing station 64' relies on a closure dispenser 200, such as that illustrated and described above, or with a dispensing track and platform such as that illustrated in FIG. 38a and designated at 201. Rather than the closure holder 202 described above, the closure dispensing station 64' relies on a modified labeling carrier 68' to apply a cap to a filled vial. The modified labeling carrier 68' includes gripping prongs 104b that project downwardly from the lower end of each finger 104'. Once a cap has been dispensed to the closure dispenser platform 200', the labeling carrier 64' approaches the cap with the fingers 104' rotated outwardly. After lowering the fingers 104' to an appropriate height, such that the prongs 104 are substantially the same height as the cap, the labeling carrier 68' rotates the fingers inwardly so that the prongs 104b grasp the cap. The labeling carrier 68' then conveys the cap to the filled vial held by the dispensing carrier 70. After positioning the cap over the vial, the labeling carrier 68' rotates the cap clockwise (viewed from above) to attach it to the vial. This configuration can simplify the operation of the system 40 and can enable the closure dispensing station 64' to handle different cap designs or varying sizes and configurations.

Referring now to FIG. 2, the offloading station 66 includes a plurality of compartments 250 positioned between the intermediate and upper arches 55, 54. These can be organized in any manner desired by the operator; for example, they may be organized by customer name, time of dispensing, contents of the container, or any other scheme. The dispensing carrier 70 conveys the closed container to the compartment directed by the controller 42 and releases it there. The dispensing carrier is then free to grasp another labeled container at the labeling station 60 and perform its operations again.

The foregoing is illustrative of the present invention, and is not to be construed as limiting thereof. Although exemplary embodiments of this invention have been described, those skilled in the art will readily appreciate that many modifications are possible in the exemplary embodiments without materially departing from the novel teachings and advantages of this invention. As such, all such modifications are intended to be included within the scope of this invention. The scope of the invention is to be defined by the following claims.

That which is claimed is:

1. An apparatus for dispensing containers, comprising:
   a plurality of dispensing tubes mounted in a generally vertical disposition and configured to receive a plurality of containers in vertically stacked relationship;
   a rotary drive unit associated with the dispensing tubes that rotates the dispensing tubes about a substantially vertical axis of rotation;
   a lower plate member positioned below the dispensing tubes, the lower plate member having a cutaway region positioned such that, as the dispensing tubes rotate about the axis of rotation, each dispensing tube passes over the cutaway region;
   a receptacle positioned below the cutaway region; and
   a dislodging structure mounted to the lower plate member away from the cutaway region that is positioned and configured such that, when a lowermost container in a dispensing tube is lodged with a second lowermost container in that dispensing tube, the dislodging structure dislodges the lowermost container from the second lowermost container.

2. The apparatus defined in claim 1, wherein the lower edge of each of the dispensing tubes is beveled, such that a radially outward portion of the lower edge is above a radially inward portion of each lower edge.

3. The apparatus defined in claim 1, wherein the dislodging structure comprises a guide member mounted to the lower plate member that is positioned to force the lowermost container radially outwardly upon contact therewith.

4. The apparatus defined in claim 1, wherein the cutaway area is bounded on one side by a contact edge, the contact edge being positioned such that the lowermost container strikes the contact edge as the dispensing tubes are rotated about the axis of rotation.

5. The apparatus defined in claim 1, wherein the lower plate member includes a ramp leading to the cutaway area upon which the lowermost container travels and descends.

6. The apparatus defined in claim 1, further comprising a guide member that forces the lowermost container radially inwardly so that the lowermost container does not fall into the cutaway area when passing thereover.

7. The apparatus defined in claim 1, further comprising an engagement ledge that projects radially outwardly from a spindle upon which the dispensing tubes are mounted into at least one of the dispensing tubes, the engagement ledge being positioned to support the second lowermost container in a dispensing tube and prevent descending thereof when the lowermost container in that dispensing tube exits the lower end of that dispensing tube.

8. An apparatus for dispensing containers, comprising:
   a plurality of dispensing tubes mounted in a generally vertical disposition and configured to receive a plurality of containers in vertically stacked relationship;
   a rotary drive unit associated with the dispensing tubes that rotates the dispensing tubes about a substantially vertical axis of rotation;
   a lower plate member positioned below the dispensing tubes, the lower plate member having a cutaway region with a contact edge, the cutaway region and the contact edge being positioned such that, as the dispensing tubes rotate about the axis of rotation, each dispensing tube passes over the cutaway region, wherein the lower plate member includes a ramp leading to the cutaway area upon which the lowermost container travels and descends; and
   a receptacle positioned below the cutaway region.

9. An apparatus for dispensing containers, comprising:
   a plurality of dispensing tubes mounted in a generally vertical disposition and configured to receive a plurality of containers in vertically stacked relationship;
   a rotary drive unit associated with the dispensing tubes that rotates the dispensing tubes about a substantially vertical axis of rotation, the rotary drive unit being configured such that the dispensing tubes may be rotated in a first rotative direction and in a second rotative direction opposite the first rotative direction;
a lower plate member positioned below the dispensing tubes, the lower plate member having a cutaway region;
a receptacle positioned below the cutaway region;
wherein the cutaway region is sized and positioned such that, as the dispensing tubes rotate about the axis of rotation in the first rotative direction, each dispensing tube passes over the cutaway region, such that a vial contained therein falls through the cutaway region into the receptacle, but when the dispensing tubes rotate in the second rotative direction, each dispensing tube passes over the cutaway region, but a vial contained therein does not fall through the cutaway region.

* * * * *

UNITED STATES PATENT AND TRADEMARK OFFICE
CERTIFICATE OF CORRECTION

PATENT NO. : 7,866,506 B2  
APPLICATION NO. : 11/935437  
DATED : January 11, 2011  
INVENTOR(S) : Daniels et al.

Page 1 of 1

It is certified that error appears in the above-identified patent and that said Letters Patent is hereby corrected as shown below:

<u>On the Title Page:</u>
Item (75) Inventors: Please delete "Richard D. Michelli, Raleigh, NC(US)"
and "Peter Klein, Durham, NC (US)"

Signed and Sealed this
Fifth Day of July, 2011

David J. Kappos
*Director of the United States Patent and Trademark Office*